US012781262B2

(12) United States Patent
Allie et al.

(10) Patent No.: US 12,781,262 B2
(45) Date of Patent: Nov. 3, 2026

(54) METHODS OF SCREENING TRANSPOSASES BY EMPLOYING TRANSPOSASES TO INDUCE TRANSPOSITION OF OLIGONUCLEOTIDES COMPRISING END SEQUENCES TO GENERATE INSERTION SITES FOR SEQUENCING

(71) Applicant: Kapa Biosystems, Inc., Wilmington, MA (US)

(72) Inventors: Raeeza Allie, Strandfontein (ZA); Michael Stuart Berry, Woodstock (ZA); William Bourn, Plumstead (ZA); Bjarne Faurholm, Rondebosh (ZA); Suzanne Margaret Huddy, Kenilworth (ZA); Martin Ranik, Santa Clara, CA (US); Du Toit Schabort, Bellvile (ZA)

(73) Assignee: Kapa Biosystems, Inc., Wilmington, MA (US)

( * ) Notice: Subject to any disclaimer, the term of this patent is extended or adjusted under 35 U.S.C. 154(b) by 697 days.

(21) Appl. No.: 16/642,813

(22) PCT Filed: Aug. 30, 2018

(86) PCT No.: PCT/US2018/048823

§ 371 (c)(1),
(2) Date: Feb. 27, 2020

(87) PCT Pub. No.: WO2019/046564

PCT Pub. Date: Mar. 7, 2019

(65) Prior Publication Data

US 2020/0347441 A1 Nov. 5, 2020

Related U.S. Application Data

(60) Provisional application No. 62/552,214, filed on Aug. 30, 2017.

(51) Int. Cl.
*C12Q 1/6811* (2018.01)
*C12N 15/10* (2006.01)
*C12Q 1/6827* (2018.01)

(52) U.S. Cl.
CPC ........ *C12Q 1/6811* (2013.01); *C12N 15/1082* (2013.01); *C12Q 1/6827* (2013.01); *C12Q 2522/101* (2013.01); *C12Q 2525/155* (2013.01); *C12Q 2525/179* (2013.01); *C12Q 2525/191* (2013.01); *C12Q 2563/179* (2013.01)

(58) Field of Classification Search
None
See application file for complete search history.

(56) References Cited

U.S. PATENT DOCUMENTS

| | | | |
|---|---|---|---|
| 9,005,935 | B2 | 4/2015 | Belyaev |
| 9,644,199 | B2 | 5/2017 | Belyaev |
| 9,790,476 | B2 | 10/2017 | Gloeckner et al. |
| 2012/0301925 | A1 | 11/2012 | Belyaev |
| 2014/0093916 | A1 | 4/2014 | Belyaev |
| 2017/0058326 | A1 | 3/2017 | Belyaev |

FOREIGN PATENT DOCUMENTS

| | | | | |
|---|---|---|---|---|
| CN | 106754811 A | 5/2017 | | |
| WO | 2004/093645 A3 | 4/2004 | | |
| WO | WO-2004093645 A2 * | 11/2004 | .............. | C12N 9/22 |
| WO | 2014/189957 A2 | 11/2014 | | |
| WO | 2014/189957 A3 | 11/2014 | | |
| WO | 2015/095226 A2 | 6/2015 | | |
| WO | 2015/160895 A2 | 10/2015 | | |
| WO | 2015/179706 A1 | 11/2015 | | |
| WO | 2016/138490 A1 | 6/2016 | | |

OTHER PUBLICATIONS

Green, et al., "Insertion site preference of Mu, Tn5, and Tn7 transposons," Mobile DNA 3:3 (2012).
Kia, et al., "Improved genome sequencing using an engineered transposase," BMC Biotechnology 17:6 (2017).
Naumann, et al., "Tn5 Transposase with an Altered Specificity for Transposon Ends," Journal of Bacteriology 184 (1):233-240 (2002).
Zhou, et al., "Molecular Genetic Analysis of Transposase-End DNA Sequence Recognition: Cooperativity of Three Adjacent Base-pairs in Specific Interaction with a Mutant Tn5 Transposase," J. Mol. Biol. 276:913-925 (1998).
Written Opinion of the International Searching Authority, for International Patent Application No. PCT/US2018/048823 (Mar. 7, 2019).
International Search Report, for International Patent Application No. PCT/US2018/048823 (Mar. 7, 2019).
Brian Green, et al., "Insertion site preference of Mu, Tn5, and Tn7 transposons," Mobile DNA Journal 3 (2012).
Li-Hua Zhou, et al., "Applications of Single-Cell Sequencing Techniques in Medicine," Pharmaceutical Biotechnology 23(6):519-525 (2016) (with English machine translation).

* cited by examiner

*Primary Examiner* — G. Steven Vanni
(74) *Attorney, Agent, or Firm* — Eric Grant Lee

(57) ABSTRACT

The disclosure provides compositions and methods for high-throughput screening a plurality of transposases to identify rare mutations that affect desired features of the transposase. Compositions of the disclosures are provided that facilitate the high-throughput screening methods of the disclosure.

2 Claims, 42 Drawing Sheets

Specification includes a Sequence Listing.

| Lane | Transposase carried by minimal test vector |
|---|---|
| 1 | TnAa-transposase [wild-type] |
| 2 | TnAa-transposase [P47K] |
| 3 | TnAa-transposase [M50A] |
| 4 | TnAa-transposase [P47K M50A+Deletion ] |
| 5 | Tn5-transposase [Hyper] |

| Lane | Type of blunt ended phosphorylated vector |
|---|---|
| 1 | Tn5-transposase [Hyper] full-length vector |
| 2 | Mobilisable Kanamycin region only |
| 3 | TnAa-transposase [M50A ] full-length vector |

| Lane | Type of vector and ligation status |
|---|---|
| 1 | Tn5-transposase [Hyper] vector ligated |
| 2 | Mobilisable Kanamycin region ligated |
| 3 | TnAa-transposase [M50A ] vector ligated |
| 4 | Tn5-transposase [Hyper] vector not ligated |
| 5 | Mobilisable Kanamycin region not ligated |
| 6 | TnAa-transposase [M50A ] vector not ligated |

5'-TCAGGTTTATTCCCCGCTAGAGCAGGGATTGTTGACCGGCA-3'
5'-GTTAGCGTCAGCCCGCCCCATTGCCGGGTTTCAACCCCGCT-3'
5'-CCACTCTCGATCCCAGTGCATATGCGGGGTGATGTGAACGC-3'
5'-CTTCTCCGTTACCCGGCTCCTGGTCGGGTAACTCCCCTCTC-3'
5'-GCAACGTGCTTCCCCGCCACCGGCGGGGTTTTTTTCTGCCT-3'
5'-CCGGTCCACACCCCGGCCCTTAACTGGGGTAAATAAGGAGA-3'
5'-TACTTTTATGACCCTGCCGCATGGCAGGGTTTTTTATACCT-3'
5'-ATAATCTGAAGCCCCGGCCATGTGCCGGGGTTTCTTTTTGA-3'
5'-GGCAATCGTAGCCCAGCTCATTCAGCCGGGTTTCGAAATCC-3'

FIG. 14A

SEQUENCE LISTING

```
<160> NUMBER OF SEQ ID NOS: 23

<210> SEQ ID NO 1
<211> LENGTH: 477
<212> TYPE: PRT
<213> ORGANISM: Alishewanella aestuarii

<400> SEQUENCE: 1

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
                165                 170                 175

Gly Ser Met Met Ser Asn Val Ile Ala Val Cys Asp Arg Glu Ala Asp
            180                 185                 190
```

```
Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Leu Glu
465                 470                 475


<210> SEQ ID NO 2
<211> LENGTH: 457
<212> TYPE: PRT
<213> ORGANISM: Alishewanella aestuarii

<400> SEQUENCE: 2

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Pro Ala
        35                  40                  45

Asp Met Glu Gly Ala Tyr Arg Phe Ile Arg Asn Glu His Val Asn Ala
    50                  55                  60

Asp Ala Ile Ala Lys Ala Gly Tyr Leu Val Thr Ala Ala Gln Ala Ala
65                  70                  75                  80

Lys His Asn Leu Leu Leu Ala Leu Glu Asp Thr Thr Ala Ile Thr Tyr
                85                  90                  95
```

Ser His Arg Ser Val Arg Asp Glu Leu Gly His Val Asn Gln Gly Asn
100 105 110

Asn Tyr Arg Gly Ile Leu Ala His Ser Val Leu Leu Phe Ala Pro Glu
115 120 125

Gln Gln Glu Leu Val Gly Leu Ile Glu Gln Ser Arg Trp Thr Arg Asp
130 135 140

Ile Ser Thr Arg Gly Lys Lys His Val Arg Thr Gln Thr Pro Tyr Glu
145 150 155 160

Glu Lys Glu Ser Phe Lys Trp Gln Ser Ala Ser Val Asn Leu Ser Ala
165 170 175

Arg Leu Gly Thr Lys Met Ala Asp Val Ile Ser Val Cys Asp Arg Glu
180 185 190

Ala Asp Ile Tyr Glu Tyr Leu Gln Tyr Lys Leu Ser Lys Gln His Arg
195 200 205

Phe Val Val Arg Ser Met Gln Ser Arg His Ile Glu Gln Ser Glu Gln
210 215 220

Lys Leu Tyr Asp Tyr Ala Ala Gly Leu Glu Ser Ala Gly Gln Lys Gln
225 230 235 240

Ile His Ile Ala Gln Lys Gly Gly Arg Lys Ala Arg Thr Ala Thr Val
245 250 255

Asp Ile Val Phe Ala Pro Val Thr Leu Gln Val Pro Ala Asn Lys Arg
260 265 270

Gly Glu Ser Leu Ser Leu Tyr Tyr Val Gly Cys Glu Glu Arg Ala Asp
275 280 285

Asp Lys Asn Ala Leu Asn Trp His Leu Leu Thr Thr Glu Pro Val Gln
290 295 300

Ser Lys Ala Asp Ala Leu Asn Ile Ile Arg Tyr Tyr Glu His Arg Trp
305 310 315 320

Leu Val Glu Glu Tyr His Lys Ala Trp Lys Thr Asp Gly Thr Asp Ile
325 330 335

Glu Asn Ala Arg Leu Gln Ser Lys Asp Asn Ile Glu Arg Leu Val Thr
340 345 350

Ile Ser Ala Phe Ile Ala Val Arg Ile Val Gln Leu Lys Phe Ala Arg
355 360 365

Glu Gln Pro Asp Glu Ile Ser Cys Glu Gln Val Leu Ser Pro Lys Ala
370 375 380

Trp Lys Leu Leu Trp Ile Lys Arg Val Ser Arg Thr Leu Pro Asp Thr
385 390 395 400

Val Pro Ser Met Lys Trp Ala Tyr Thr Glu Leu Ala Lys Leu Gly Gly
405 410 415

Trp Lys Asp Thr Lys Gln Thr Gly Lys Ala Ser Val Lys Val Leu Trp
420 425 430

Gln Gly Trp Phe Lys Leu Gln Thr Ile Leu Glu Gly Tyr Asp Leu Ala
435 440 445

Lys Ser Leu Glu Ala Asp Leu Leu Glu
450 455

<210> SEQ ID NO 3
<211> LENGTH: 457
<212> TYPE: PRT
<213> ORGANISM: Alishewanella aestuarii

<400> SEQUENCE: 3

Met Asn Asn Ala Gln Trp Ala Lys Ser Thr Phe Gly Gln Ala Asp Leu

-continued

```
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Lys Ala
        35                  40                  45

Asp Ala Glu Gly Ala Tyr Arg Phe Ile Arg Asn Glu His Val Asn Ala
    50                  55                  60

Asp Ala Ile Ala Lys Ala Gly Tyr Leu Val Thr Ala Ala Gln Ala Ala
65                  70                  75                  80

Lys His Asn Leu Leu Leu Ala Leu Glu Asp Thr Thr Ala Ile Thr Tyr
                85                  90                  95

Ser His Arg Ser Val Arg Asp Glu Leu Gly His Val Asn Gln Gly Asn
            100                 105                 110

Asn Tyr Arg Gly Ile Leu Ala His Ser Val Leu Leu Phe Ala Pro Glu
        115                 120                 125

Gln Gln Glu Leu Val Gly Leu Ile Glu Gln Ser Arg Trp Thr Arg Asp
    130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
        195                 200                 205

Phe Val Val Arg Ser Met Gln Ser Arg His Ile Glu Gln Ser Glu Gln
    210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
                245                 250                 255

Asp Ile Val Phe Ala Pro Val Thr Leu Gln Val Pro Ala Asn Lys Arg
            260                 265                 270

Gly Glu Ser Leu Ser Leu Tyr Tyr Val Gly Cys Glu Glu Arg Ala Asp
        275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg Leu Gln Ser Lys Asp Asn Ile Glu Arg Leu Val Thr
            340                 345                 350

Ile Ser Ala Phe Ile Ala Val Arg Ile Val Gln Leu Lys Phe Ala Arg
        355                 360                 365

Glu Gln Pro Asp Glu Ile Ser Cys Glu Gln Val Leu Ser Pro Lys Ala
    370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
                405                 410                 415

Trp Lys Asp Thr Lys Gln Thr Gly Lys Ala Ser Val Lys Val Leu Trp
            420                 425                 430
```

```
Gln Gly Trp Phe Lys Leu Gln Thr Ile Leu Glu Gly Tyr Asp Leu Ala
        435                 440                 445

Lys Ser Leu Glu Ala Asp Leu Leu Glu
    450                 455


<210> SEQ ID NO 4
<211> LENGTH: 457
<212> TYPE: PRT
<213> ORGANISM: Alishewanella aestuarii

<400> SEQUENCE: 4

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Pro Ala
        35                  40                  45

Asp Ala Glu Gly Ala Tyr Arg Phe Ile Arg Asn Glu His Val Asn Ala
    50                  55                  60

Asp Ala Ile Ala Lys Ala Gly Tyr Leu Val Thr Ala Ala Gln Ala Ala
65                  70                  75                  80

Lys His Asn Leu Leu Leu Ala Leu Glu Asp Thr Thr Ala Ile Thr Tyr
                85                  90                  95

Ser His Arg Ser Val Arg Asp Glu Leu Gly His Val Asn Gln Gly Asn
            100                 105                 110

Asn Tyr Arg Gly Ile Leu Ala His Ser Val Leu Leu Phe Ala Pro Glu
        115                 120                 125

Gln Gln Glu Leu Val Gly Leu Ile Glu Gln Ser Arg Trp Thr Arg Asp
    130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
        195                 200                 205

Phe Val Val Arg Ser Met Gln Ser Arg His Ile Glu Gln Ser Glu Gln
    210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
                245                 250                 255

Asp Ile Val Phe Ala Pro Val Thr Leu Gln Val Pro Ala Asn Lys Arg
            260                 265                 270

Gly Glu Ser Leu Ser Leu Tyr Tyr Val Gly Cys Glu Glu Arg Ala Asp
        275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg Leu Gln Ser Lys Asp Asn Ile Glu Arg Leu Val Thr
```

```
            340                 345                 350

Ile Ser Ala Phe Ile Ala Val Arg Ile Val Gln Leu Lys Phe Ala Arg
        355                 360                 365

Glu Gln Pro Asp Glu Ile Ser Cys Glu Gln Val Leu Ser Pro Lys Ala
    370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
                405                 410                 415

Trp Lys Asp Thr Lys Gln Thr Gly Lys Ala Ser Val Lys Val Leu Trp
            420                 425                 430

Gln Gly Trp Phe Lys Leu Gln Thr Ile Leu Glu Gly Tyr Asp Leu Ala
        435                 440                 445

Lys Ser Leu Glu Ala Asp Leu Leu Glu
    450                 455


<210> SEQ ID NO 5
<211> LENGTH: 457
<212> TYPE: PRT
<213> ORGANISM: Alishewanella aestuarii

<400> SEQUENCE: 5

Met Asn Asn Ala Gln Trp Ala Lys Ser Thr Phe Gly Gln Ala Asp Leu
1               5                   10                  15

Gly Asp Pro Arg Arg Thr Thr Arg Leu Val Lys Leu Ala Glu Thr Leu
            20                  25                  30

Ala Asn Asp Pro Gly Lys Pro Phe Val Ser Ile Thr Gln Ser Lys Ala
        35                  40                  45

Asp Met Glu Gly Ala Tyr Arg Phe Ile Arg Asn Glu His Val Asn Ala
    50                  55                  60

Asp Ala Ile Ala Lys Ala Gly Tyr Leu Val Thr Ala Ala Gln Ala Ala
65                  70                  75                  80

Lys His Asn Leu Leu Leu Ala Leu Glu Asp Thr Thr Ala Ile Thr Tyr
                85                  90                  95

Ser His Arg Ser Val Arg Asp Glu Leu Gly His Val Asn Gln Gly Asn
            100                 105                 110

Asn Tyr Arg Gly Ile Leu Ala His Ser Val Leu Leu Phe Ala Pro Glu
        115                 120                 125

Gln Gln Glu Leu Val Gly Leu Ile Glu Gln Ser Arg Trp Thr Arg Asp
    130                 135                 140

Ile Ser Thr Arg Gly Lys Lys His Val Arg Thr Gln Thr Pro Tyr Glu
145                 150                 155                 160

Glu Lys Glu Ser Phe Lys Trp Gln Ser Ala Ser Val Asn Leu Ser Ala
                165                 170                 175

Arg Leu Gly Thr Lys Met Ala Asp Val Ile Ser Val Cys Asp Arg Glu
            180                 185                 190

Ala Asp Ile Tyr Glu Tyr Leu Gln Tyr Lys Leu Ser Lys Gln His Arg
        195                 200                 205

Phe Val Val Arg Ser Met Gln Ser Arg His Ile Glu Gln Ser Glu Gln
    210                 215                 220

Lys Leu Tyr Asp Tyr Ala Ala Gly Leu Glu Ser Ala Gly Gln Lys Gln
225                 230                 235                 240

Ile His Ile Ala Gln Lys Gly Gly Arg Lys Ala Arg Thr Ala Thr Val
                245                 250                 255
```

```
Asp Ile Val Phe Ala Pro Val Thr Leu Gln Val Pro Ala Asn Lys Arg
            260                 265                 270

Gly Glu Ser Leu Ser Leu Tyr Tyr Val Gly Cys Glu Glu Arg Ala Asp
        275                 280                 285

Asp Lys Asn Ala Leu Asn Trp His Leu Leu Thr Thr Glu Pro Val Gln
    290                 295                 300

Ser Lys Ala Asp Ala Leu Asn Ile Ile Arg Tyr Tyr Glu His Arg Trp
305                 310                 315                 320

Leu Val Glu Glu Tyr His Lys Ala Trp Lys Thr Asp Gly Thr Asp Ile
                325                 330                 335

Glu Asn Ala Arg Leu Gln Ser Lys Asp Asn Ile Glu Arg Leu Val Thr
            340                 345                 350

Ile Ser Ala Phe Ile Ala Val Arg Ile Val Gln Leu Lys Phe Ala Arg
        355                 360                 365

Glu Gln Pro Asp Glu Ile Ser Cys Glu Gln Val Leu Ser Pro Lys Ala
    370                 375                 380

Trp Lys Leu Leu Trp Ile Lys Arg Val Ser Arg Thr Leu Pro Asp Thr
385                 390                 395                 400

Val Pro Ser Met Lys Trp Ala Tyr Thr Glu Leu Ala Lys Leu Gly Gly
                405                 410                 415

Trp Lys Asp Thr Lys Gln Thr Gly Lys Ala Ser Val Lys Val Leu Trp
            420                 425                 430

Gln Gly Trp Phe Lys Leu Gln Thr Ile Leu Glu Gly Tyr Asp Leu Ala
        435                 440                 445

Lys Ser Leu Glu Ala Asp Leu Leu Glu
    450                 455
```

<210> SEQ ID NO 6
<211> LENGTH: 2733
<212> TYPE: DNA
<213> ORGANISM: Alishewanella aestuarii

<400> SEQUENCE: 6

```
agatctccat cgaatggcca gatgattaat tcctaatttt tgttgacact ctatcattga     60

tagagttatt ttaccactcc ctatcagtga tagagaaaag tgaaatgaat agttcgacaa    120

aaatctagaa ataattttgt ttaactttat gatggagcat accatggccc accaccacca    180

ccaccaccat atgatcacct ctgccctgca tcgcgcggct gattgggcga aatccgtctt    240

ctcatcagcg gcactgggcg acccgcggcg taccgcgcgt ctggttaatg tggcggctca    300

gctggctaaa tacagcggga aaagtattac gatcagtagc gaagggtcaa aagcggcaca    360

agaaggagca tatcgtttta tccgcaatcc gaatgtctcc gccgaggcca tccgcaaagc    420

gggcgccatg caaacagtga aattggcaca ggaattcccg gaactgttgg ccattgagga    480

taccacatcg cttagctatc gtcaccaagt cgcagaagaa ctgggaaaat taggctctat    540

tcaggataaa tctcgtggtt ggtgggtgca ctctgtttta ttactggaag cgaccacctt    600

ccgtaccgtg ggctgctgc atcaggaatg gtggatgcgg ccagatgacc cagcggacgc    660

cgacgaaaaa gaatctggta aatggttggc ggctgcggcg acctcgcgcc tccgtatggg    720

ttccatgatg agcaacgtca ttgcagtgtg cgatcgcgaa gctgatattc atgcgtacct    780

tcaggataaa ctggcgcaca acgagcgctt cgtcgtgcgc agcaaacatc cccgtaagga    840

cgtcgaatca ggtctgtatt tgtatgacca tctgaaaaat cagccggaac tgggaggata    900

tcaaatttcg atcccgcaga agggagtcgt ggataaacgc ggcaaacgta aaaatcgtcc    960
```

```
agctcgcaaa gccagcttga gtttgcgcag cggtcgtatt accctcaaac aggggaacat   1020

taccctgaac gctgtactcg cggaggagat caatcccccc aagggcgaaa caccgttaaa   1080

atggttactg ttaacatctg aacccgttga gagtctggct caagcactgc gcgtgatcga   1140

tatttacacc catcgctggc gcattgaaga attccataaa gcatggaaga ccggcgcggg   1200

cgcggaacgc caacgtatgg aagaaccgga taacctcgaa cggatggtca gcatcctgag   1260

ctttgttgcg gtacgtctgc ttcagctgcg tgaaagcttt acgccaccgc aggcgctgcg   1320

cgcgcagggc ctcctgaaag aagcggagca tgttgagtca cagagcgcag aaaccgttct   1380

gactcccgac gaatgtcaac tcctgggcta tctggacaag gggaaacgta aacgtaaaga   1440

gaaagcaggc agcctccagt gggcatatat ggcgatcgca cggttaggag gcttcatgga   1500

cagcaaacgt acgggtattg cgagctgggg tgcgctgtgg gaaggctggg aagctttgca   1560

gagtaaactt gatggtttct tagccgcgaa ggatctgatg gcacagggga ttaaactcga   1620

gtaacggacg aacgcaaaca aacgtggatc cttcagctgt ctcttataca catctgaact   1680

agttgtaggc ctaaattcga actgatcctt caactcagca aaagttcgat ttattcaaca   1740

aagccacgtt gtgtctcaaa atctctgatg ttacattgca caagataaaa atatatcatc   1800

atgaacaata aaactgtctg cttacataaa cagtaataca aggggtgtta tgagccatat   1860

tcaacgggaa acgtcttgct ctaggccgcg attaaattcc aacatggatg ctgatttata   1920

tgggtataaa tgggctcgcg ataatgtcgg gcaatcaggt gcgacaatct atcgattgta   1980

tgggaagccc gatgcgccag agttgtttct gaaacatggc aaaggtagcg ttgccaatga   2040

tgttacagat gagatggtca gactaaactg gctgacggaa tttatgcctc ttccgaccat   2100

caagcatttt atccgtactc ctgatgatgc atggttactc accactgcga tccccgggaa   2160

aacagcattc caggtattag aagaatatcc tgattcaggt gaaaatattg ttgatgcgct   2220

ggcagtgttc ctgcgccggt tgcattcgat tcctgtttgt aattgtcctt ttaacagcga   2280

tcgcgtattt cgtctcgctc aggcgcaatc acgaatgaat aacggtttgg ttgatgcgag   2340

tgattttgat gacgagcgta atggctggcc tgttgaacaa gtctggaaag aaatgcataa   2400

gcttttgcca ttctcaccgg attcagtcgt cactcatggt gatttctcac ttgataacct   2460

tatttttgac gaggggaaat taataggttg tattgatgtt ggacgagtcg gaatcgcaga   2520

ccgataccag gatcttgcca tcctatggaa ctgcctcggt gagttttctc cttcattaca   2580

gaaacggctt tttcaaaaat atggtattga taatcctgat atgaataaat tgcagtttca   2640

tttgatgctc gatgagtttt tctaacacga tatcgtcaat tgctagatgt gtataagaga   2700

caggctggac aacgagagta gttacgtcct agg                                2733
```

<210> SEQ ID NO 7
<211> LENGTH: 2674
<212> TYPE: DNA
<213> ORGANISM: Alishewanella aestuarii

<400> SEQUENCE: 7

```
agatctccat cgaatggcca gatgattaat tcctaatttt tgttgacact ctatcattga     60

tagagttatt ttaccactcc ctatcagtga tagagaaaag tgaaatgaat agttcgacaa    120

aaatctagaa ataattttgt ttaactttat gatggagcta taccatggcc caccaccacc    180

accaccacca tatgaataat gcacagtggg cgaaatcgac gtttggtcag gccgacctcg    240

gggacccccg tcgtacaacg cgtttagtca agcttgccga aacacttgcc aacgatccgg    300

ggaaaccctt tgtctcgatt acccagagca aagccgatat ggaaggtgcc tatcgtttta    360
```

```
ttcgcaatga gcatgtgaat gctgatgcca ttgctaaagc cggctacctg gtgaccgcag    420
cacaagctgc gaagcataat ctgcttctgg cacttgaaga taccacggcc atcacctatt    480
cccaccgctc tgtgcgcgat gaactcggcc atgttaacca gggtaataat taccgtggca    540
ttcttgcaca ttccgtgctg ttgtttgccc cggaacagca agagctggtc ggactgattg    600
aacagagtcg ctggacccgt gatatttcaa cccgtggcaa aaagcatgtc cgtacacaaa    660
ctccgtatga agaaaaagaa agcttcaaat ggcagtctgc ttcagttaat ctgtcggcac    720
gtctgggcac caaaatggcg gacgtcatct cggtttgcga tcgtgaggcg gatatctacg    780
agtacctgca gtacaaactg tcaaaacagc atcgttttgt agtacgtagt atgcagtccc    840
gtcatatcga gcagtccgaa cagaagttgt acgattacgc cgcgggtttg gaatcggcag    900
ggcagaaaca aattcacatt gcgcagaaag gggccgcaa ggcgcgtacc gcaacagtcg    960
acattgtgtt tgccccggtg actttacagg tgccggcgaa taaacgtggt gaatccctct   1020
cgctgtacta cgtgggctgc gaagaacgcg ctgatgataa aaatgctttg aattggcacc   1080
tgctgaccac ggaacccgtc caatcaaaag cggacgcact gaacattatt cgctactatg   1140
aacaccggtg gctggtcgaa gaataccaca aagcctggaa aaccgacggt actgacattg   1200
agaacgctcg cctccaaagc aaagacaaca tcgagcgctt ggtaacgatc tcggcattca   1260
tcgctgttcg tatcgtccag ctgaaatttg cccgggaaca accggatgaa atcagttgtg   1320
aacaagttct ttctccgaag gcatggaaat tactgtggat taaacgtgtg agccgcacgt   1380
tgccggatac agtgccgtct atgaaatggg cctatactga attggctaaa ctgggagggt   1440
ggaaagatac caaacagacc ggtaaagcga gtgttaaggt cctctggcag ggttggttca   1500
aactgcaaac aatcttggaa ggctacgatc ttgccaaatc cttggaagcg gacttgctcg   1560
agtaacggac gaacgcaaac aaacgtggat ccttcagctg tctcttatac acatctgaac   1620
tagttgtagg cctaaattcg aactgatcct tcaactcagc aaaagttcga tttattcaac   1680
aaagccacgt tgtgtctcaa aatctctgat gttacattgc acaagataaa aatatatcat   1740
catgaacaat aaaactgtct gcttacataa acagtaatac aaggggtgtt atgagccata   1800
ttcaacggga aacgtcttgc tctaggccgc gattaaattc caacatggat gctgatttat   1860
atgggtataa atgggctcgc gataatgtcg ggcaatcagg tgcgacaatc tatcgattgt   1920
atgggaagcc cgatgcgcca gagttgtttc tgaaacatgg caaaggtagc gttgccaatg   1980
atgttacaga tgagatggtc agactaaact ggctgacgga atttatgcct cttccgacca   2040
tcaagcattt tatccgtact cctgatgatg catggttact caccactgcg atccccggga   2100
aaacagcatt ccaggtatta gaagaatatc ctgattcagg tgaaaatatt gttgatgcgc   2160
tggcagtgtt cctgcgccgg ttgcattcga ttcctgtttg taattgtcct tttaacagcg   2220
atcgcgtatt tcgtctcgct caggcgcaat cacgaatgaa taacggtttg gttgatgcga   2280
gtgattttga tgacgagcgt aatggctggc ctgttgaaca agtctggaaa gaaatgcata   2340
agcttttgcc attctcaccg gattcagtcg tcactcatgg tgatttctca cttgataacc   2400
ttatttttga cgaggggaaa ttaataggtt gtattgatgt tggacgagtc ggaatcgcag   2460
accgatacca ggatcttgcc atcctatgga actgcctcgg tgagttttct ccttcattac   2520
agaaacggct ttttcaaaaa tatggtattg ataatcctga tatgaataaa ttgcagtttc   2580
atttgatgct cgatgagttt ttctaacacg atatcgtcaa ttgctagatg tgtataagag   2640
acaggctgga caacgagagt agttacgtcc tagg                               2674
```

<210> SEQ ID NO 8
<211> LENGTH: 22
<212> TYPE: DNA
<213> ORGANISM: Alishewanella aestuarii

<400> SEQUENCE: 8
agatctccat cgaatggcca ga 22

<210> SEQ ID NO 9
<211> LENGTH: 27
<212> TYPE: DNA
<213> ORGANISM: Alishewanella aestuarii

<400> SEQUENCE: 9
cctaggacgt aactactctc gttgtcc 27

<210> SEQ ID NO 10
<211> LENGTH: 21
<212> TYPE: DNA
<213> ORGANISM: Alishewanella aestuarii

<400> SEQUENCE: 10
ctcgagtaac ggacgaacgc a 21

<210> SEQ ID NO 11
<211> LENGTH: 38
<212> TYPE: DNA
<213> ORGANISM: Alishewanella aestuarii

<400> SEQUENCE: 11
atacctacat gaattcagat ctccatcgaa tggccaga 38

<210> SEQ ID NO 12
<211> LENGTH: 46
<212> TYPE: DNA
<213> ORGANISM: Alishewanella aestuarii

<400> SEQUENCE: 12
aggccgttat gaattcccta ggacgtaact actctcgttg tccagc 46

<210> SEQ ID NO 13
<211> LENGTH: 19
<212> TYPE: DNA
<213> ORGANISM: Alishewanella aestuarii

<400> SEQUENCE: 13
tgatgcgctg gcagtgttc 19

<210> SEQ ID NO 14
<211> LENGTH: 22
<212> TYPE: DNA
<213> ORGANISM: Alishewanella aestuarii

<400> SEQUENCE: 14
cttgtgcaat gtaacatcag ag 22

<210> SEQ ID NO 15
<211> LENGTH: 23
<212> TYPE: DNA
<213> ORGANISM: Alishewanella aestuarii

<400> SEQUENCE: 15
atggtattga taatcctgat atg 23

<210> SEQ ID NO 16
<211> LENGTH: 476
<212> TYPE: PRT
<213> ORGANISM: Alishewanella aestuarii

<400> SEQUENCE: 16

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Leu Pro Gln Ala Leu Arg Ala Gln Gly Leu Leu Lys Glu
```

```
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475


<210> SEQ ID NO 17
<211> LENGTH: 477
<212> TYPE: PRT
<213> ORGANISM: Alishewanella aestuarii

<400> SEQUENCE: 17

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Gly Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270
```

Lys Gln Gly Asn Ile Thr Leu Asn Ala Val Leu Ala Glu Glu Ile Asn
275 280 285

Pro Pro Lys Gly Glu Thr Pro Leu Lys Trp Leu Leu Leu Thr Ser Glu
290 295 300

Pro Val Glu Ser Leu Ala Gln Ala Leu Arg Val Ile Asp Ile Tyr Thr
305 310 315 320

His Arg Trp Arg Ile Glu Glu Phe His Lys Ala Trp Lys Thr Gly Ala
325 330 335

Gly Ala Glu Arg Gln Arg Met Glu Glu Pro Asp Asn Leu Glu Arg Met
340 345 350

Val Ser Ile Leu Ser Phe Val Ala Val Arg Leu Leu Gln Leu Arg Glu
355 360 365

Ser Phe Thr Pro Pro Gln Ala Leu Arg Ala Gln Gly Leu Leu Lys Glu
370 375 380

Ala Glu His Val Glu Ser Gln Ser Ala Glu Thr Val Leu Thr Pro Asp
385 390 395 400

Glu Cys Gln Leu Leu Gly Tyr Leu Asp Lys Gly Lys Arg Lys Arg Lys
405 410 415

Glu Lys Ala Gly Ser Leu Gln Trp Ala Tyr Met Ala Ile Ala Arg Leu
420 425 430

Gly Gly Phe Met Asp Ser Lys Arg Thr Gly Ile Ala Ser Trp Gly Ala
435 440 445

Leu Trp Glu Gly Trp Glu Ala Leu Gln Ser Lys Leu Asp Gly Phe Leu
450 455 460

Ala Ala Lys Asp Leu Met Ala Gln Gly Ile Lys Leu Glu
465 470 475

<210> SEQ ID NO 18
<211> LENGTH: 477
<212> TYPE: PRT
<213> ORGANISM: Alishewanella aestuarii

<400> SEQUENCE: 18

Met Ile Thr Ser Ala Leu His Arg Ala Ala Asp Trp Ala Lys Ser Val
1 5 10 15

Phe Ser Ser Ala Ala Leu Gly Asp Pro Arg Arg Thr Ala Arg Leu Val
20 25 30

Asn Val Ala Ala Gln Leu Ala Lys Tyr Ser Gly Lys Ser Ile Thr Ile
35 40 45

Ser Ser Glu Gly Ser Lys Ala Ala Gln Glu Gly Ala Tyr Arg Phe Ile
50 55 60

Arg Asn Pro Asn Val Ser Ala Glu Ala Ile Arg Lys Ala Gly Ala Met
65 70 75 80

Gln Thr Val Lys Leu Ala Gln Glu Phe Pro Glu Leu Leu Ala Ile Glu
85 90 95

Asp Thr Thr Ser Leu Ser Tyr Arg His Gln Val Ala Glu Glu Leu Gly
100 105 110

Lys Leu Gly Ser Ile Gln Asp Lys Ser Arg Gly Trp Trp Val His Ser
115 120 125

Val Leu Leu Leu Glu Ala Thr Thr Phe Arg Thr Val Gly Leu Leu His
130 135 140

Gln Ala Trp Trp Met Arg Pro Asp Asp Pro Ala Asp Ala Asp Glu Lys
145 150 155 160

Glu Ser Gly Lys Trp Leu Ala Ala Ala Ala Thr Ser Arg Leu Arg Met
165 170 175

```
Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Leu Glu
465                 470                 475


<210> SEQ ID NO 19
<211> LENGTH: 477
<212> TYPE: PRT
<213> ORGANISM: Alishewanella aestuarii

<400> SEQUENCE: 19

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
```

```
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Cys Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Leu Glu
465                 470                 475

<210> SEQ ID NO 20
```

```
<211> LENGTH: 477
<212> TYPE: PRT
<213> ORGANISM: Alishewanella aestuarii

<400> SEQUENCE: 20

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Asn Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
```

385 390 395 400

Glu Cys Gln Leu Leu Gly Tyr Leu Asp Lys Gly Lys Arg Lys Arg Lys
405 410 415

Glu Lys Ala Gly Ser Leu Gln Trp Ala Tyr Met Ala Ile Ala Arg Leu
420 425 430

Gly Gly Phe Met Asp Ser Lys Arg Thr Gly Ile Ala Ser Trp Gly Ala
435 440 445

Leu Trp Glu Gly Trp Glu Ala Leu Gln Ser Lys Leu Asp Gly Phe Leu
450 455 460

Ala Ala Lys Asp Leu Met Ala Gln Gly Ile Lys Leu Glu
465 470 475

<210> SEQ ID NO 21
<211> LENGTH: 477
<212> TYPE: PRT
<213> ORGANISM: Alishewanella aestuarii

<400> SEQUENCE: 21

Met Ile Thr Ser Ala Leu His Arg Ala Ala Asp Trp Ala Lys Ser Val
1 5 10 15

Phe Ser Ser Ala Ala Leu Gly Asp Pro Arg Arg Thr Ala Arg Leu Val
20 25 30

Asn Val Ala Ala Gln Leu Ala Lys Tyr Ser Gly Lys Ser Ile Thr Ile
35 40 45

Ser Ser Glu Gly Ser Lys Ala Ala Gln Glu Gly Ala Tyr Arg Phe Ile
50 55 60

Arg Asn Pro Asn Val Ser Ala Glu Ala Ile Arg Lys Ala Gly Ala Met
65 70 75 80

Gln Thr Val Lys Leu Ala Gln Glu Phe Pro Glu Leu Leu Ala Ile Glu
85 90 95

Asp Thr Thr Ser Leu Ser Tyr Arg His Gln Val Ala Glu Glu Leu Gly
100 105 110

Lys Leu Gly Ser Ile Gln Asp Lys Ser Arg Gly Trp Trp Val His Ser
115 120 125

Val Leu Leu Leu Glu Ala Thr Thr Phe Arg Thr Val Gly Leu Leu His
130 135 140

Gln Ser Trp Trp Met Arg Pro Asp Asp Pro Ala Asp Ala Asp Glu Lys
145 150 155 160

Glu Ser Gly Lys Trp Leu Ala Ala Ala Ala Thr Ser Arg Leu Arg Met
165 170 175

Gly Ser Met Met Ser Asn Val Ile Ala Val Cys Asp Arg Glu Ala Asp
180 185 190

Ile His Ala Tyr Leu Gln Asp Lys Leu Ala His Asn Glu Arg Phe Val
195 200 205

Val Arg Ser Lys His Pro Arg Lys Asp Val Glu Ser Gly Leu Tyr Leu
210 215 220

Tyr Asp His Leu Lys Asn Gln Pro Glu Leu Gly Gly Tyr Gln Ile Ser
225 230 235 240

Ile Pro Gln Lys Gly Val Val Asp Lys Arg Gly Lys Arg Lys Asn Arg
245 250 255

Pro Ala Arg Lys Ala Ser Leu Ser Leu Arg Ser Gly Arg Ile Thr Leu
260 265 270

Lys Gln Gly Asn Ile Thr Leu Asn Ala Val Leu Ala Glu Glu Ile Asn
275 280 285

```
Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Leu Glu
465                 470                 475


<210> SEQ ID NO 22
<211> LENGTH: 477
<212> TYPE: PRT
<213> ORGANISM: Alishewanella aestuarii

<400> SEQUENCE: 22

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
                165                 170                 175

Gly Ser Met Met Ser Asn Val Ile Ala Val Cys Asp Arg Glu Ala Asp
            180                 185                 190
```

```
Ile His Ala Tyr Leu Gln Asp Lys Leu Ala His Asn Glu Arg Phe Val
        195                 200                 205

Val Arg Ser Lys His Ser Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Leu Glu
465                 470                 475


<210> SEQ ID NO 23
<211> LENGTH: 477
<212> TYPE: PRT
<213> ORGANISM: Alishewanella aestuarii

<400> SEQUENCE: 23

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
```

-continued

```
            85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Ser Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Ala Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Leu Glu
465                 470                 475
```

METHODS OF SCREENING TRANSPOSASES BY EMPLOYING TRANSPOSASES TO INDUCE TRANSPOSITION OF OLIGONUCLEOTIDES COMPRISING END SEQUENCES TO GENERATE INSERTION SITES FOR SEQUENCING

CROSS REFERENCE TO RELATED APPLICATIONS

This application is the U.S. national phase application under 35 U.S.C. § 371 of International Patent Application No. PCT/US2018/048823, filed Aug. 30, 2018, which claims the benefit of U.S. provisional application USSN 62/552,214, filed Aug. 30, 2017, the contents of which are herein incorporated by reference in their entireties.

INCORPORATION OF SEQUENCE LISTING

The contents of the text file named "RMSI-010_001WO SeqListing_ST25.txt", which was created Aug. 28, 2018 and is 60.4 KB in size, are hereby incorporated by reference in their entirety.

FIELD OF THE DISCLOSURE

The disclosure is directed towards the field of molecular biology; and, more specifically molecular tools to enable the fast and efficient high-throughput screening of mutant and mutagenized transposases.

BACKGROUND

There have been long-felt but unmet needs in the art for molecular tools to enable the fast and efficient high-throughput screening of mutant and mutagenized transposases to identify rare mutations that lead to desired features to the use of transposases as molecular tools. The disclosure provides a system and methods to solve these long-felt but unmet needs.

SUMMARY

The disclosure provides a method of screening a plurality of transposases, comprising: (a) contacting a first transposase with a first nucleic acid sample under conditions sufficient to induce transposition of a first oligonucleotide comprising a first end sequence, thereby generating a first transposed nucleic acid sample having a first plurality of insertion sites of the first end sequence; (b) contacting a second transposase with a second nucleic acid sample under conditions sufficient to induce transposition of a second oligonucleotide comprising a second end sequence, thereby generating a second transposed nucleic acid sample, the second transposase having an amino acid sequence different from the first transposase by at least one amino acid having a second plurality of insertion sites; (c) sequencing at least a portion of the first plurality of insertion sites of the first transposed nucleic acid sample, thereby generating a first set of sequencing reads, each of the first set of sequencing reads comprising one of the insertion sites of the first end sequence; (d) sequencing at least a portion of the second plurality of insertion sites of the second transposed nucleic acid sample, thereby generating a second set of sequencing reads, each of the second set of sequencing reads comprising one of the insertion sites of the second end sequence; (e) comparing the first set of sequencing reads with the second set of sequencing reads; and (f) assigning a probability that the second transposase is significantly different from the first transposase based on the step (e) of comparing.

In some embodiments of the methods of screening a plurality of transposases of the disclosure, step (e) of comparing comprises: calculating the frequency of each possible nucleotide base at each nucleotide position for the first set of sequencing reads, thereby generating a first set of frequency values; calculating the frequency of each possible nucleotide base at each nucleotide position for the second set of sequencing reads, thereby generating a second set of frequency values; calculating an absolute difference between the first set of frequency values and the second set of frequency values for each possible nucleotide base at each nucleotide position, thereby generating a set of absolute difference values; and averaging each of the absolute difference values, thereby determining an inter-motif distance.

In some embodiments of the methods of screening a plurality of transposases of the disclosure, step (e) of comparing comprises: measuring or determining the frequency of each possible nucleotide base at each nucleotide position for the first set of sequencing reads, thereby generating a first set of frequency values; measuring or determining the frequency of each possible nucleotide base at each nucleotide position for the second set of sequencing reads, thereby generating a second set of frequency values; measuring or determining an absolute difference between the first set of frequency values and the second set of frequency values for each possible nucleotide base at each nucleotide position, thereby generating a set of absolute difference values; and averaging each of the absolute difference values, thereby determining an inter-motif distance.

In some embodiments of the methods of screening a plurality of transposases of the disclosure, step (f) of assigning comprises: generating an inter-motif distance probability plot defined by simulated random sequence reads; and assigning the probability value that the second transposase is significantly different from the first transposase based on each of the inter-motif distance determined in the step (e) and the inter-motif distance probability plot.

In some embodiments of the methods of screening a plurality of transposases of the disclosure, step (e) of comparing comprises: calculating a first sequencing depth of coverage at segments of defined length within a first reference nucleic acid sample at positions corresponding to the first plurality of insertion sites in the first transposed nucleic acid sample; calculating a second sequencing depth of coverage at segments of defined length within a first reference nucleic acid sample at positions corresponding to the second plurality of insertion sites in the second transposed nucleic acid sample; and comparing the first sequencing depth of coverage with the second sequencing depth of coverage.

In some embodiments of the methods of screening a plurality of transposases of the disclosure, step (e) of comparing comprises: measuring or determining a first sequencing depth of coverage at segments of defined length within a first reference nucleic acid sample at positions corresponding to the first plurality of insertion sites in the first transposed nucleic acid sample; measuring or determining a second sequencing depth of coverage at segments of defined length within a first reference nucleic acid sample at positions corresponding to the second plurality of insertion sites in the second transposed nucleic acid sample; and comparing the first sequencing depth of coverage with the second sequencing depth of coverage.

In some embodiments of the methods of screening a plurality of transposases of the disclosure, step (f) of assigning comprises: performing at least one of a Mann-Whitney test for differences in means, a Kolmogorov-Smirnoff test for different distribution shapes, a parametric test, a non-parametric test, a visual inspection of shape differences, and a percentile-based metric calculation.

In some embodiments of the methods of screening a plurality of transposases of the disclosure, step (e) of comparing comprises: calculating a first fractional GC content for a nucleic acid segment of a defined length in a first reference nucleic acid sample at positions corresponding to the first plurality of insertion sites in the first transposed nucleic acid sample; calculating a second fractional GC content for a nucleic acid segment of a defined length in the first reference nucleic acid sample at positions corresponding to the second insertion sites in the second transposed nucleic acid sample; and identifying a difference between the first fractional GC content and the second fractional GC content.

In some embodiments of the methods of screening a plurality of transposases of the disclosure, step (e) of comparing comprises: measuring or determining a first fractional GC content for a nucleic acid segment of a defined length in a first reference nucleic acid sample at positions corresponding to the first plurality of insertion sites in the first transposed nucleic acid sample; measuring or determining a second fractional GC content for a nucleic acid segment of a defined length in the first reference nucleic acid sample at positions corresponding to the second insertion sites in the second transposed nucleic acid sample; and identifying a difference between the first fractional GC content and the second fractional GC content.

In some embodiments of the methods of screening a plurality of transposases of the disclosure, step (f) of assigning comprises: performing at least one of a Mann-Whitney test for differences in means, a Kolmogorov-Smirnoff test for different distribution shapes, a parametric test, a non-parametric test, a visual inspection of shape differences, and a percentile-based metric calculation.

The disclosure provides a composition comprising a nucleic acid comprising from 5' to 3', (a) a first transposon end sequence, (b) a unique identifier (UID) barcode, and (c) a second transposon end sequence, wherein the nucleic acid is capable of transposition, and a unique nucleic acid sequence encoding a transposase. In certain embodiments, the nucleic acid comprising from 5' to 3' further comprises a selectable marker located between the unique identifier (UID) barcode and the second transposon end sequence. In certain embodiments, the UID barcode is associated with the unique nucleic acid sequence encoding the transposase.

In certain embodiments of the compositions of the disclosure, the nucleic acid comprising elements (a) through (c) does not comprise the unique nucleic acid sequence encoding the transposase. In certain embodiments, a first vector comprises the nucleic acid comprising elements (a) through (c) and a second vector comprises the unique nucleic acid sequence encoding the transposase.

In certain embodiments of the compositions of the disclosure, the nucleic acid comprising elements (a) through (c) further comprises the unique nucleic acid sequence encoding the transposase. In certain embodiments, the unique nucleic acid sequence encoding the transposase is located 5' of the first transposon end sequence. In certain embodiments, a vector comprises the nucleic acid comprising elements (a) through (c) and the unique nucleic acid sequence encoding the transposase.

In certain embodiments of the compositions of the disclosure, the UID barcode comprises between 5 and 200 base pairs, inclusive of the endpoints. In certain embodiments, the UID barcode comprises between 10 and 100 base pairs, inclusive of the endpoints. In certain embodiments, the UID barcode comprises between 10 and 50 base pairs, inclusive of the endpoints. In certain embodiments, the UID barcode comprises between 15 and 25 base pairs, inclusive of the endpoints.

In certain embodiments of the compositions of the disclosure, the UID barcode is correlated with the unique nucleic acid sequence encoding the transposase. As used herein the term correlated is meant to describe a record in a database by which a nucleic acid sequence of the UID barcode is matched with a unique nucleic acid sequence encoding a transposase. In certain embodiments of the methods of the disclosure, the UID barcode and the unique nucleic acid sequence encoding the transposase may be sequenced prior to initiating the method. Moreover, in certain embodiments of the methods of the disclosure, the UID barcode and the unique nucleic acid sequence encoding the transposase may be correlated prior to initiating the method.

In certain embodiments of the compositions of the disclosure, the transposase is a wild type transposase. In certain embodiments, the wild type transposase is isolated or derived from any species.

In certain embodiments of the compositions of the disclosure, the transposase is a wild type transposase. In certain embodiments, the wild type transposase is a wild-type TnAa-transposase. In certain embodiments, the wild-type TnAa-transposase comprises the amino acid sequence of SEQ ID NO: 2.

In certain embodiments of the compositions of the disclosure, the transposase is a wild type transposase. In certain embodiments, the wild type transposase is a wild-type Tn5-transposase. In certain embodiments, the wild type Tn5-transposase comprises the amino acid sequence of SEQ ID NO: 17.

In certain embodiments of the compositions of the disclosure, the transposase is a mutant transposase. In certain embodiments, the mutant transposase has an increased transposase activity relative to the wild type transposase. In certain embodiments, the mutant transposase has a reduced insertion site bias compared to the wild type transposase. In certain embodiments, the mutant transposase comprises at least one known or naturally-occurring mutation.

In certain embodiments of the compositions of the disclosure, the transposase is a mutant transposase. In certain embodiments, the mutant transposase comprises at least one known or naturally-occurring mutation. In certain embodiments, the mutant transposase is a mutant TnAa-transposase. In certain embodiments, the mutant transposase is a mutant Tn5-transposase.

In certain embodiments of the compositions of the disclosure, the transposase is a mutant transposase. In certain embodiments, the mutant transposase is a mutant TnAa-transposase. In certain embodiments, the mutant TnAa-transposase comprises P47K or M50A. In certain embodiments, the mutant TnAa-transposase comprises P47K. In certain embodiments, including those in which the mutant TnAa-transposase comprises P47K, the mutant TnAa-transposase comprises the amino acid sequence of SEQ ID NO: 5. In certain embodiments, the mutant TnAa-transposase comprises M50A. In certain embodiments, including those in which the mutant TnAa-transposase comprises M50A, the mutant TnAa-transposase comprises the amino acid sequence of SEQ ID NO: 4. In certain embodiments, the mutant TnAa-transposase comprises P47K and M50A. In certain embodiments, including those in which the mutant TnAa-transposase comprises P47K and M50A, the mutant TnAa-transposase comprises the amino acid sequence of SEQ ID NO: 3.

In certain embodiments of the compositions of the disclosure, the transposase is a mutant transposase. In certain embodiments, the mutant transposase comprises a mutation at a position that is functionally equivalent to a mutation in a Tn5-transposase at position 30, 40, 41, 47, 54, 56, 62, 97, 110, 188, 212, 319, 322, 326, 330, 333, 342, 344, 345, 348, 372, 438, 445, 462, or 466 of the sequence according to SEQ ID NO: 17.

In certain embodiments, the mutant transposase is a mutant Tn5-transposase. Mutant Tn5-transposases of the disclosure may include, but are not limited to, the mutations provided at, for example, uniprot.org/uniprot/Q46731. In certain embodiments, the mutant Tn5-transposase comprises a mutation at position 30, 40, 41, 47, 54, 56, 62, 97, 110, 188, 212, 319, 322, 326, 330, 333, 342, 344, 345, 348, 372, 438, 445, 462, or 466 of the sequence according to SEQ ID NO: 17. In certain embodiments, the mutant Tn5-transposase comprises R30Q, K40Q, Y41H, T47P, E54K, E54V, M56A, R62Q, D97A, E110K, D188A, K212M, Y319A, R322A, R322K, E326A, K330A, K330R, K333A, K333R, R342A, R344A, E345K, N348A, L372P, S438A, K438A, S445A, G462D or A466D of the sequence according to SEQ ID NO: 17. In certain embodiments, the mutant Tn5-transposase comprises a mutation that decreases transposase activity compared to a wild type transposase, including, but not limited to, R30Q, K40Q, R62Q, D97A, E326A, K330A, and S445A of the sequence according to SEQ ID NO: 17. In certain embodiments, the mutant Tn5-transposase comprises a mutation that increases transposase activity compared to a wild type transposase, including, but not limited to, R62Q, D97A, E110K, D188A, and L372P of the sequence according to SEQ ID NO: 17. In certain embodiments, the mutant Tn5-transposase comprises a mutation that decreases DNA cleavage activity compared to a wild type transposase, including, but not limited to, K333A and K333R of the sequence according to SEQ ID NO: 17. In certain embodiments, the mutant Tn5-transposase comprises a mutation that decreases strand transfer activity compared to a wild type transposase, including, but not limited to, Y319A, R322A, R322K, K333A and K333R of the sequence according to SEQ ID NO: 17. In certain embodiments, the mutant Tn5-transposase comprises a mutation that increases transposition frequency compared to a wild type transposase, including, but not limited to, Y41H, T47P, E54K and E54V of the sequence according to SEQ ID NO: 17. In certain embodiments, the mutant Tn5-transposase comprises a mutation that abolishes expression of a transposase inhibitor, including, but not limited to, M56A of the sequence according to SEQ ID NO: 17. In certain embodiments, the mutant Tn5-transposase comprises E54K, M56A or L372P of the sequence according to SEQ ID NO: 17. In certain embodiments, the mutant Tn5-transposase comprises E54K, M56A and L372P (also referred to herein as a "hyperactive Tn5-transposase) of the sequence according to SEQ ID NO: 17. In certain embodiments, including those in which the mutant Tn5-transposase comprises E54K, M56A and L372P of the sequence according to SEQ ID NO: 17, the mutant Tn5-transposase comprises the amino acid sequence of SEQ ID NO: 1. In certain embodiments, the mutant Tn5-transposase comprises a mutation that decreases target specificity compared to a wild type transposase, including, but not limited to K212M of the sequence according to SEQ ID NO: 17.

In certain embodiments of the compositions of the disclosure, the transposase is a mutagenized transposase. In certain embodiments, the unique nucleic acid sequence encoding the mutagenized transposase or a sequence encoding the mutagenized transposase has been (a) exposed to a mutagen or (b) subjected to random mutagenesis, site-directed mutagenesis, or a combination thereof. In certain embodiments, the mutagen is a physical mutagen. In certain embodiments, the physical mutagen is ionizing radiation. In certain embodiments, the physical mutagen is ultraviolet radiation. In certain embodiments, the mutagen is a chemical mutagen. In certain embodiments, the chemical mutagen is a reactive oxygen species, a metal, a deaminating agent or an alkylating agent.

In certain embodiments of the compositions of the disclosure, the transposase is a mutagenized transposase. In certain embodiments, the unique nucleic acid sequence encoding the mutagenized transposase or a sequence encoding the mutagenized transposase has been (a) exposed to a mutagen or (b) subjected to random mutagenesis, site-directed mutagenesis, or a combination thereof. In certain embodiments, the random mutagenesis comprises (a) contacting a sequence encoding the mutagenized transposase with a physical mutagen and/or a chemical mutagen, (b) subjecting the sequence encoding the mutagenized transposase to error-prone polymerase chain reaction (PCR), or (C) a combination of (a) and (b). In certain embodiments, the site-directed mutagenesis comprises alanine-scanning. In certain embodiments, the physical mutagen is ultraviolent radiation. In certain embodiments, the chemical mutagen comprises an alkylating agent. In certain embodiments, the alkylating agent comprises N-ethyl-N-nitrosourea (ENU). In certain embodiments, the chemical mutagen comprises ethyl methanesulfonate (EMS).

In certain embodiments of the compositions of the disclosure, the transposase is a mutagenized transposase. In certain embodiments, the unique nucleic acid sequence encoding the mutagenized transposase or the sequence encoding the mutagenized transposase that has been mutagenized is a sequence encoding a wild type transposase. In certain embodiments, the sequence encoding a wild type transposase or the wild type transposase is isolated or derived from any species.

In certain embodiments of the compositions of the disclosure, the transposase is a mutagenized transposase. In certain embodiments, the unique nucleic acid sequence encoding the mutagenized transposase or the sequence encoding the mutagenized transposase that has been mutagenized is a sequence encoding a wild type transposase. In certain embodiments, the sequence encoding a wild type transposase or the wild type transposase is isolated or derived from any species. In certain embodiments, the wild type transposase is a wild-type TnAa-transposase. In certain embodiments, including those in which the wild type transposase is a wild-type TnAa-transposase, the wild-type TnAa-transposase comprises the amino acid sequence of SEQ ID NO: 2.

In certain embodiments of the compositions of the disclosure, the transposase is a mutagenized transposase. In certain embodiments, the unique nucleic acid sequence encoding the mutagenized transposase or the sequence encoding the mutagenized transposase that has been mutagenized is a sequence encoding a wild type transposase. In certain embodiments, the sequence encoding a wild type transposase or the wild type transposase is isolated or derived from any species. In certain embodiments, the wild type transposase is a wild-type Tn5-transposase. In certain embodiments, including those in which the wild type transposase is a wild-type Tn5-transposase, the wild type Tn5-transposase comprises the amino acid sequence of SEQ ID NO: 17.

In certain embodiments of the compositions of the disclosure, the transposase is a mutagenized transposase. In certain embodiments, the unique nucleic acid sequence encoding the mutagenized transposase or the sequence encoding the mutagenized transposase that has been mutagenized is a sequence encoding a mutant transposase. In certain embodiments, the sequence encoding a mutant transposase or the mutant transposase is isolated or derived from any species. In certain embodiments, the mutant transposase comprises at least one non-naturally occurring mutation.

In certain embodiments of the compositions of the disclosure, the transposase is a mutagenized transposase. In certain embodiments, the unique nucleic acid sequence encoding the mutagenized transposase or the sequence encoding the mutagenized transposase that has been mutagenized is a sequence encoding a mutant transposase. In certain embodiments, the sequence encoding a mutant transposase or the mutant transposase is isolated or derived from any species. In certain embodiments, prior to mutagenesis, the mutant transposase has an increased transposase activity relative to the wild type transposase. In certain embodiments, prior to mutagenesis, the mutant transposase has a reduced insertion site bias compared to the wild type transposase. In certain embodiments, prior to mutagenesis, the mutant transposase comprises at least one known or naturally-occurring mutation. In certain embodiments, prior to mutagenesis, the mutant transposase is a mutant TnAa-transposase. In certain embodiments, prior to mutagenesis, the mutant transposase is a mutant Tn5-transposase.

In certain embodiments of the compositions of the disclosure, the transposase is a mutagenized transposase. In certain embodiments, the unique nucleic acid sequence encoding the mutagenized transposase or the sequence encoding the mutagenized transposase that has been mutagenized is a sequence encoding a mutant transposase. In certain embodiments, the sequence encoding a mutant transposase or the mutant transposase is isolated or derived from any species. In certain embodiments, the mutant transposase is a mutant TnAa-transposase. In certain embodiments, the mutant TnAa-transposase comprises P47K or M50A. In certain embodiments, the mutant TnAa-transposase comprises P47K. In certain embodiments, including those in which the mutant TnAa-transposase comprises P47K, the mutant TnAa-transposase comprises the amino acid sequence of SEQ ID NO: 5. In certain embodiments, the mutant TnAa-transposase comprises M50A. In certain embodiments, including those in which the mutant TnAa-transposase comprises M50A, the mutant TnAa-transposase comprises the amino acid sequence of SEQ ID NO: 4. In certain embodiments, the mutant TnAa-transposase comprises P47K and M50A. In certain embodiments, including those in which the mutant TnAa-transposase comprises P47K and M50A, the mutant TnAa-transposase comprises the amino acid sequence of SEQ ID NO: 3.

In certain embodiments of the compositions of the disclosure, the transposase is a mutagenized transposase. In certain embodiments, the unique nucleic acid sequence encoding the mutagenized transposase or the sequence encoding the mutagenized transposase that has been mutagenized is a sequence encoding a mutant transposase. In certain embodiments, the sequence encoding a mutant transposase or the mutant transposase is isolated or derived from any species. In certain embodiments, the mutant transposase comprises a mutation at a position that is functionally equivalent to a mutation in a Tn5-transposase at position 30, 40, 41, 47, 54, 56, 62, 97, 110, 188, 212, 319, 322, 326, 330, 333, 342, 344, 345, 348, 372, 438, 445, 462, or 466 of the sequence according to SEQ ID NO: 17.

In certain embodiments of the compositions of the disclosure, the transposase is a mutagenized transposase. In certain embodiments, the unique nucleic acid sequence encoding the mutagenized transposase or the sequence encoding the mutagenized transposase that has been mutagenized is a sequence encoding a mutant transposase. In certain embodiments, the sequence encoding a mutant transposase or the mutant transposase is isolated or derived from any species. In certain embodiments, the mutant transposase is a mutant Tn5-transposase. Mutant Tn5-transposases of the disclosure may include, but are not limited to, the mutations provided at, for example, uniprot.org/uniprot/Q46731. In certain embodiments, the mutant Tn5-transposase comprises a mutation at position 30, 40, 41, 47, 54, 56, 62, 97, 110, 188, 212, 319, 322, 326, 330, 333, 342, 344, 345, 348, 372, 438, 445, 462, or 466 of the sequence according to SEQ ID NO: 17. In certain embodiments, the mutant Tn5-transposase comprises R30Q, K40Q, Y41H, T47P, E54K, E54V, M56A, R62Q, D97A, E110K, D188A, K212M, Y319A, R322A, R322K, E326A, K330A, K330R, K333A, K333R, R342A, R344A, E345K, N348A, L372P, S438A, K438A, S445A, G462D or A466D of the sequence according to SEQ ID NO: 17. In certain embodiments, the mutant Tn5-transposase comprises a mutation that decreases transposase activity compared to a wild type transposase, including, but not limited to, R30Q, K40Q, R62Q, D97A, E326A, K330A, and S445A of the sequence according to SEQ ID NO: 17. In certain embodiments, the mutant Tn5-transposase comprises a mutation that increases transposase activity compared to a wild type transposase, including, but not limited to, R62Q, D97A, E110K, D188A, and L372P of the sequence according to SEQ ID NO: 17. In certain embodiments, the mutant Tn5-transposase comprises a mutation that decreases DNA cleavage activity compared to a wild type transposase, including, but not limited to, K333A and K333R of the sequence according to SEQ ID NO: 17. In certain embodiments, the mutant Tn5-transposase comprises a mutation that decreases strand transfer activity compared to a wild type transposase, including, but not limited to, Y319A, R322A, R322K, K333A and K333R of the sequence according to SEQ ID NO: 17. In certain embodiments, the mutant Tn5-transposase comprises a mutation that increases transposition frequency compared to a wild type transposase, including, but not limited to, Y41H, T47P, E54K and E54V of the sequence according to SEQ ID NO: 17. In certain embodiments, the mutant Tn5-transposase comprises a mutation that abolishes expression of a transposase inhibitor, including, but not limited to, M56A of the sequence according to SEQ ID NO: 17. In certain embodiments, the mutant Tn5-transposase comprises E54K, M56A or L372P of the sequence according to SEQ ID NO: 17. In certain embodiments, the mutant Tn5-transposase comprises E54K, M56A and L372P of the sequence according to SEQ ID NO: 17 (also referred to herein as a "hyperactive Tn5-transposase). In certain embodiments, including those in which the mutant Tn5-transposase comprises E54K, M56A and L372P of the sequence according to SEQ ID NO: 17, the mutant Tn5-transposase comprises the amino acid sequence of SEQ ID NO: 1. In certain embodiments, the mutant Tn5-transposase comprises a mutation that decreases target specificity compared to a wild type transposase, including, but not limited to K212M of the sequence according to SEQ ID NO: 17.

In certain embodiments of the compositions of the disclosure, the selectable marker is an antibiotic resistance gene. Exemplary antibiotic resistance genes of the disclosure confer resistance an antibiotic including, but are not limited to, kanamycin, spectinomycin, streptomycin, ampicillin, carbenicillin, bleomycin, erythromycin, polymyxin B, tetracycline, and neomycin. Additional antibiotic resistance genes of the disclosure may be found at, for example, ardb.cbcb.umd.edu/browsegene.shtml).

The disclosure provides a vector comprising a composition of the disclosure.

The disclosure provides a cell comprising a composition of the disclosure. The disclosure provides a cell comprising vector of the disclosure that comprises a composition of the disclosure. In certain embodiments, the cell is a bacterial cell. In certain embodiments, the cell is a yeast cell.

The disclosure provides a method of screening a plurality of transposases, comprising: (a) introducing a plurality of compositions of the disclosure into a plurality of cells under conditions suitable for at least one cell of the plurality of cells is transformed by at least one composition of the plurality of compositions, wherein the plurality of transposases comprise wild type, mutant or mutagenized forms of the at least one transposase; (b) expressing at least one transposase of the plurality of transposases under conditions sufficient to induce transposition of a nucleic acid comprising the first end sequence, the UID barcode, the selectable marker and the second transposon end sequence; (c) sequencing a nucleic acid sequence at an insertion site of the transposed nucleic acid in (b) comprising an insertion site repeat, the first end sequence and the UID barcode; (d) generating an insertion site consensus sequence for each transposase of the plurality of transposases, and (e) selecting a first transposase having an insertion site consensus sequence that is distinct from an insertion site consensus sequence of a second transposase.

In certain embodiments of the methods of the disclosure, the first transposase of (e) is a mutagenized transposase and the second transposase of (e) is a wild type form of the same transposase. In certain embodiments, the first transposase of (e) is a mutagenized transposase and the second transposase of (e) is a mutant form of the same transposase. In certain embodiments, the first transposase of (e) is a mutagenized transposase and the second transposase of (e) is a mutagenized form of the same transposase.

In certain embodiments of the methods of the disclosure, the first transposase of (e) is a wild type transposase and the second transposase of (e) is a wild type transposase.

In certain embodiments of the methods of the disclosure, the expressing step (b) comprises expressing each transposase of the plurality of transposases under conditions sufficient to induce transposition of a nucleic acid comprising the first end sequence, the UID barcode, the selectable marker and the second transposon end sequence.

In certain embodiments of the methods of the disclosure, the expressing step (b) comprises transiently expressing the at least one transposase of the plurality of transposases under conditions sufficient to induce transposition of a nucleic acid comprising the first end sequence, the UID barcode, the selectable marker and the second transposon end sequence. In certain embodiments, the expressing step (b) comprises transiently expressing the each transposase of the plurality of transposases under conditions sufficient to induce transposition of a nucleic acid comprising the first end sequence, the UID barcode, the selectable marker and the second transposon end sequence.

In certain embodiments of the methods of the disclosure, the plurality of cells comprises a plurality of bacterial cells.

In certain embodiments of the methods of the disclosure, the plurality of transposases comprises at least 100 transposases and wherein each transposase of the plurality of transposases is encoded by a unique nucleic acid sequence. In certain embodiments, the plurality of transposases comprises at least 500 transposases and wherein each transposase of the plurality of transposases is encoded by a unique nucleic acid sequence. In certain embodiments, the plurality of transposases comprises at least 1000 transposases and wherein each transposase of the plurality of transposases is encoded by a unique nucleic acid sequence. In certain embodiments, the plurality of transposases comprises at least 5000 transposases and wherein each transposase of the plurality of transposases is encoded by a unique nucleic acid sequence. In certain embodiments, the plurality of transposases comprises at least 10,000 transposases and wherein each transposase of the plurality of transposases is encoded by a unique nucleic acid sequence.

In certain embodiments of the methods of the disclosure, a vector comprises each composition of the plurality of compositions. In certain embodiments, the vector comprises a plasmid, an expression vector, or a viral vector. In certain embodiments, the vector does not replicate inside the cell. In certain embodiments, the vector comprises a constitutive promoter and the composition is under control of the constitutive promoter.

In certain embodiments of the methods of the disclosure, the plurality of transposases comprises two or more wild type transposases.

In certain embodiments of the methods of the disclosure, the plurality of transposases comprises two or more of wild type, mutant and mutagenized forms of the same transposase. In certain embodiments, the plurality of transposases comprises wild type and mutagenized forms of the same transposase. In certain embodiments, the plurality of transposases comprises wild type, mutant and mutagenized forms of the same transposase.

In certain embodiments of the methods of the disclosure, the sequencing is next generation sequencing (NGS).

In certain embodiments of the methods of the disclosure, the method further comprises the step of analyzing at least one feature of the selected first transposase of (e).

In certain embodiments of the methods of the disclosure, the method further comprises the step of analyzing at least one feature of the selected first transposase of (e). In certain embodiments, the analyzing comprises: (a) inducing transposition of a nucleic acid comprising a first end sequence, a UID barcode, and a second transposon end sequence, wherein the transposition is mediated by the selected mutagenized transposase of (e) and the UID barcode is associated with the selected first transposase of (e), (b) inducing transposition of a nucleic acid comprising a first end sequence, a UID barcode, and a second transposon end sequence, wherein the transposition is mediated by a wild type form of the selected mutagenized transposase of (e) and the UID barcode is associated with the second transposase, (c) measuring either a transposase activity or the transposition frequency of each of the selected first transposase of (e) and the second transposase, and (d) identifying the selected first transposase of (e) as having increased transposase activity and/or increased transposition frequency compared to the second transposase or (e) identifying the selected first transposase of (e) as having decreased transposase activity and/or decreased transposition frequency compared to the second transposase. In certain embodiments, the selected first transposase is a hyperactive transposase.

In certain embodiments of the methods of the disclosure, the method further comprises the step of analyzing at least one feature of the selected first transposase of (e). In certain embodiments, the analyzing comprises: (a) aligning the insertion site consensus sequence of the selected first transposase of (e) with an insertion site consensus sequence of the second transposase of (e) and (b) identifying the selected first transposase of (e) as having a decreased insertion site bias compared to the second transposase when the insertion site consensus sequence of the selected first transposase contains a greater number of variable positions or (c) identifying the selected first transposase of (e) as having an increased insertion site bias compared to the second transposase when the insertion site consensus sequence of the selected first transposase contains a lesser number of variable positions.

In certain embodiments of the methods of the disclosure, the method further comprises the step of analyzing at least one feature of the selected first transposase of (e). In certain embodiments, the analyzing comprises: (a) aligning the insertion site consensus sequence of the selected first transposase of (e) with an insertion site consensus sequence of the second transposase of (e) and (b) identifying the selected first transposase of (e) as having a decreased insertion site bias compared to the second transposase when the insertion site consensus sequence of the selected first transposase contains an increased sequence variation at one or more positions or (c) identifying the selected first transposase of (e) as having an increased insertion site bias compared to the second transposase when the insertion site consensus sequence of the selected first transposase contains a decreased sequence variation at one or more positions.

In certain embodiments of the methods of the disclosure, the method further comprises the step of analyzing at least one feature of the selected first transposase of (e). In certain embodiments, the analyzing comprises: (a) aligning the insertion site consensus sequence of the selected first transposase of (e) with an insertion site consensus sequence of the second transposase of (e) and (b) identifying the selected first transposase of (e) as having an increased insertion site bias compared to the second transposase when the insertion site consensus sequence of the selected first transposase contains a decreased sequence variation at one or more positions or (c) identifying the selected first transposase of (e) as having a decreased insertion site bias compared to the second transposase when the insertion site consensus sequence of the selected first transposase contains an increased sequence variation at one or more positions.

In certain embodiments of the methods of the disclosure, including those in which the method further comprises the step of analyzing at least one feature of the selected first transposase of (e), the selected first transposase is a mutagenized transposase and the second transposase is a wild type form of the mutagenized transposase.

In certain embodiments of the methods of the disclosure, including those in which the method further comprises the step of analyzing at least one feature of the selected first transposase of (e), the selected first transposase of (e) has a decreased insertion site bias compared to the second transposase.

In certain embodiments of the methods of the disclosure, including those in which the method further comprises the step of analyzing at least one feature of the selected first transposase of (e), the selected first transposase of (e) has a desired feature that is not present the second transposase.

In certain embodiments of the methods of the disclosure, including those in which the method further comprises the step of analyzing at least one feature of the selected first transposase of (e), wherein the selected first transposase is a mutagenized transposase, the method further comprises identifying at least one mutation within the selected first transposase of (e) or a sequence thereof. In certain embodiments, the method further comprises identifying each mutation within the selected first transposase of (e) or a sequence thereof. In certain embodiments, the sequence is an amino acid sequence of the selected first transposase of (e). In certain embodiments, the sequence is a nucleic acid sequence encoding the selected first transposase of (e). In certain embodiments, the identifying comprises sequencing the nucleic acid sequence encoding the selected first transposase of (e).

and Tn5-Tpn[Hyper], where each has been used to create an NGS library. The consensus sequences were derived essentially as described in FIG. 3.

Figure 6:
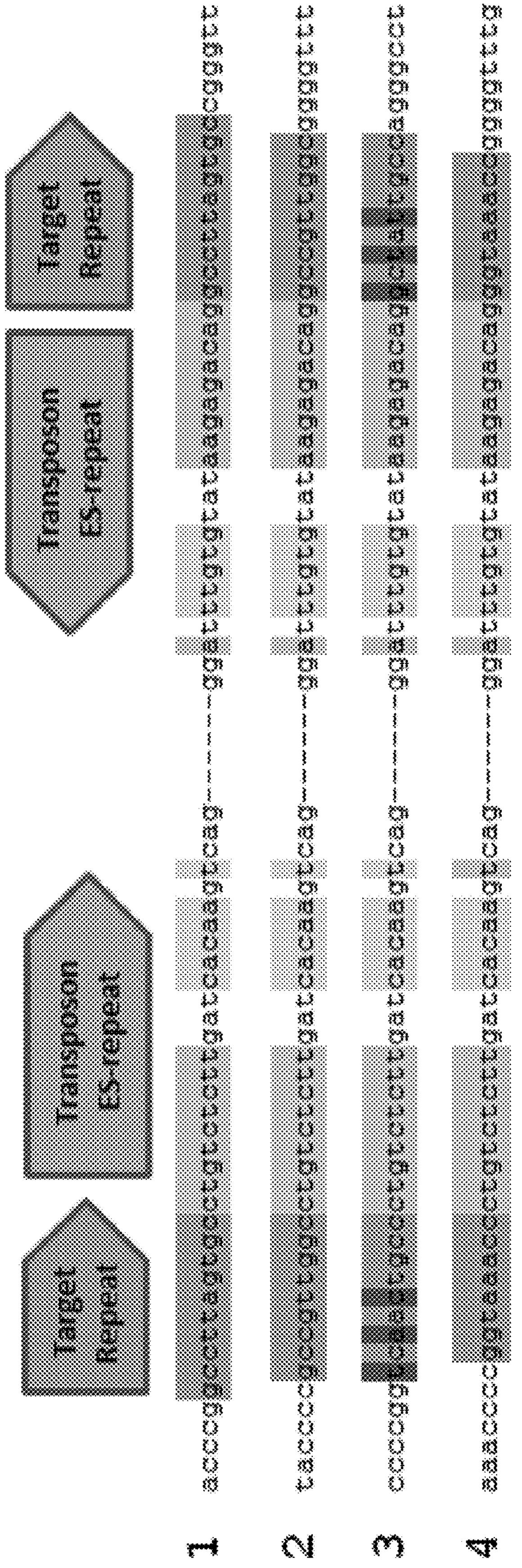

FIG. 6 is a schematic diagram depicting the four TnAa insertion sites in *Alishewanella jeotgali*. The insertion sites of the four TnAa transposons found in *Alishewanella jeotgali* KCTC 22429 are shown, with the transposon inverted end-sequences highlighted in grey, and the directly repeated insertion sites highlighted in yellow. Green highlight shows imperfections in the insertion site repeats. Insert 1 has a 10-base perfect repeat. Insert 2 has a Tn5-type 9-base perfect repeat. Insert 3 has an imperfect Tn5-type 9-base repeat. Insert 4 has an 8-base perfect repeat.

Figure 7:
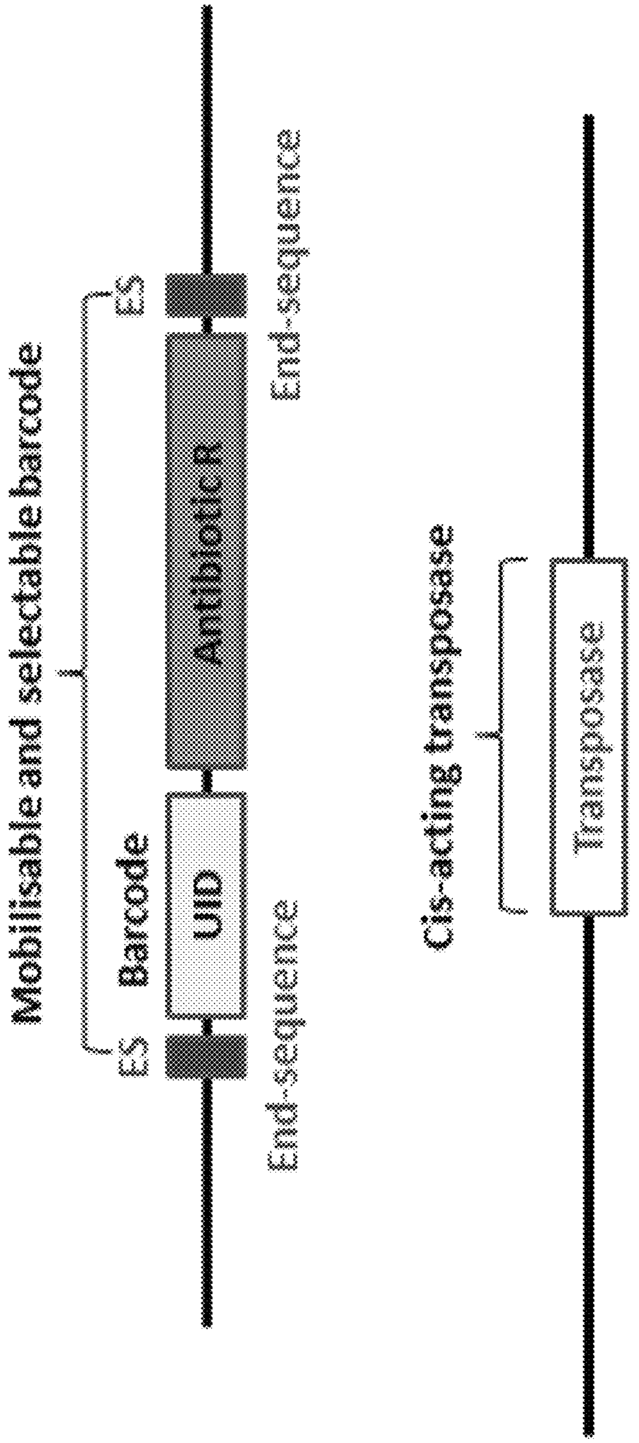

FIG. 7 is a schematic of an outline of a mobilisable and selectable barcode region (not to scale). The mobilisable and selectable barcode comprises three components. The mobile unit includes two transposon end sequences (red) which bracket a unique identifier barcode (UID, pink) and a selectable marker, such as an antibiotic resistance gene (yellow). This unit can be mobilized by expression of a transposase gene. The transposase gene itself does not need to be in close proximity to the mobilisable unit.

Figure 8A:
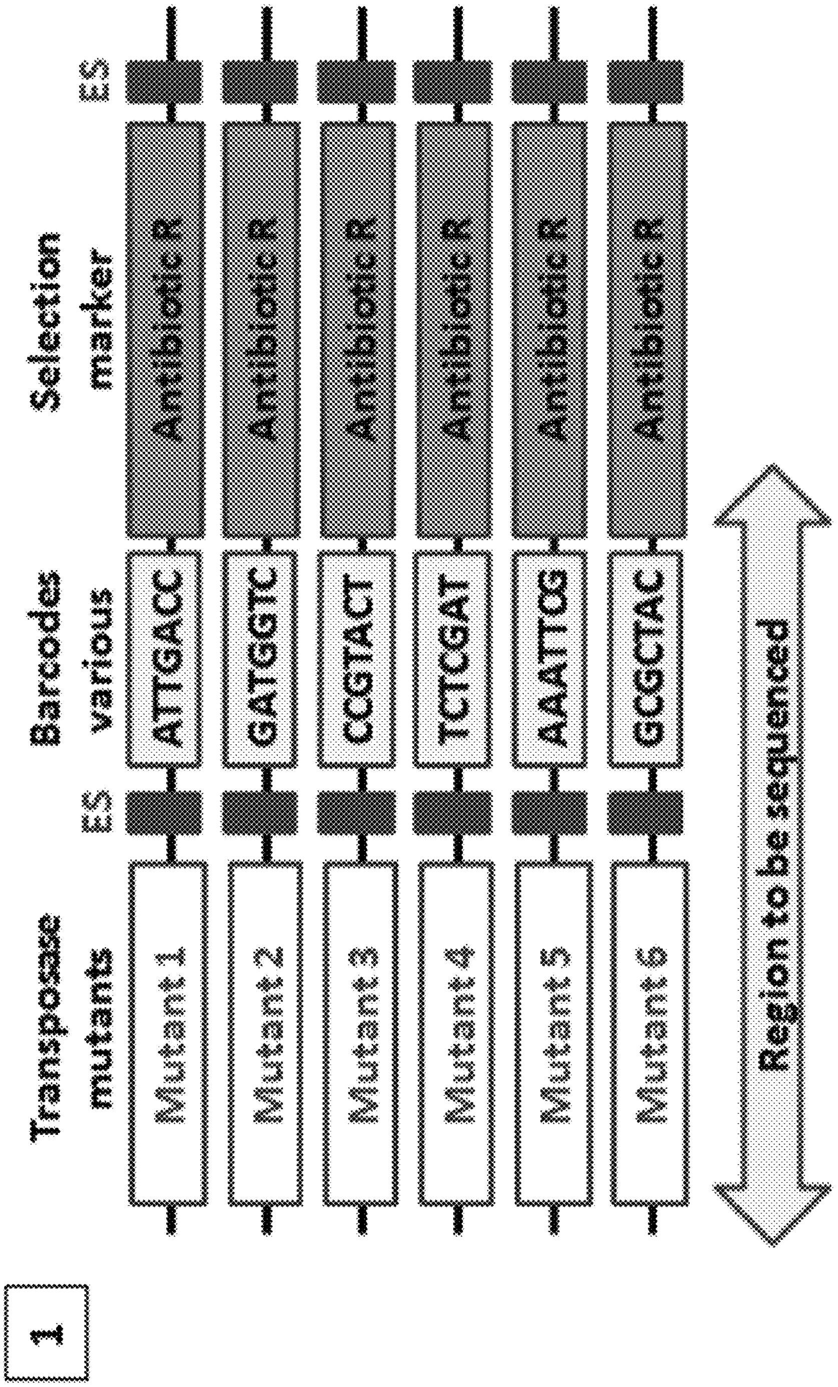
Figure 8B:
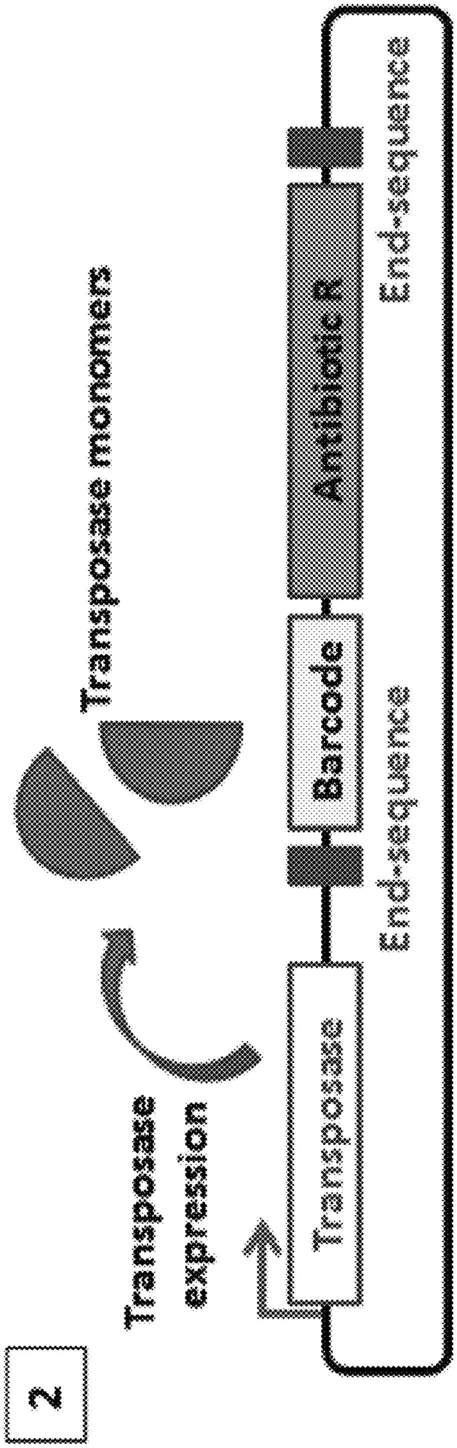
Figure 8C:
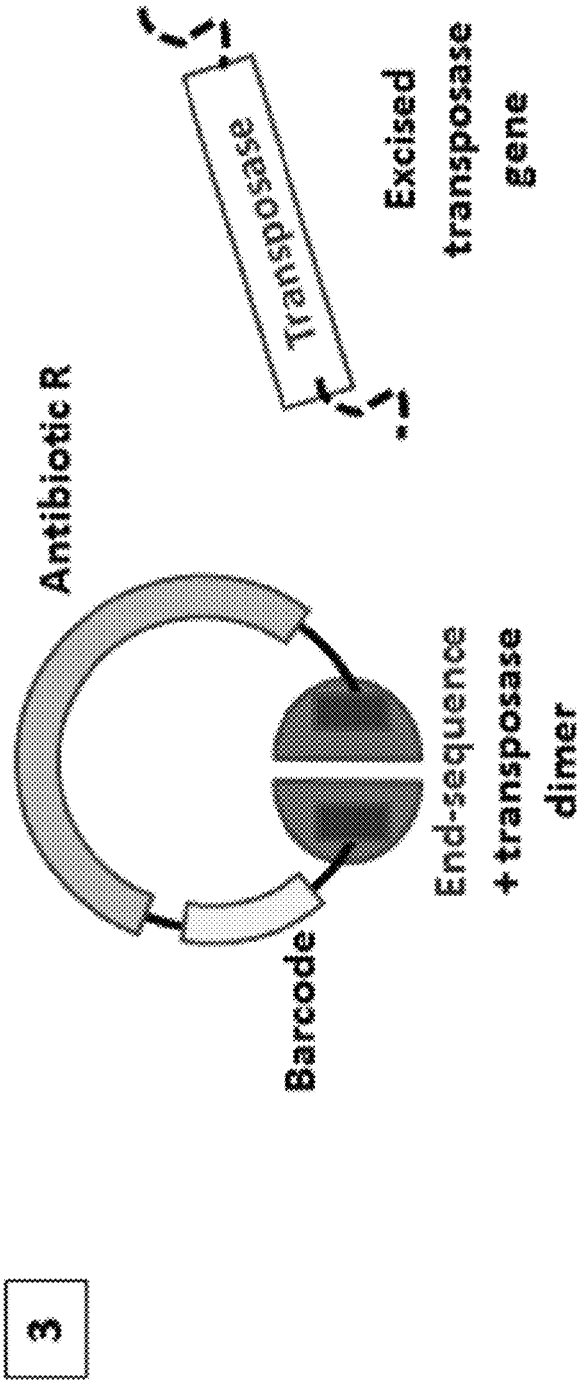
Figure 8D:
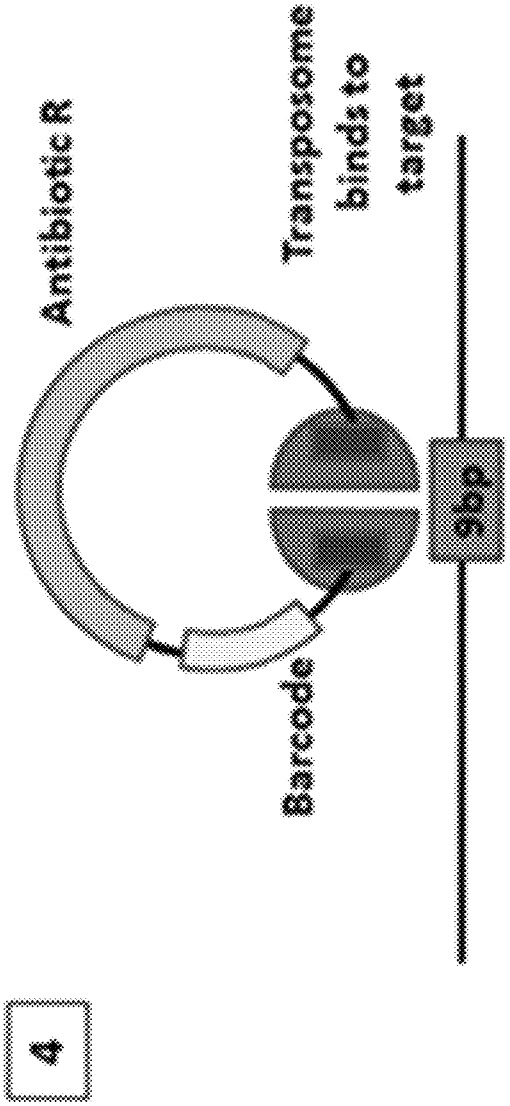
Figure 8E:
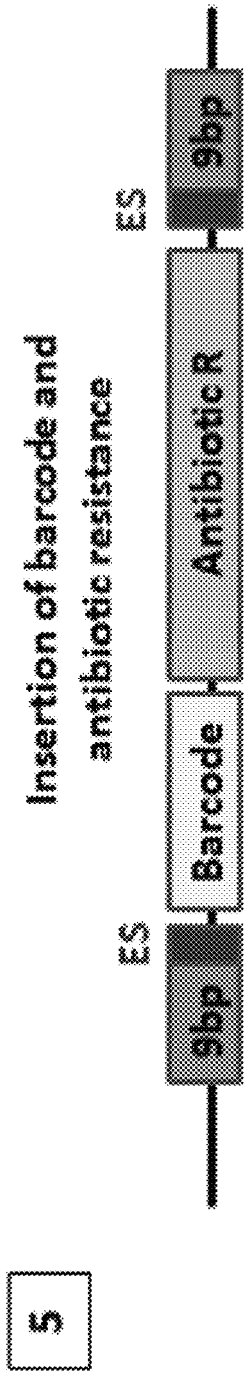
Figure 8F:
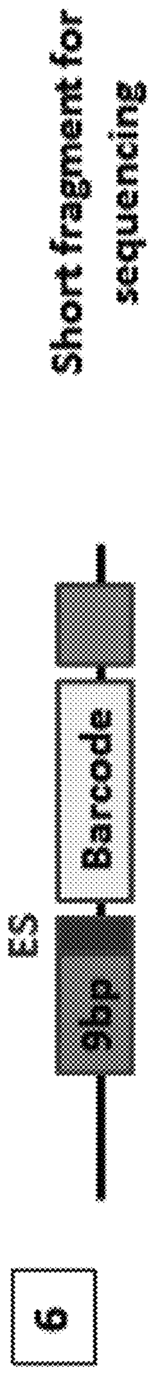
Figure 8G:
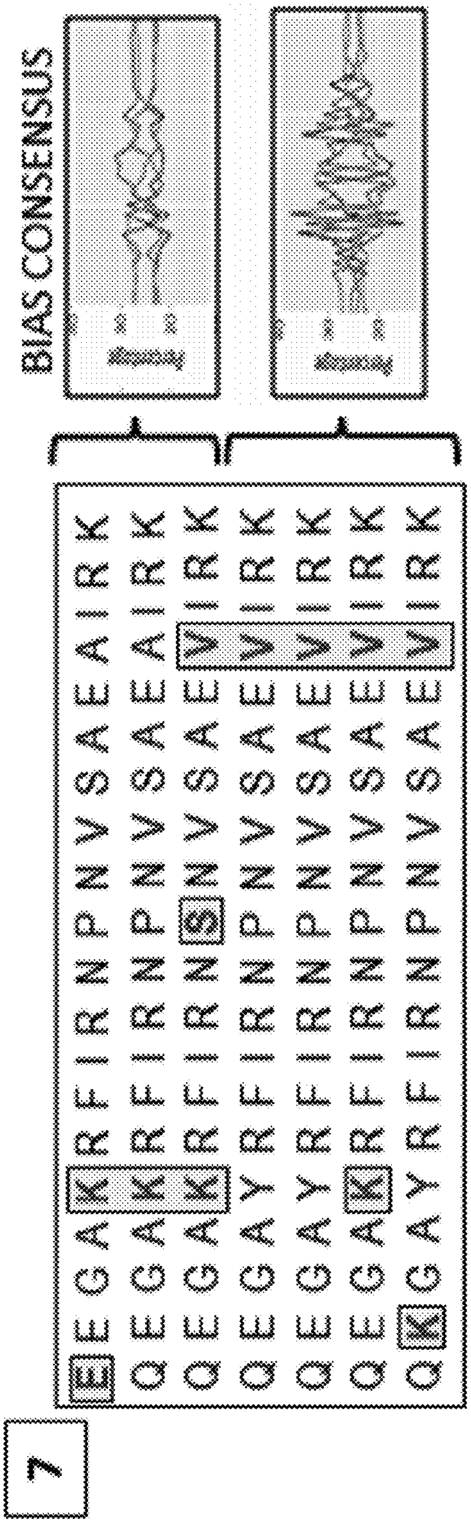

FIG. 8A-8G is a series of schematic diagrams depicting an outline of transposase mutant barcode transposition and screening (not to scale). FIG. 8A shows a library of many thousands of vectors is created. Each vector is different from the others, in that each carries a particular individual mutant transposase and a particular individual mobilisable and selectable barcode region. Once made, the library is cloned to make stocks of the vectors. The library is sequenced over the region including the barcode and the mutant transposase. Because each barcode is different from the others, and it is linked to a particular mutant, it can subsequently be used for identification of each mutant. FIG. 8B shows that the host bacterium is transformed with the library, and each mutant transposase is transiently expressed (the promoter is constitutive but the vector does not replicate) inside the cell. FIG. 8C shows that if the mutant transposase is functional, two molecules attach to the two end-sequences, the dimeric complex is formed and the moblisable, selectable barcode region is excised to form a free transposome. FIG. 8D shows that there is only a single transposome in each cell, as there is only a single original vector molecule to supply the mobilisable region, and the vector cannot replicate. This transposome can bind to a target region on the chromosome, and the target preference is determined by the nature of the transposase mutant. FIG. 8E shows that insertion occurs, and the efficiency of the insertion is determined by the nature of the transposase mutant. Insertion results in the barcode and selectable marker being incorporated into the chromosome. The bacteria become antibiotic resistant and can be selected by application of the appropriate antibiotic. Many clones (possibly millions) can be selected. These represent transposition events driven by thousands of different mutant transposases, with many different transposition events (into different sites) for each mutant. FIG. 8F shows that each insertion site and barcode is then sequenced by NGS. Because each barcode can be correlated with a particular mutant transposase, and because many insertion sites are sequenced for each barcode insertion, it is possible to determine a consensus sequence for the insertion site and to relate that to a particular mutant transposase. In this manner transposases that display different insertion site biases can be identified. See also FIG. 9A-C. FIG. 8G shows that by identifying which mutant transposases have particular insertion bias or activity (or other) characteristics, and identifying the mutations and mutation sites they have in common, key functional positions, specific mutations and useful combinations can be described.

Figure 9A:
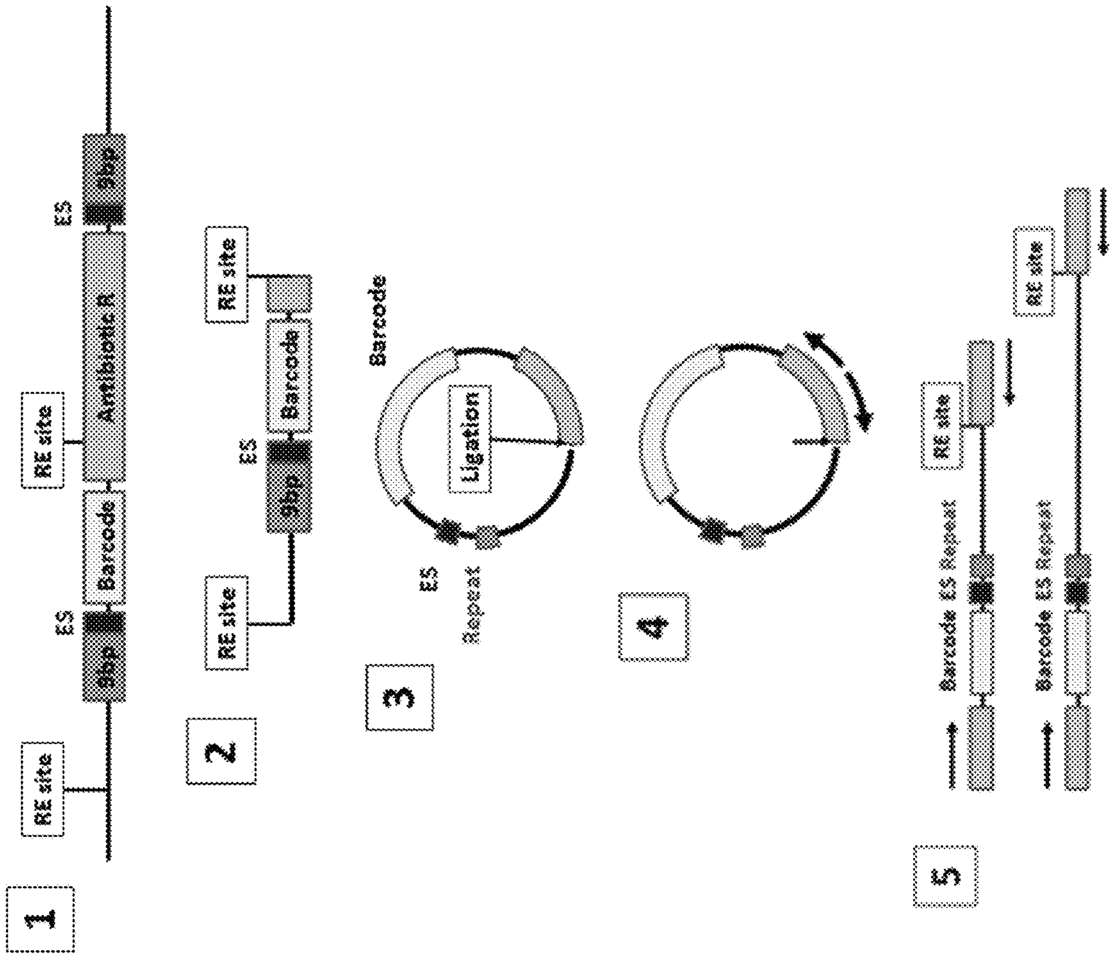
Figure 9B:
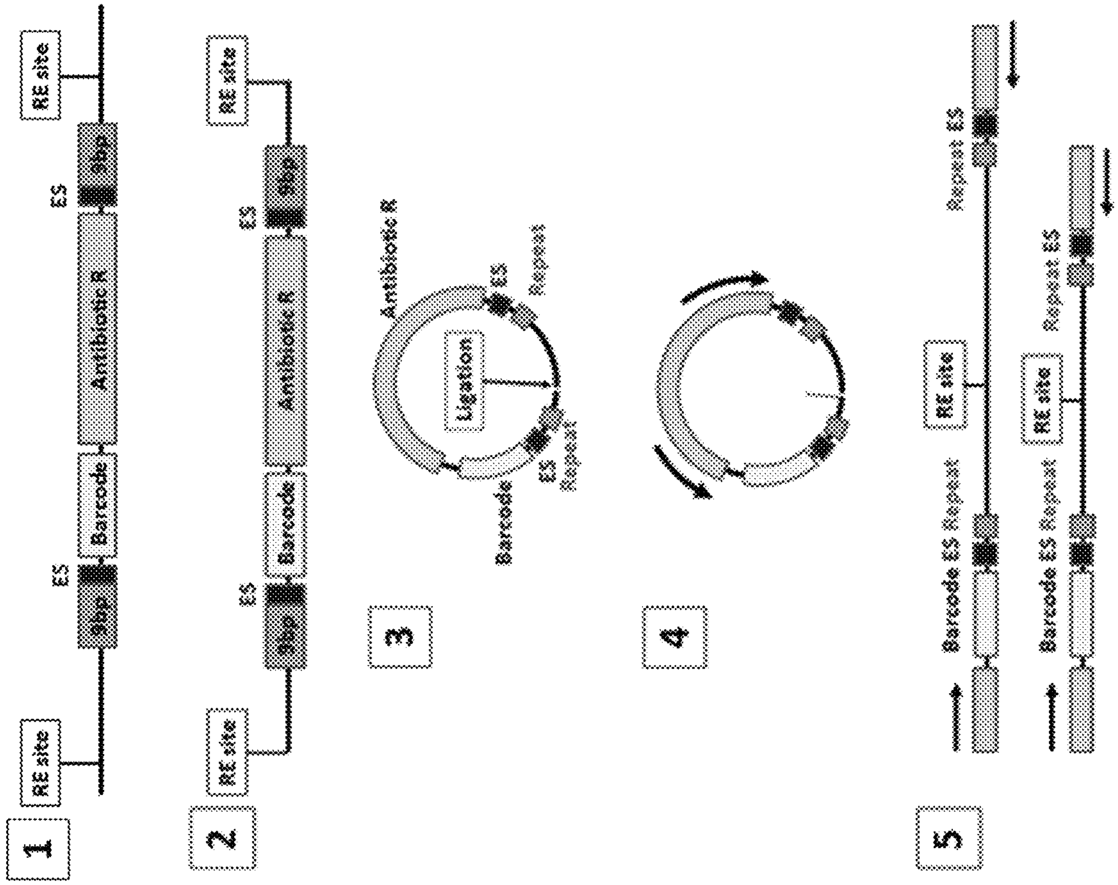
Figure 9C:
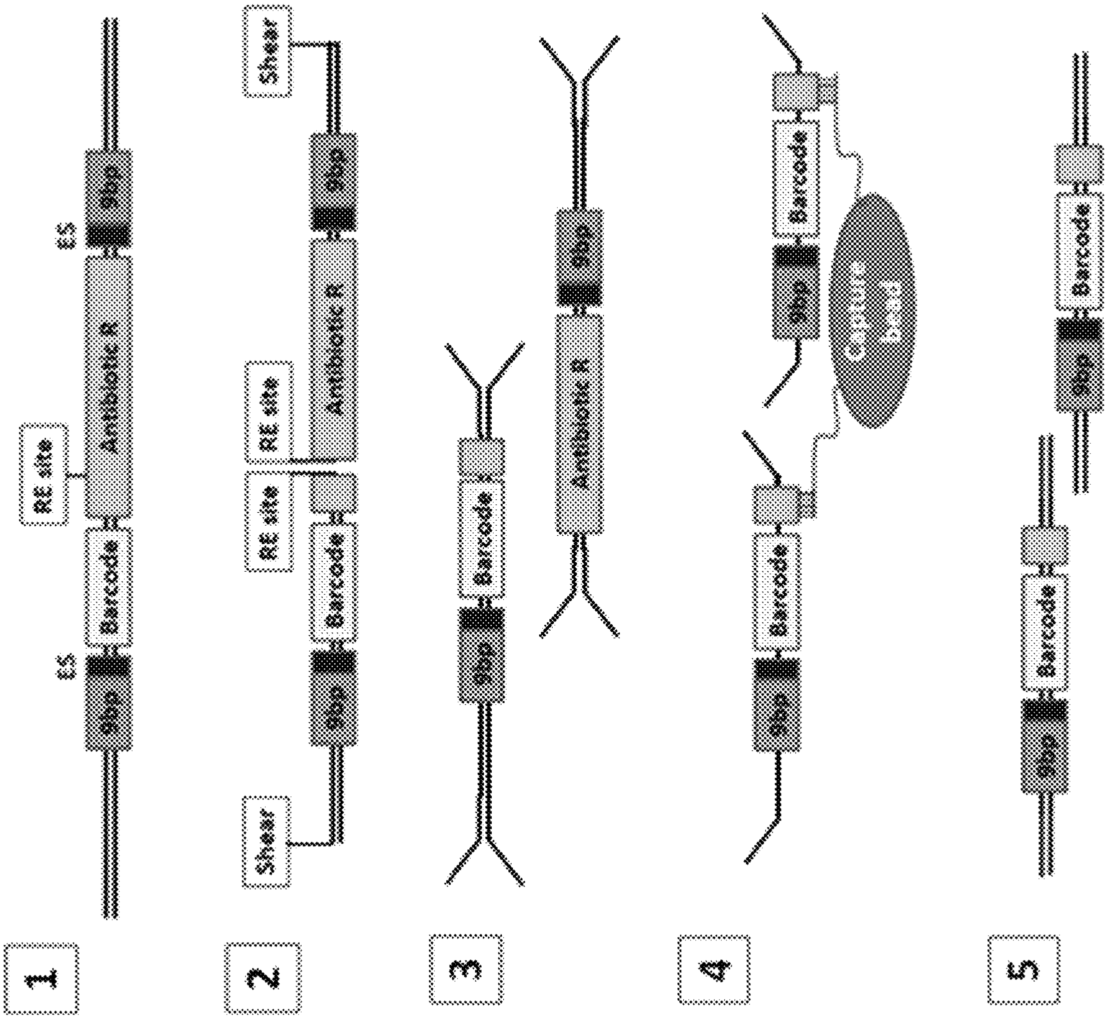

FIG. 9A-C is a series of schematic diagrams depicting exemplary methods for isolation and preparation of insertion sites for Next Generation Sequencing (NGS). (A) Inversion PCR to sequence one end of the insertion site. (1) The mobilized marker and barcode are shown inserted into the target chromosome. The chromosomal DNA of all the different clones, each with a different insertion, is isolated. (2) Restriction enzyme(s) that cut once adjacent to the barcode are used to digest the DNA. This frees one side of the insertion site, the barcode and a short nearby region. (3) The fragments are circularized by intra-molecular ligation. (4) Inversion PCR is then carried out using outward-facing primers. (5) Because the target molecule is circular, the PCR products comprise an inverted section of the chromosome, which carries one end the insertion site and the barcode. These fragments can then be used to create an NGS library and one end of the amplicons is sequenced to reveal one insertion site end and the UID barcode of the transposase. (B) Inversion PCR to sequence both ends of the insertion site. (1) The mobilized marker and barcode are shown inserted into the target chromosome. The chromosomal DNA of all the different clones, each with a different insertion, is isolated. (2) Restriction enzyme(s) that do not cut within the region between the end-sequences are used to digest the DNA. This frees the whole insertion site, barcode and antibiotic selection fragment. (3) The fragments are circularized by intra-molecular ligation. (4) Inversion PCR is then carried out using outward-facing primers. (5) Because the target molecule is circular, the PCR products comprise an inverted section of the chromosome, and the ends of the amplicon carry the insertion site and barcode. These fragments can then be used to create an NGS library and both ends of the amplicons are sequenced to reveal the insertion site and the UID barcode of the transposase. (C) Capture to sequence one end of the insertion site. (1) The mobilized marker and barcode are shown inserted into the target chromosome. The chromosomal DNA of all the different clones, each with a different insertion, is isolated. (2) Restriction enzyme(s) that cut once adjacent to the barcode are used to digest the DNA. In addition the DNA is randomly sheared. This frees one side of the insertion site, barcode and a short nearby region. (3) The DNA is size fractionated, and sequencing adapters are ligated. Amplification can be applied. (4) The strands are separated and hybrid capture applied to isolate only one end of the insertion site. (5) The Library is amplified and is ready for sequencing.

Figure 10:
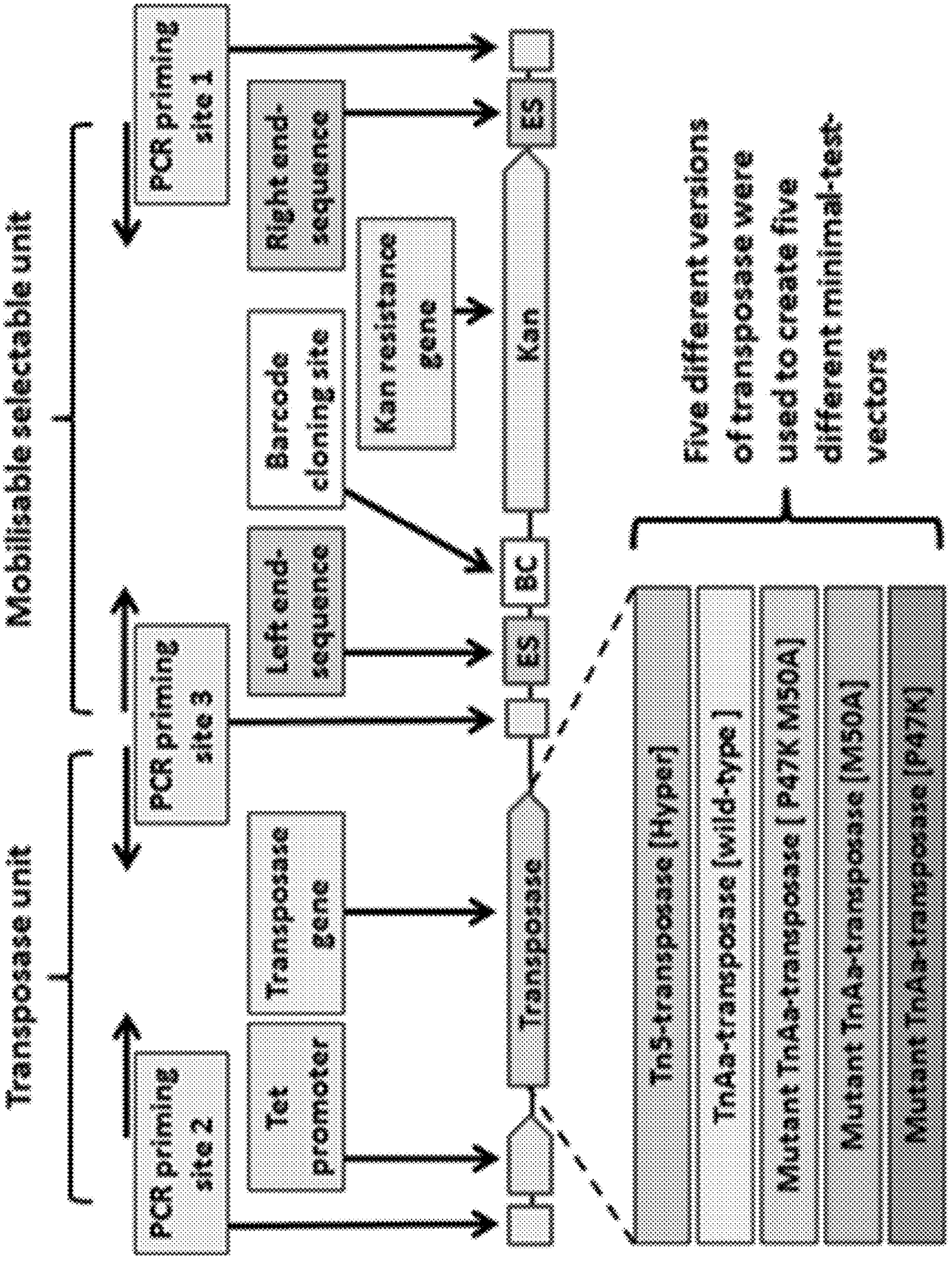

FIG. 10 is a schematic diagram providing an outline of a minimal test vector (not to scale). The overall layout of the full minimal test vector is shown. It comprises two adjoined regions; the first is the transposase expression unit, the second is the mobilisable selectable unit. Each of these two regions is bracketed by short non-functional stretches that can be used as priming sites for PCR. The transposase unit consists of a transposase gene (various) and expression signals, with expression driven constitutively by the tet promoter. The mobilisable selectable unit is essentially as described in FIG. 7, except that the barcode has not yet been added (but a restriction-cloning site is present) and the selectable marker is a kanamycin resistance gene that is constitutively expressed from its natural promoter.

Figure 11:
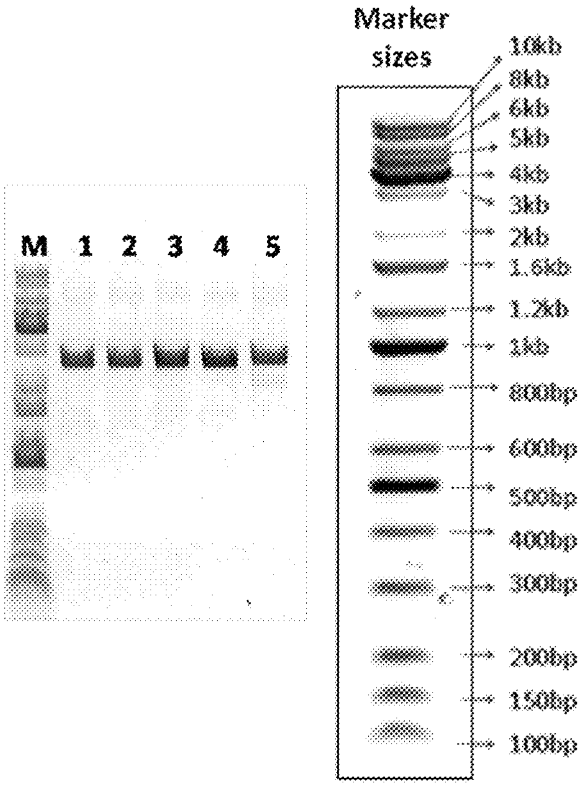

FIG. 11 is a photograph of an agarose gel for visualization of purified minimal test vector amplicons. PCR amplified minimal test vector was purified. Prior to further use this PCR amplified minimal test vector was separated on a 7.5% TBE agarose gel, stained with ethidium bromide and visualized under UV. The Tn5 product (2734 bp) is expected to be slightly larger than the TnAa products (2674 bp); all bands are at the correct position. The TnAa double-mutant product (lane 4) was subsequently shown to carry a single base deletion and is not here considered further.

Figure 12A:
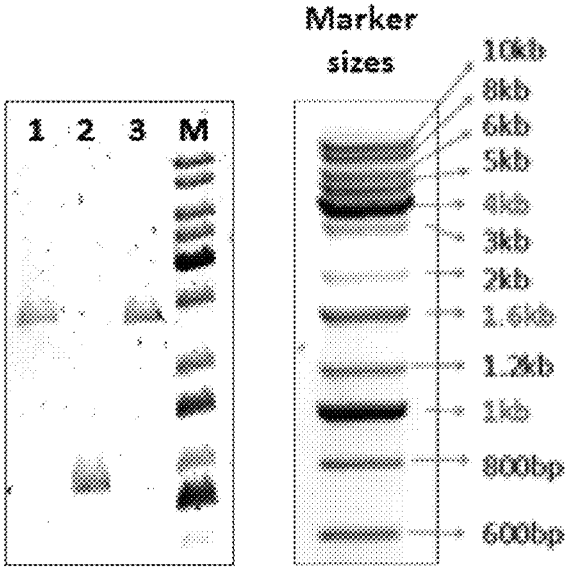
Figure 12B:
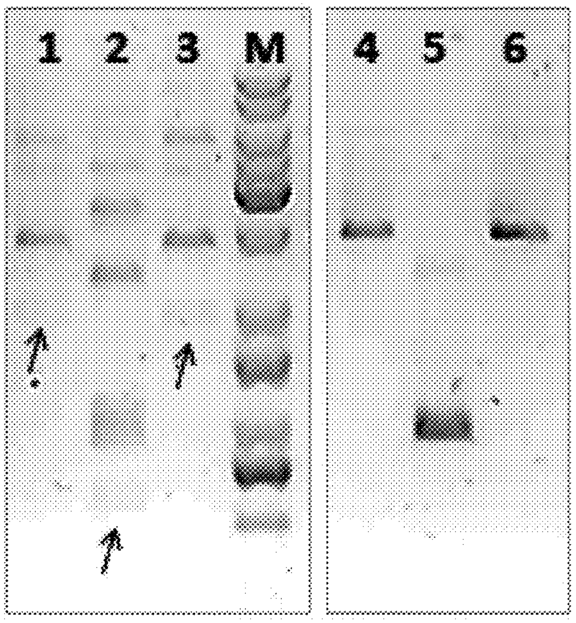

FIG. 12A-B is a pair of photographs of agarose gels for the production of circularized minimal test vectors. PCR amplified minimal test vector was prepared for transformation after circularization. At different steps, test samples were separated on a 7.5% TBE agarose gel, stained with ethidium bromide and visualized under UV. (A) Linear vectors after blunt-end creation and phosphorylation. (B) Vectors after ligation. Lanes 1-3 show ligations with phosphorylated vectors. Lanes 4-6 show ligations with vectors that have not been phosphorylated and therefore are not expected to join or circularize. Arrows indicate circularized molecules.

Figure 13:
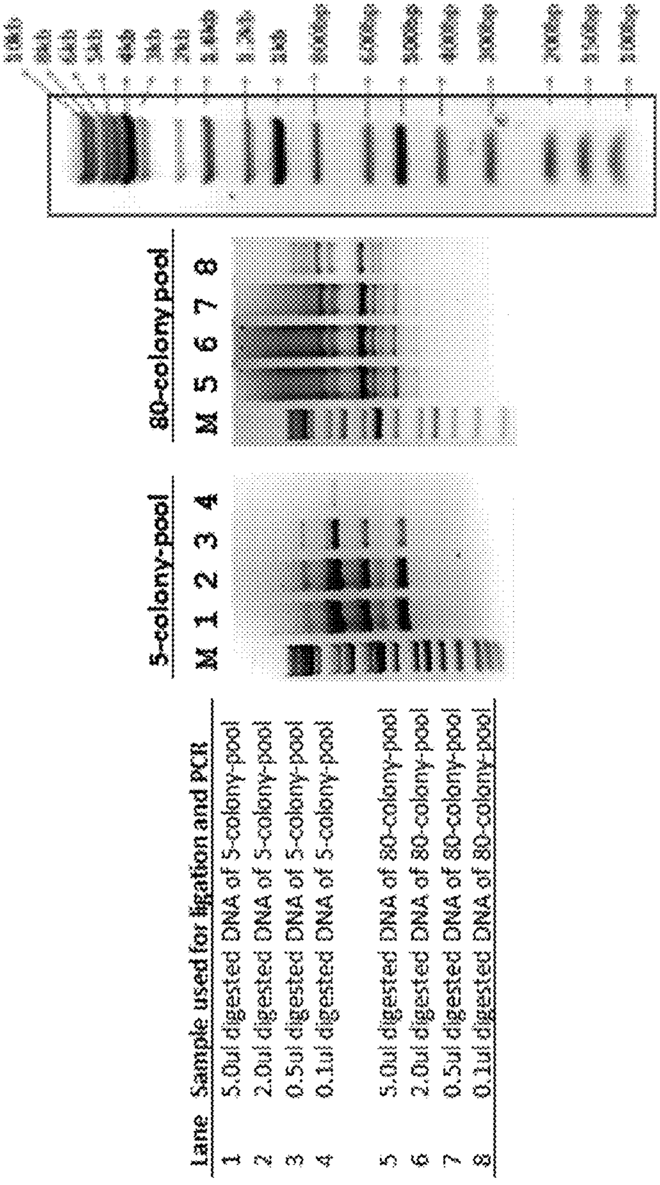

FIG. 13 is a photograph of an agarose gel for visualization of inversion PCR of insertion sites of TnAa-Tpn [P47K]. TBE agarose gel of separated products from the inversion PCR of self-ligated, circularized insertion sites.

Figure 14B:
Figure 14C:
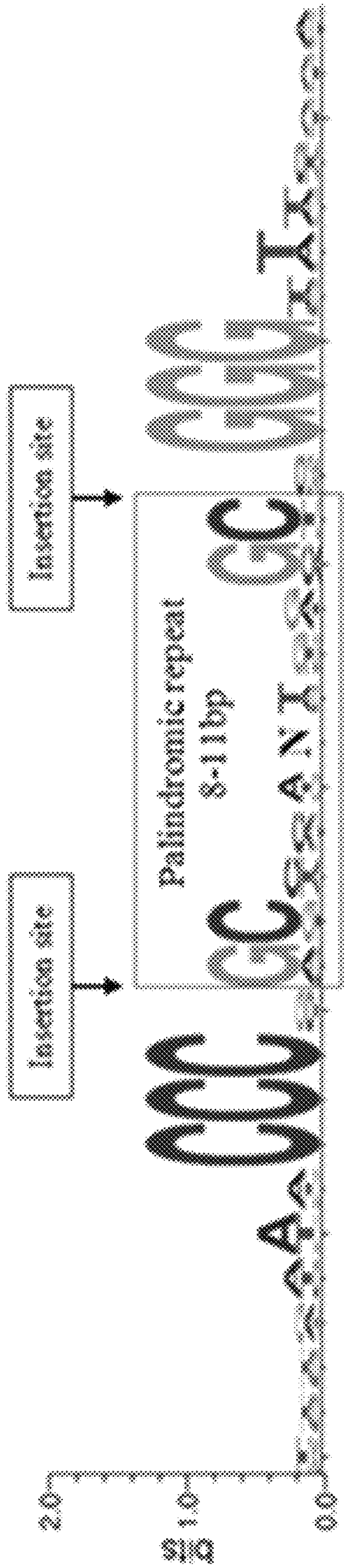

FIG. 14A-C is a series of schematic diagrams depicting sequences and consensus of nine insertion sites using the TnAa-Tpn [P47K] minimal test vector. Both sides of nine insertion sites were sequenced. The original site (before) insertion was recreated and the repeat region identified (shown in grey highlight). (A) Shows the sites aligned at the left-hand-side insertion site. (B) Shows the sites aligned at both the left- and right-hand-side insertion sites, with a central spacing, which is required in order to compensate for repeat length differences. Both the original insertion sites, and their reverse compliments are included. (C) Shows a weblogo consensus derived from (B), with the central base (N) excluded, as there is insufficient representation at this position to be meaningful.

FIG. 15A-F is a series of schematic diagrams depicting a process of cloning vector components and preparing final constructs. (A) The original minimal test vector. (B) This is cloned in parts onto three separate plasmids and sequenced. (C) Transposase is mutagenized and amplified, the barcode UIDs are cloned into the mobilisable region. (D) The mutant transposases are cloned into the barcoded mobilisable region carrying plasmid. (E) The expression fragment and transposase-mobilisable fragment DNA is cut out of the two input plasmids by restriction digestion and purified. (F) The two fragments are joined and amplified by assembly PCR, and are then ready for circularization and transformation.

Figure 16A:
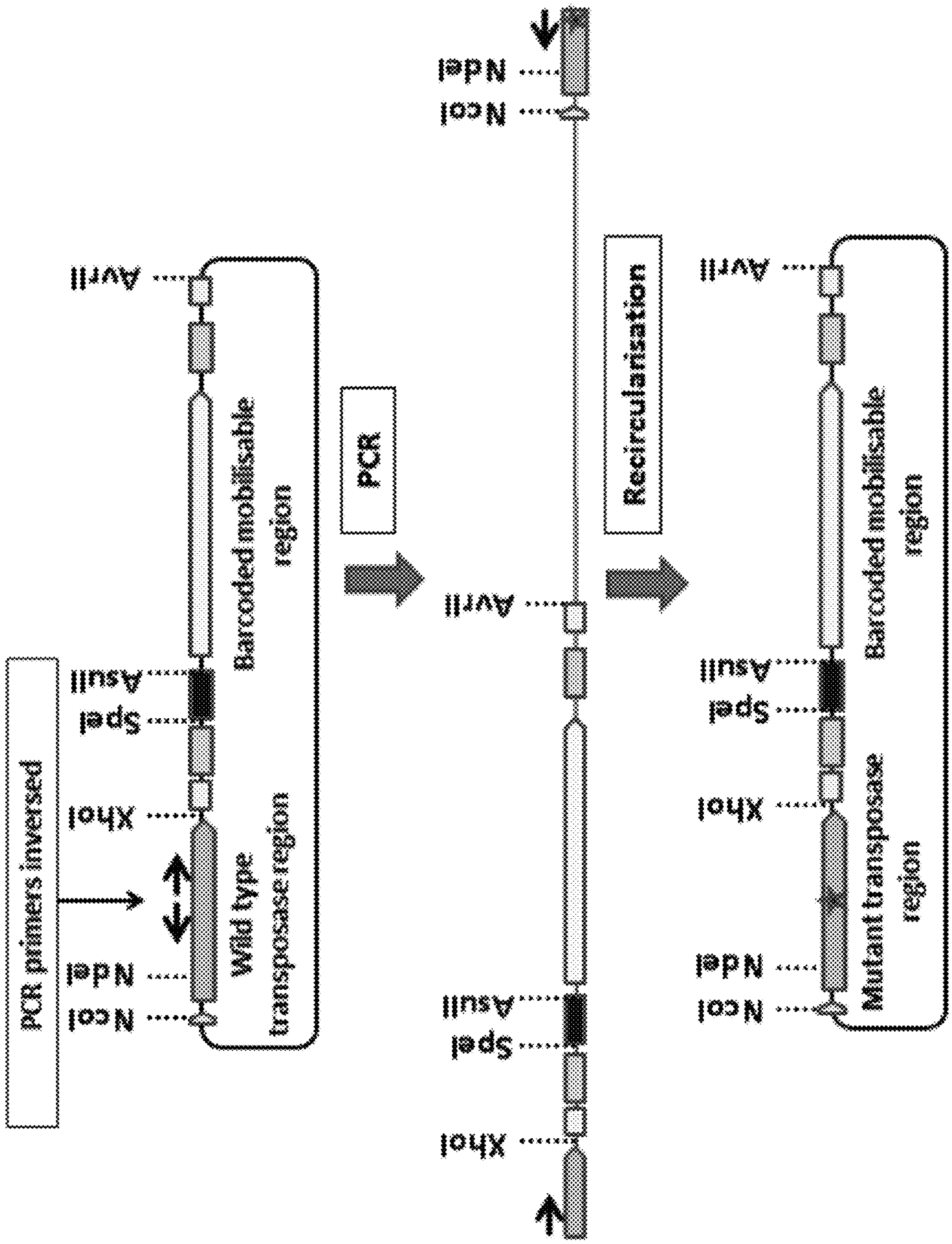
Figure 16B:
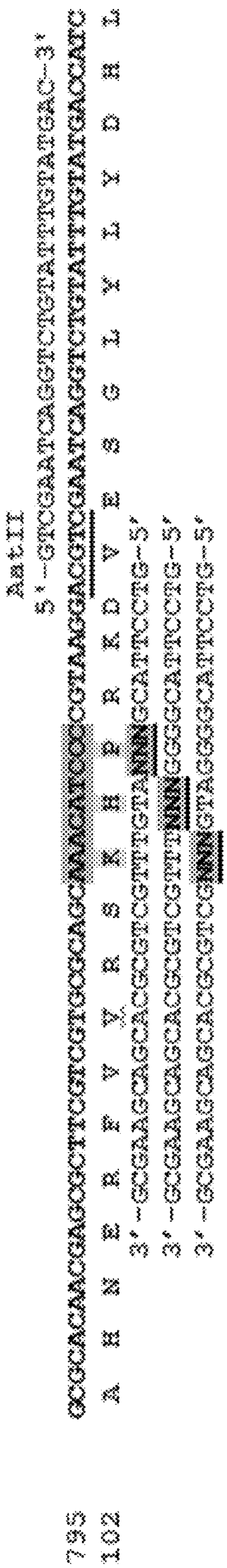

FIG. 16A-B is a pair of schematic diagrams depicting a process of creating site directed saturation mutagenesis constructs. (A) A wild type transposase gene is cloned in the appropriate position, adjacent to the barcoded mobilisable region. Outward facing primers within the transposase gene are used to amplify the whole plasmid. Because one of the primers has a nucleotide triplet of random sequence, a single position within the transposase is mutagenized to all possible codons. The plasmids are re-circularized by ligation and used to transform the host. (B) An example of the primers used to mutagenize the positions K212, H213 and P214 of the transposase Tn5, numbering according to the sequence of the Tn5 hypernuclease transposase minimal test vector (SEQ ID NO: 6).

Figure 17:
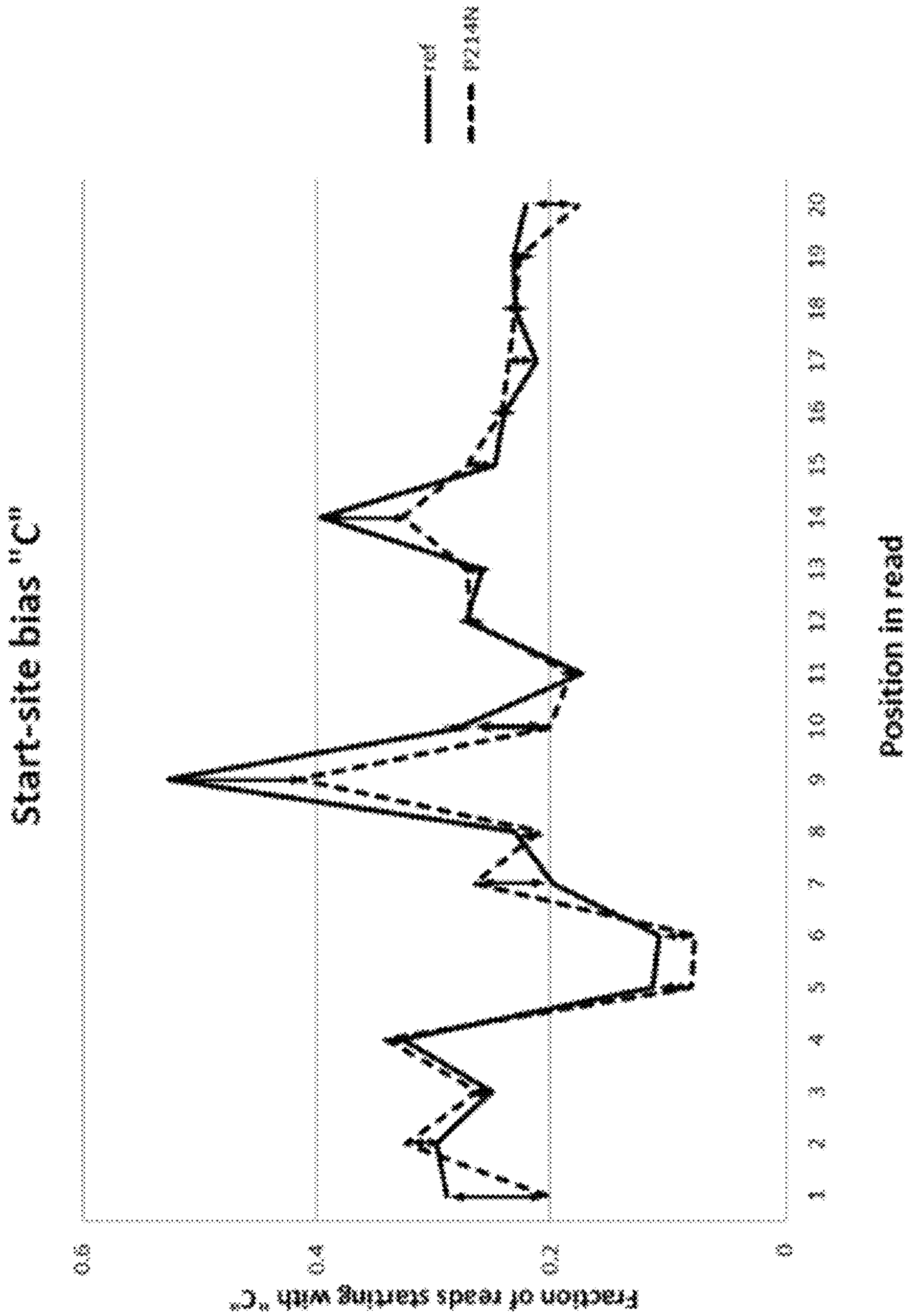

FIG. 17 is a plot of fraction of reads starting with "C" as a function of position in read depicting the start site bias for two transposase constructs, the reference Tn5-E54K and the mutant P214N. The graphs indicated the fraction of reads that start with a "C" for each of the first 20 positions in the sequence reads of the insertion site in the *E. coli* genome. The vertical arrows indicate the absolute difference between the two graphs for each position in the read.

Figure 18:
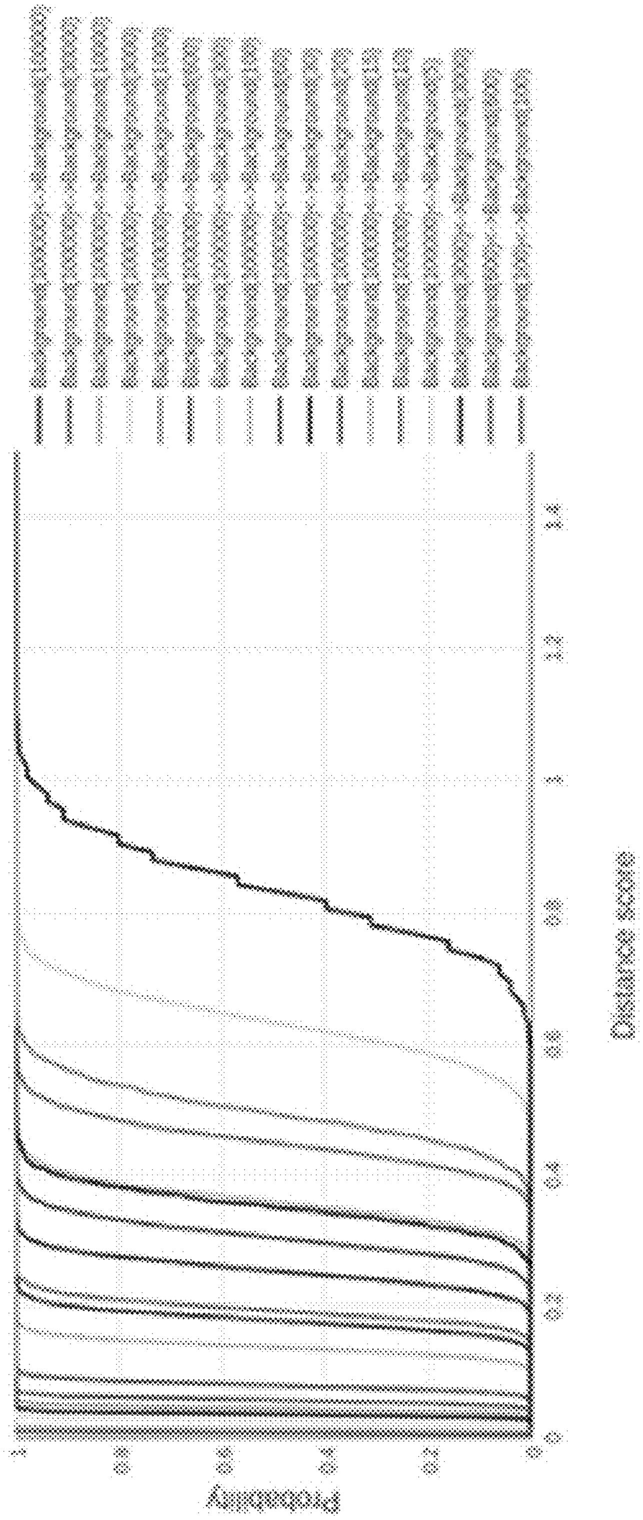

FIG. 18 is a graph demonstrating the relationship between the probability of a statistically significant distance score for inter-motif distance, given the numbers of sequences in motif A and B.

Figure 19:
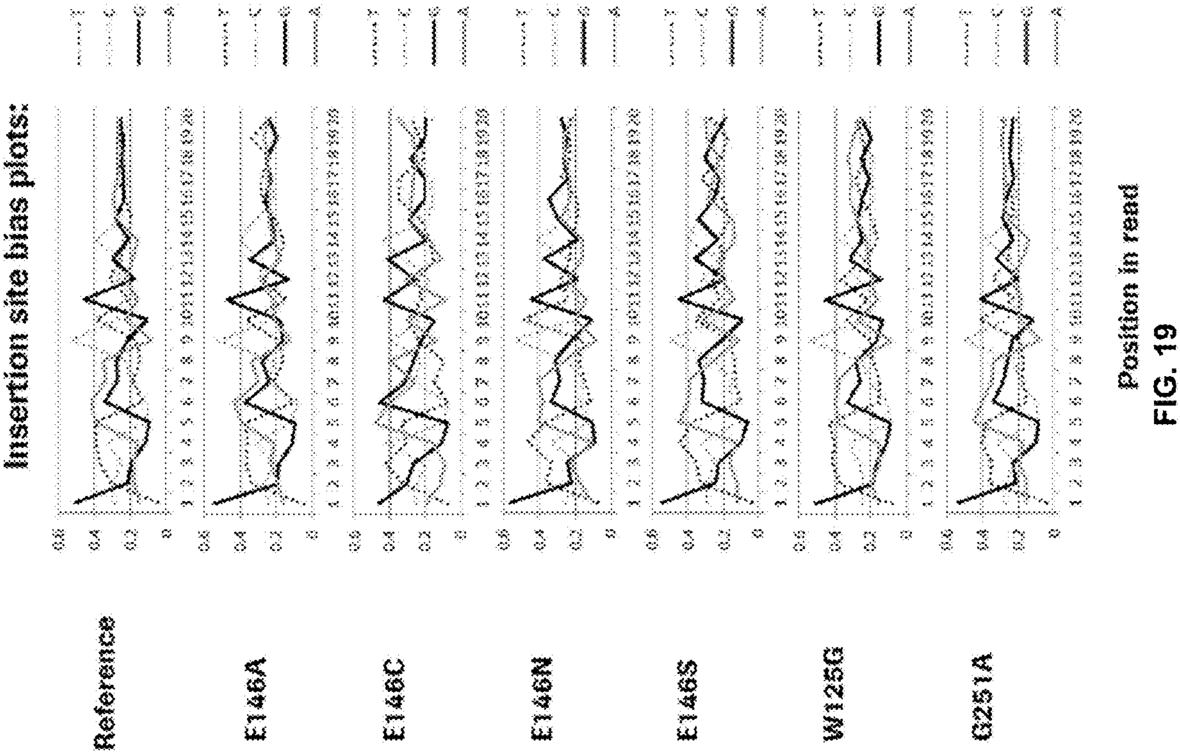

FIG. 19 is a series of graphs illustrating the start-site bias plots for various Tn5 mutants and the reference Tn5 E54K. The x-axis indicates the position in the read and the y-axis indicates the fraction of reads with a "T", "C", "G" or "A" at that position.

Figure 20:
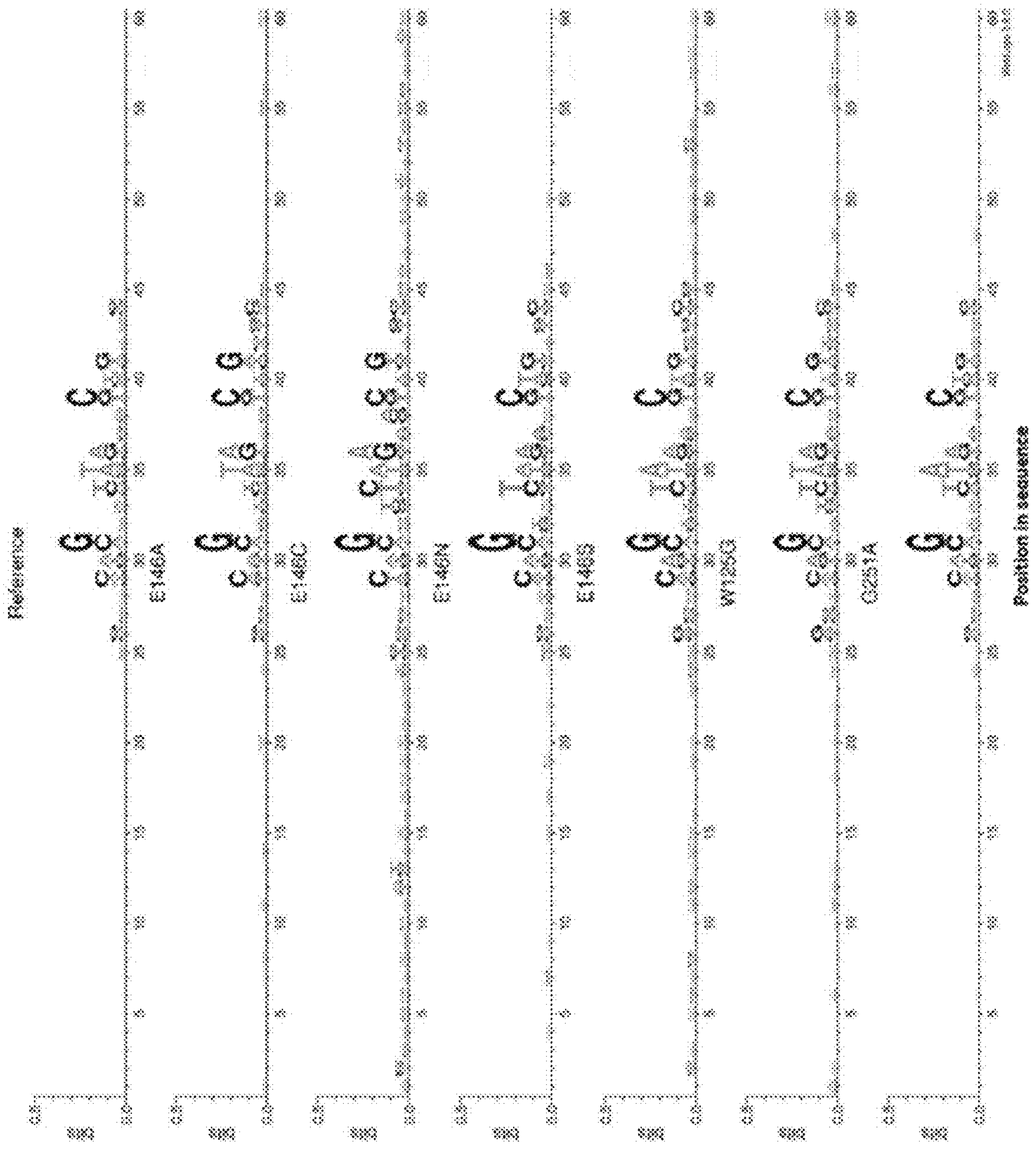

FIG. 20 is a sequence logo illustrating the start-site bias for various Tn5 mutants and the reference hyperactive Tn5 mutant (SEQ ID NO: 1). The logo is generated using Weblogo3 based on an alignment of reads for each transposase.

Figure 21:
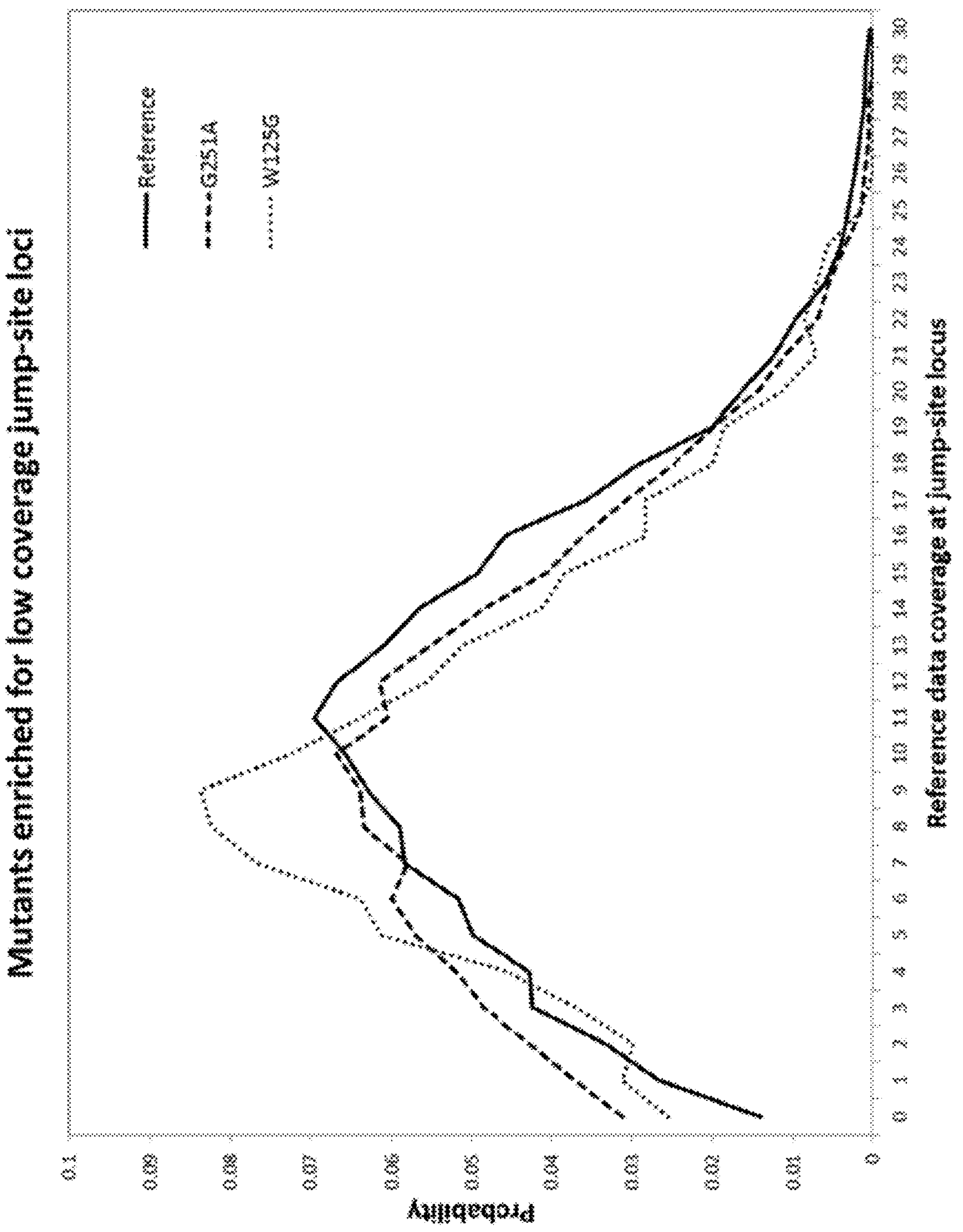

FIG. 21 is a graph depicting mutants with improved coverage at poor-coverage regions. The background genotype, B, is the hyperactive Tn5 mutant (solid line), which is the actual background genotype from which the mutants were mutated in the BATS experiment.

Figure 22:
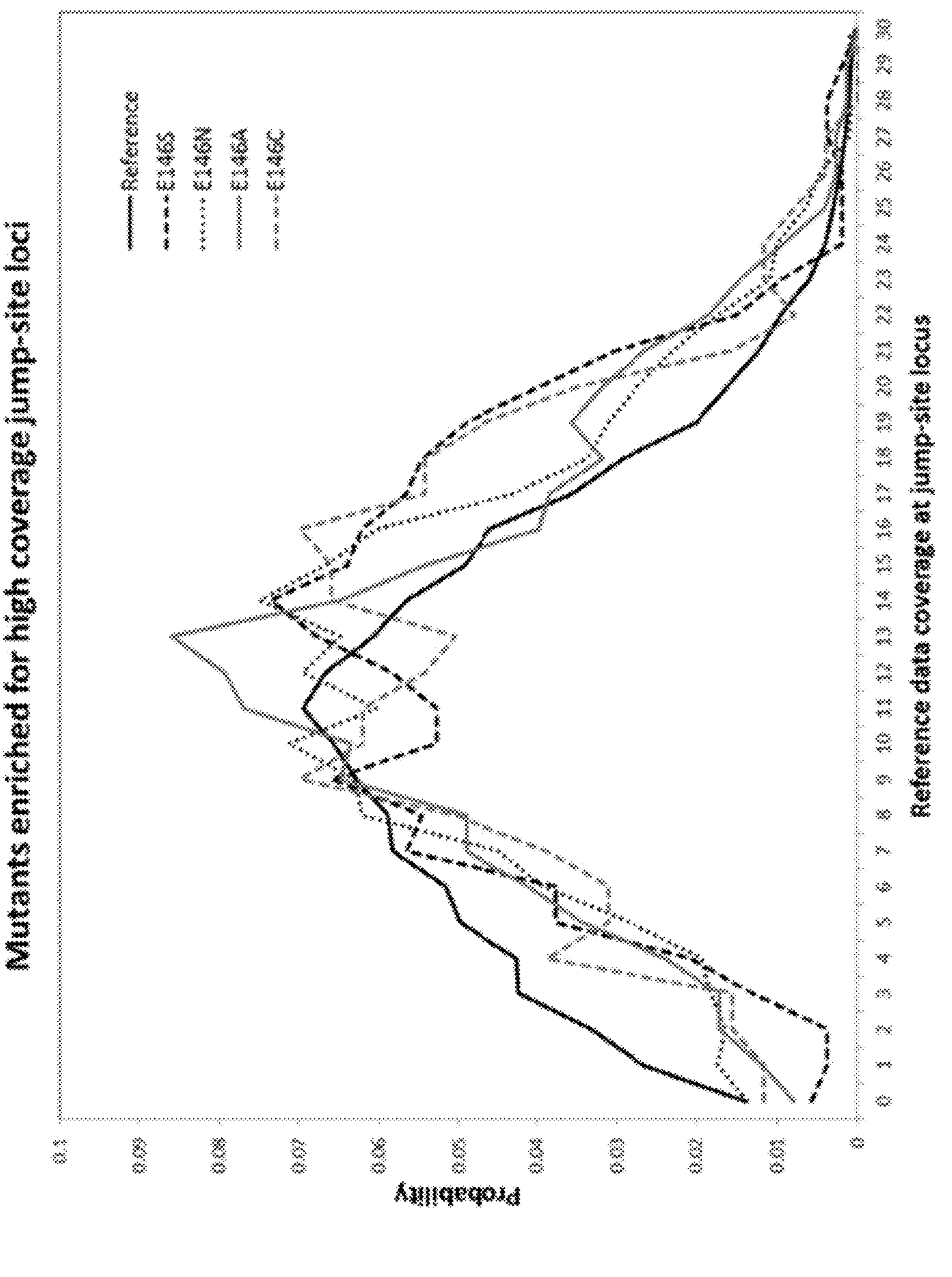

FIG. 22 is a graph depicting mutants with lower coverage at poor-coverage regions. The background genotype, B, is the hyperactive Tn5 mutant (solid line), which is the actual background genotype from which the mutants were mutated in the BATS experiment.

Figure 23:
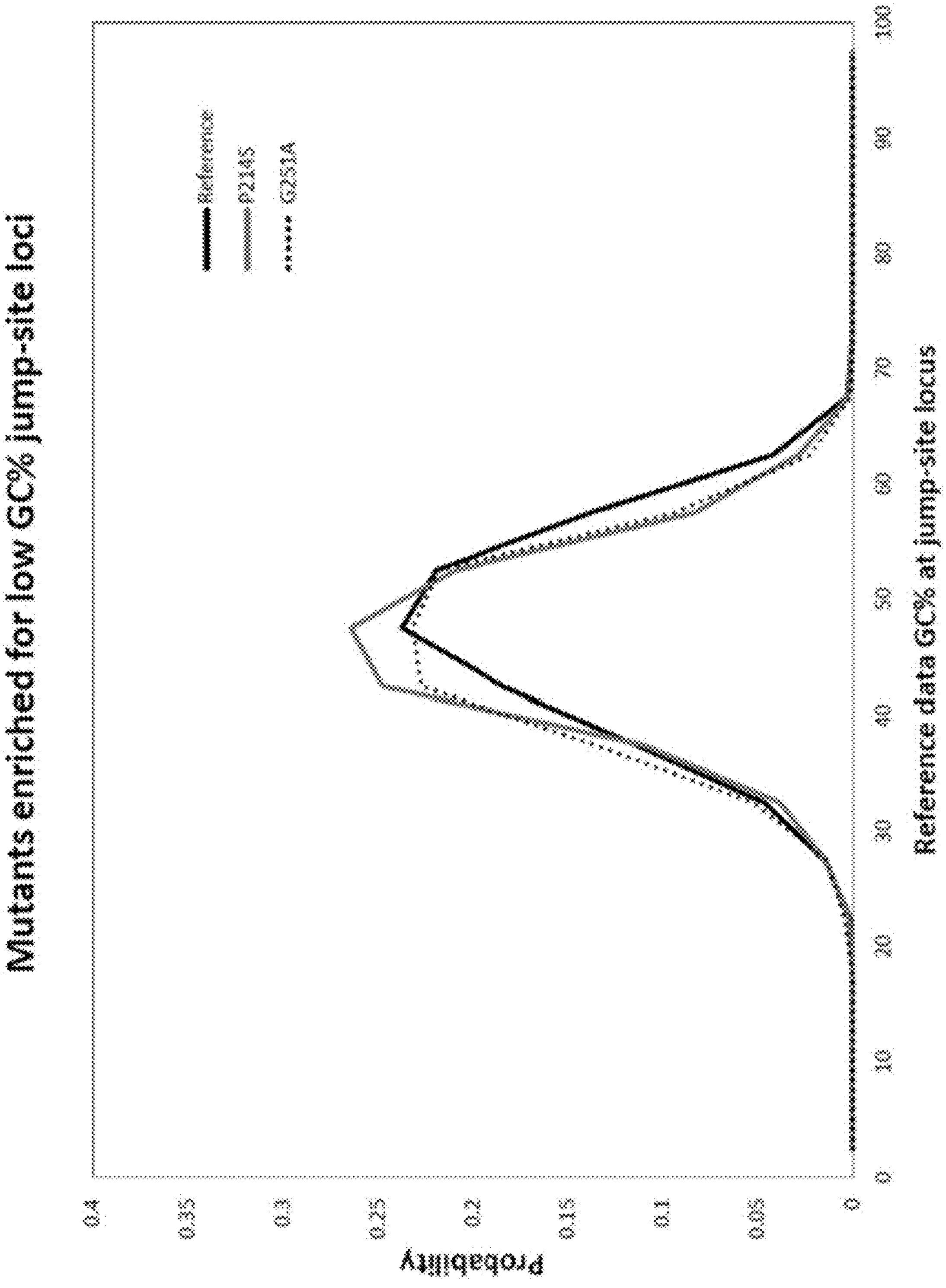

FIG. 23 is a graph depicting the probability of catalysing mobilisable element insertion by the reference or two mutant transposases into loci depending on the GC-content of the loci.

Figure 24:
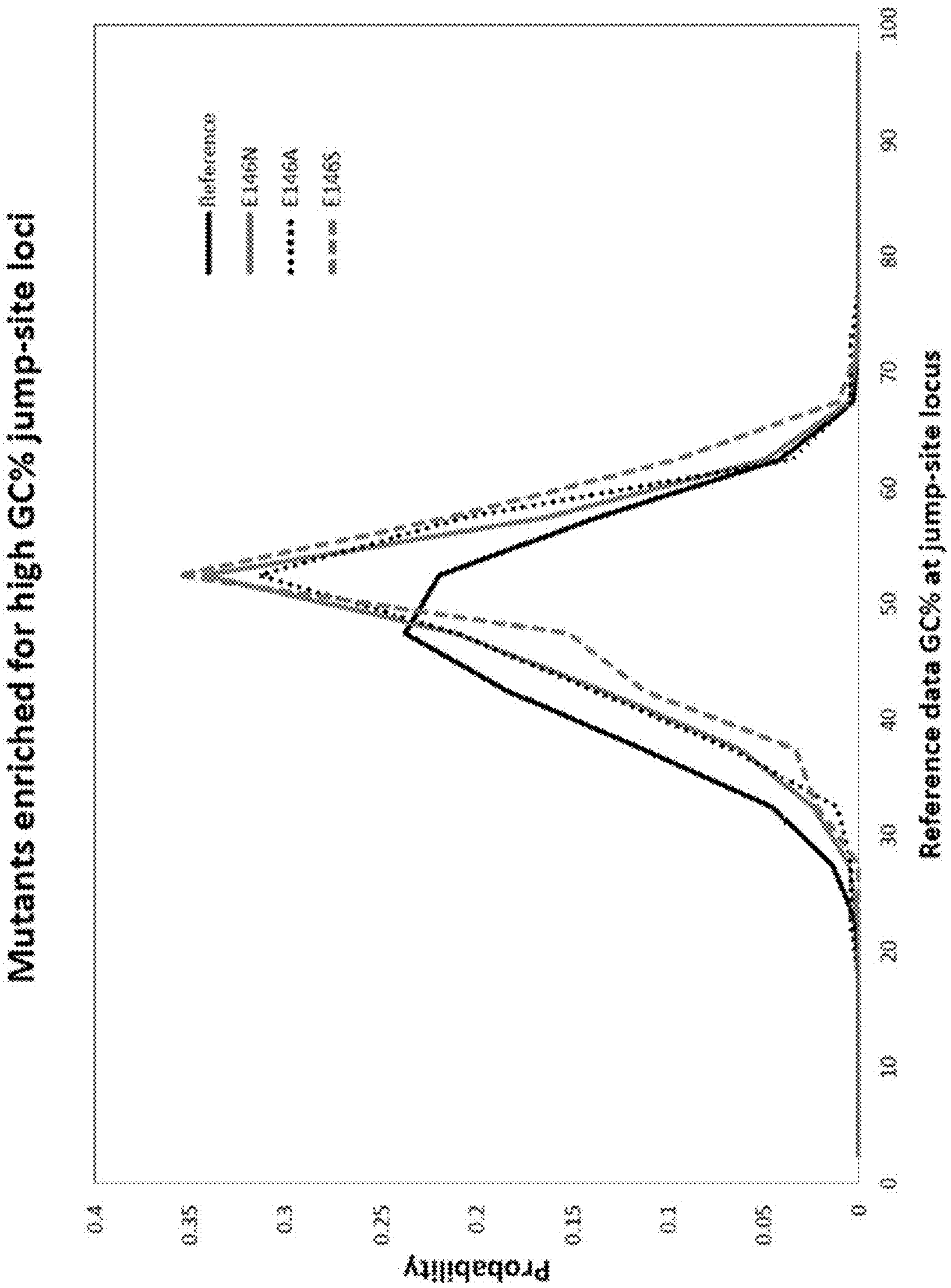

FIG. 24 is a graph depicting the probability of catalysing mobilisable element insertion by the reference or three mutant transposases into loci depending on the GC-content of the loci.

Figure 25:
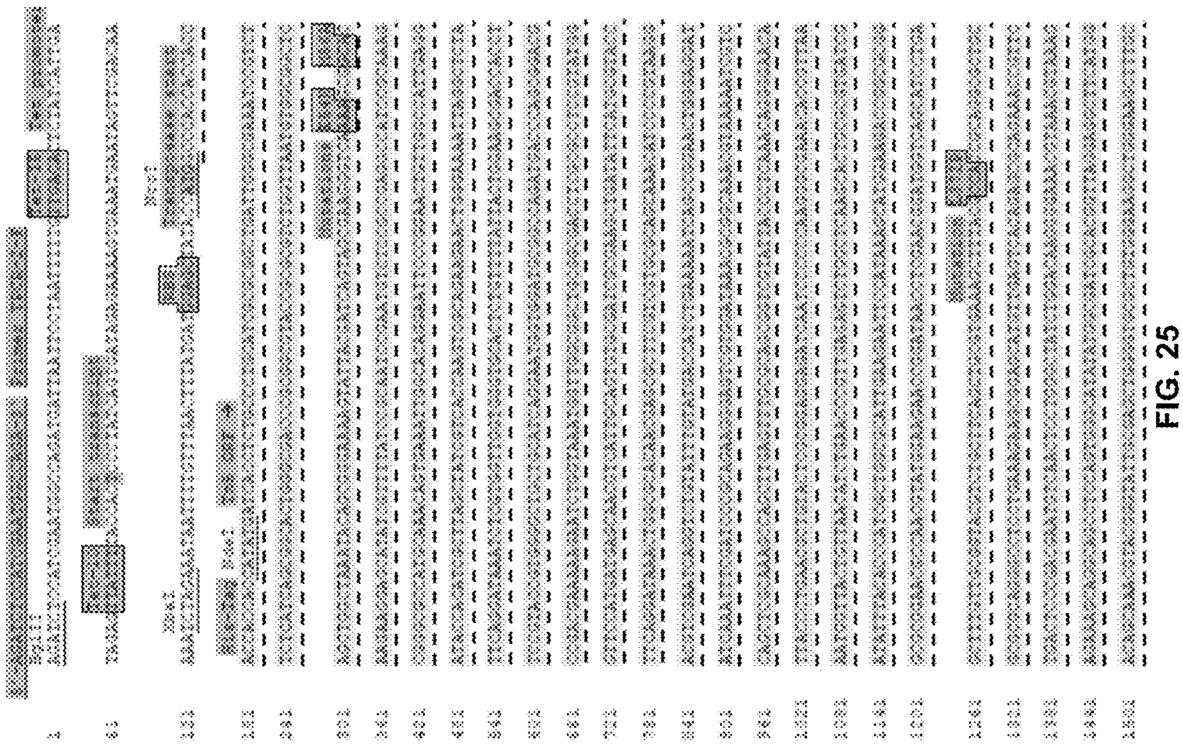
Figure 25:
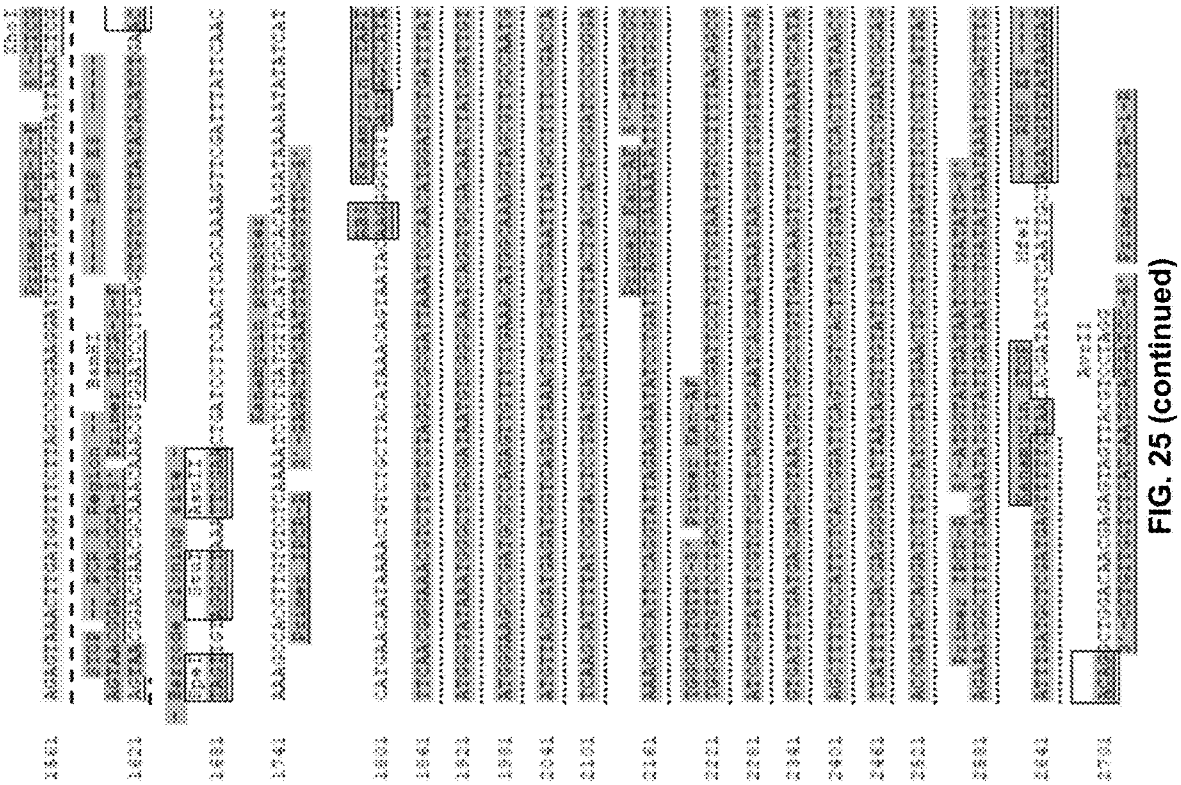

FIG. 25. Annotated sequences of the entire minimal test vector with the hyperactive Tn5-transposase (SEQ ID NO: 6). The Tn5-Tpn [hyper] gene (dashed underline) spans positions 168-1622 with a start codon from positions 165-167 and a stop codon from positions 1623-1625. The E54K mutation spans positions 351-353. The M56A mutation spans positions 357-359. The L372P mutation spans positions 1305-1307. A Tet-35 site spans positions 53-58. A Tet-10 site spans positions 66-71. A BglII restriction site spans positions 1-6. An XbaI restriction site spans positions 124-129. A BamHI restriction site spans positions 1647-1652. The barcode cloning site spanning positions 1679-1702 encompasses three restriction sites, SpeI (1679-1684), StuI (1688-1693), and AsuII (1697-1702). An LHS ES site spans 1658-1676. A ribosome binding site (RBS site spans positions 154-158. A kanamycin resistance gene (dotted underline) spans positions 1854-2653 with a start codon at positions 1851-1853 and a stop codon at positions 2654-2656. An RBS spans positions 1841-1843. An MfeI restriction site spans 2678-2683. An AvrII restriction site spans positions 2729-2734. Additionally, primer sequences displayed in FIG. 25 are listed in Table D.

Figure 26:
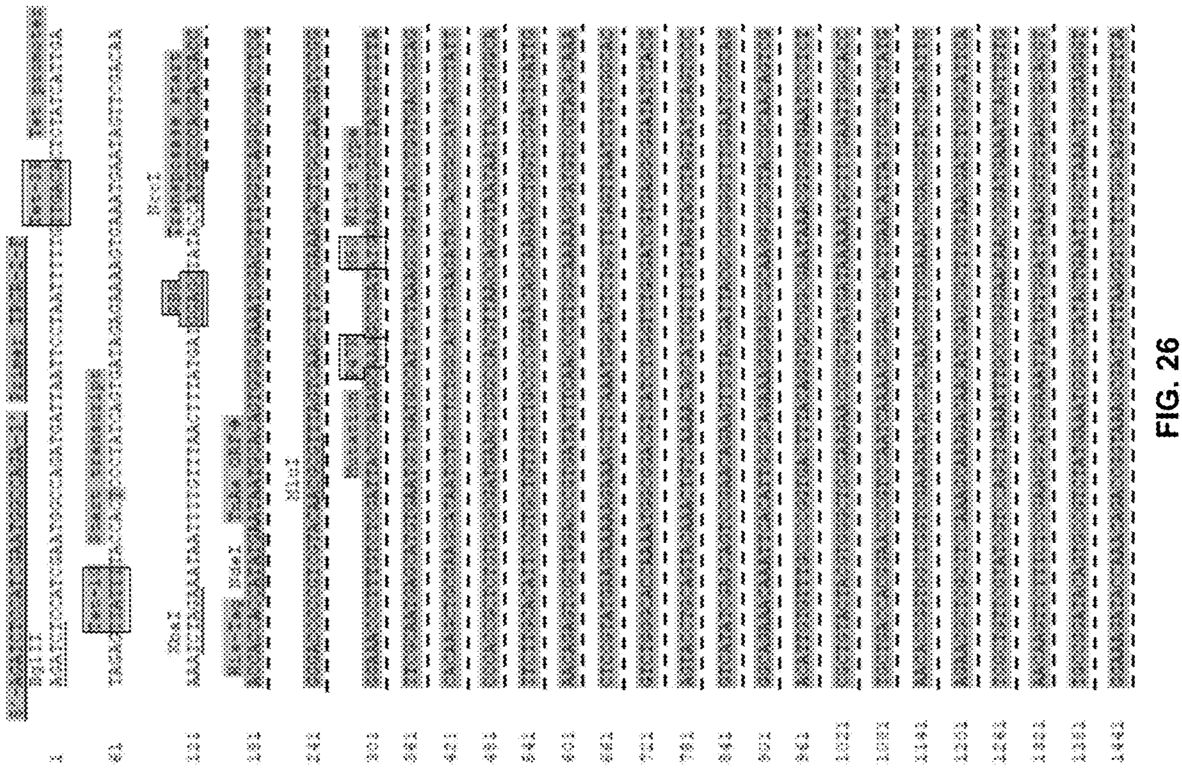
Figure 26:
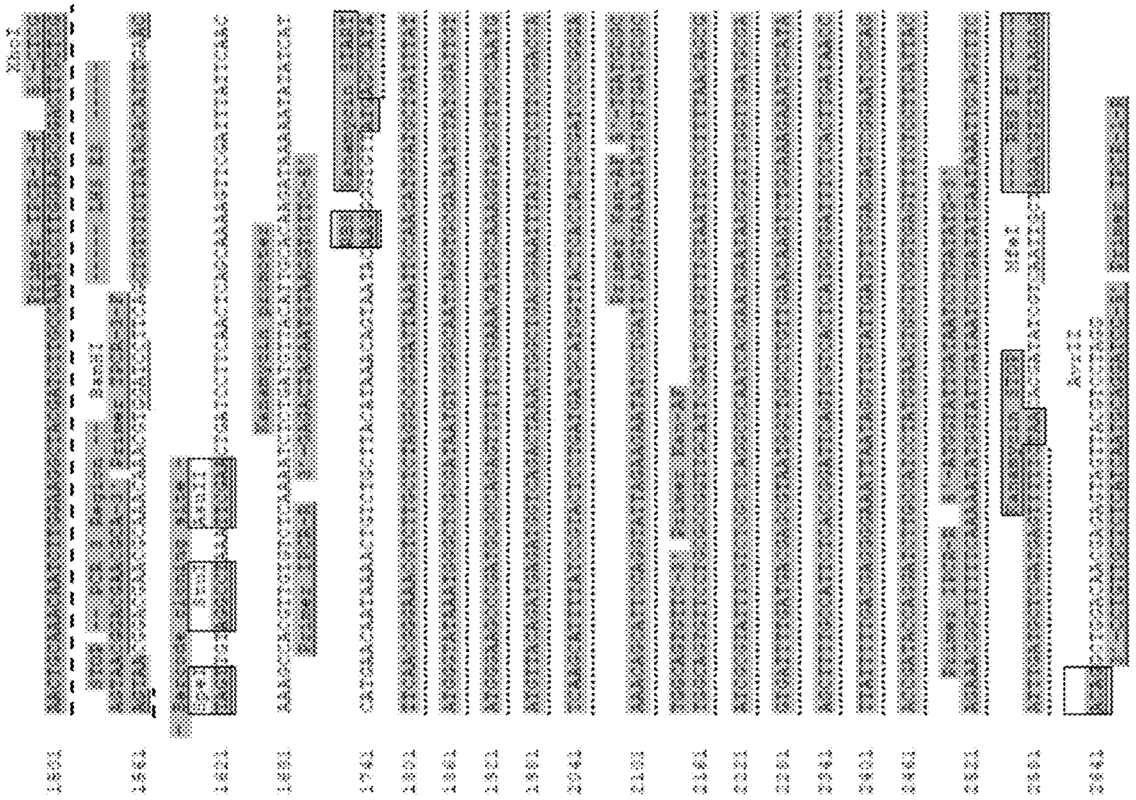

FIG. 26. Annotated sequences of the entire minimal test vector with the P47K-mutant TnAa-transposase (SEQ ID NO: 7). The TnAa-Tpn [P47K] gene (dashed underline) spans positions 168-1562 with at start codon from positions 165-167 and a stop codon from positions 1563-1565. The P47K mutation spans positions 330-332. A Tet-35 site spans positions 53-58. A Tet-10 site spans positions 66-71. A BglII restriction site spans positions 1-6. An XbaI restriction site spans positions 124-129. An NcoI restriction site spans positions 163-168. An MluI restriction site spans positions 258-263. A BamHI restriction site spans positions 1587-1592. The barcode cloning site spanning positions 1679-1702 encompasses three restriction sites, SpeI (1619-1624), StuI (1628-1633), and AsuII (1637-1642). An LHS ES site spans 1598-1616. A ribosome binding site (RBS site spans positions 154-158. A kanamycin resistance gene (dotted underline) spans positions 1794-2603 with a start codon at positions 1791-1793 and a stop codon at positions 2604-2606. An RBS spans positions 1781-1783. An MfeI restriction site spans 2618-2623. An AvrII restriction site spans positions 2636-2641. An RHS ES site spans positions 2626-2644. Additionally, primer sequences displayed in FIG. 26 are listed in Table D.

DETAILED DESCRIPTION

The disclosure provides compositions and high-throughput methods for screening a plurality of transposases in parallel to rapidly and efficiently identify rare mutations that impart or enhance desirable functions of a transposase as a molecular tool for use in, for example, next generation sequencing (NGS). The compositions of the disclosure incorporate a unique identifier (UID) barcode into a transposable nucleic acid that, upon insertion, places the UID barcode in close proximity to the insertion site repeat sequence. By correlating the UID barcode with the nucleic acid sequence of the transposase that moved the transposable nucleic acid containing the UID barcode and by having the UID barcode in close proximity to the insertion site repeat sequence, a minimal length of sequence must be obtained to determine the identity of the one transposase among a plurality of transposases moved the UID barcode and the insertion site preferences of that transposase. The methods of the disclosure are intended to be used for screening millions of mutagenized transposases, which imposes a burden of potentially sequencing billions of insertion sites. The compositions and methods of the disclosure are designed to minimize the sequencing burden while maximizing the information that can be obtained from a single experiment.

Barcode-Assisted Transposase Screening (BATS)

The disclosure provides methods of mutagenesis and screening of a transposase that demonstrates decreased biased target selection compared to a wild type transposase or a known mutant transposase during transposition. Transposases identified by the methods of the disclosure may be used to for Next Generation Sequencing (NGS) application as well as other application in the field of molecular biology.

Transposases subjected to the methods of the disclosure may include any transposase. In certain embodiments, the transposase is derived from *Alishewanella aestuarii*. In certain embodiments, the transposase is a wild type TnAa-transposase (e.g. a transposase having the amino acid sequence of SEQ ID NO: 2) or a mutant TnAa-transposase (e.g. a transposase having the amino acid sequence of any one of SEQ ID NOs: 3-5). In certain embodiments, the transposase is a wild type Tn5-transposase. In certain embodiments, the transposase is a mutant Tn5-transposase having increase transposition activity compared to a wild type Tn5-transposase. In certain embodiments, the transposase is a mutant Tn5-transposase comprising one or more of E54K, M56A and L372P (with the mutant positions according to the numbering of SEQ ID NO: 6). In certain embodiments, the transposase is a mutant Tn5-transposase comprising E54K, M56A and L372P (e.g. a transposase having the amino acid sequence of SEQ ID NO: 1). In certain embodiments, the transposase is a mutant Tn5-transposase having reduced target specificity compared to a wild type Tn5-transposase. In certain embodiments, the transposase is a mutant Tn5-transposase comprising the K212M and having reduced target specificity compared to a wild type Tn5-transposase.

Sequences of exemplary transposases are provided below (mutations are bolded and underlined).

```
Tn5-transposase mutant W125G.
                                                               (SEQ ID NO: 18)
  1   MITSALHRAA DWAKSVFSSA ALGDPRRTAR LVNVAAQLAK YSGKSITISS EGSKAAQEGA

 61   YRFIRNPNVS AEAIRKAGAM QTVKLAQEFP ELLAIEDTTS LSYRHQVAEE LGKLGSIQDK

121   SRGWGVHSVL LLEATTFRTV GLLHQEWWMR PDDPADADEK ESGKWLAAAA TSRLRMGSMM

181   SNVIAVCDRE ADIHAYLQDK LAHNERFVVR SKHPRKDVES GLYLYDHLKN QPELGGYQIS

241   IPQKGVVDKR GKRKNRPARK ASLSLRSGRI TLKQGNITLN AVLAEEINPP KGETPLKWLL

301   LTSEPVESLA QALRVIDIYT HRWRIEEFHK AWKTGAGAER QRMEEPDNLE RMVSILSFVA

361   VRLLQLRESF TPPQALRAQG LLKEAEHVES QSAETVLTPD ECQLLGYLDK GKRKRKEKAG

421   SLQWAYMAIA RLGGFMDSKR TGIASWGALW EGWEALQSKL DGFLAAKDLM AQGIKLE*

Tn5-transposase mutant E146A.
                                                               (SEQ ID NO: 19)
  1   MITSALHRAA DWAKSVFSSA ALGDPRRTAR LVNVAAQLAK YSGKSITISS EGSKAAQEGA

 61   YRFIRNPNVS AEAIRKAGAM QTVKLAQEFP ELLAIEDTTS LSYRHQVAEE LGKLGSIQDK

121   SRGWWVHSVL LLEATTFRTV GLLHQAWWMR PDDPADADEK ESGKWLAAAA TSRLRMGSMM

181   SNVIAVCDRE ADIHAYLQDK LAHNERFVVR SKHPRKDVES GLYLYDHLKN QPELGGYQIS

241   IPQKGVVDKR GKRKNRPARK ASLSLRSGRI TLKQGNITLN AVLAEEINPP KGETPLKWLL

301   LTSEPVESLA QALRVIDIYT HRWRIEEFHK AWKTGAGAER QRMEEPDNLE RMVSILSFVA
```

-continued

```
361    VRLLQLRESF TPPQALRAQG LLKEAEHVES QSAETVLTPD ECQLLGYLDK GKRKRKEKAG
421    SLQWAYMAIA RLGGFMDSKR TGIASWGALW EGWEALQSKL DGFLAAKDLM AQGIKLE*
```

Tn5-transposase mutant E146C.

(SEQ ID NO: 20)

```
1      MITSALHRAA DWAKSVFSSA ALGDPRRTAR LVNVAAQLAK YSGKSITISS EGSKAAQEGA
61     YRFIRNPNVS AEAIRKAGAM QTVKLAQEFP ELLAIEDTTS LSYRHQVAEE LGKLGSIQDK
121    SRGWWVHSVL LLEATTFRTV GLLHQCWWMR PDDPADADEK ESGKWLAAAA TSRLRMGSMM
181    SNVIAVCDRE ADIHAYLQDK LAHNERFVVR SKHPRKDVES GLYLYDHLKN QPELGGYQIS
241    IPQKGVVDKR GKRKNRPARK ASLSLRSGRI TLKQGNITLN AVLAEEINPP KGETPLKWLL
301    LTSEPVESLA QALRVIDIYT HRWRIEEFHK AWKTGAGAER QRMEEPDNLE RMVSILSFVA
361    VRLLQLRESF TPPQALRAQG LLKEAEHVES QSAETVLTPD ECQLLGYLDK GKRKRKEKAG
421    SLQWAYMAIA RLGGFMDSKR TGIASWGALW EGWEALQSKL DGFLAAKDLM AQGIKLE*
```

Tn5-transposase mutant E146N.

(SEQ ID NO: 21)

```
1      MITSALHRAA DWAKSVFSSA ALGDPRRTAR LVNVAAQLAK YSGKSITISS EGSKAAQEGA
61     YRFIRNPNVS AEAIRKAGAM QTVKLAQEFP ELLAIEDTTS LSYRHQVAEE LGKLGSIQDK
121    SRGWWVHSVL LLEATTFRTV GLLHQNWWMR PDDPADADEK ESGKWLAAAA TSRLRMGSMM
181    SNVIAVCDRE ADIHAYLQDK LAHNERFVVR SKHPRKDVES GLYLYDHLKN QPELGGYQIS
241    IPQKGVVDKR GKRKNRPARK ASLSLRSGRI TLKQGNITLN AVLAEEINPP KGETPLKWLL
301    LTSEPVESLA QALRVIDIYT HRWRIEEFHK AWKTGAGAER QRMEEPDNLE RMVSILSFVA
361    VRLLQLRESF TPPQALRAQG LLKEAEHVES QSAETVLTPD ECQLLGYLDK GKRKRKEKAG
421    SLQWAYMAIA RLGGFMDSKR TGIASWGALW EGWEALQSKL DGFLAAKDLM AQGIKLE*
```

Tn5-transposase mutant E1465.

(SEQ ID NO: 22)

```
1      MITSALHRAA DWAKSVFSSA ALGDPRRTAR LVNVAAQLAK YSGKSITISS EGSKAAQEGA
61     YRFIRNPNVS AEAIRKAGAM QTVKLAQEFP ELLAIEDTTS LSYRHQVAEE LGKLGSIQDK
121    SRGWWVHSVL LLEATTFRTV GLLHQSWWMR PDDPADADEK ESGKWLAAAA TSRLRMGSMM
181    SNVIAVCDRE ADIHAYLQDK LAHNERFVVR SKHPRKDVES GLYLYDHLKN QPELGGYQIS
241    IPQKGVVDKR GKRKNRPARK ASLSLRSGRI TLKQGNITLN AVLAEEINPP KGETPLKWLL
301    LTSEPVESLA QALRVIDIYT HRWRIEEFHK AWKTGAGAER QRMEEPDNLE RMVSILSFVA
361    VRLLQLRESF TPPQALRAQG LLKEAEHVES QSAETVLTPD ECQLLGYLDK GKRKRKEKAG
421    SLQWAYMAIA RLGGFMDSKR TGIASWGALW EGWEALQSKL DGFLAAKDLM AQGIKLE*
```

Tn5-transposase mutant P214S.

(SEQ ID NO: 23)

```
1      MITSALHRAA DWAKSVFSSA ALGDPRRTAR LVNVAAQLAK YSGKSITISS EGSKAAQEGA
61     YRFIRNPNVS AEAIRKAGAM QTVKLAQEFP ELLAIEDTTS LSYRHQVAEE LGKLGSIQDK
121    SRGWWVHSVL LLEATTFRTV GLLHQEWWMR PDDPADADEK ESGKWLAAAA TSRLRMGSMM
181    SNVIAVCDRE ADIHAYLQDK LAHNERFVVR SKHSRKDVES GLYLYDHLKN QPELGGYQIS
241    IPQKGVVDKR GKRKNRPARK ASLSLRSGRI TLKQGNITLN AVLAEEINPP KGETPLKWLL
301    LTSEPVESLA QALRVIDIYT HRWRIEEFHK AWKTGAGAER QRMEEPDNLE RMVSILSFVA
361    VRLLQLRESF TPPQALRAQG LLKEAEHVES QSAETVLTPD ECQLLGYLDK GKRKRKEKAG
421    SLQWAYMAIA RLGGFMDSKR TGIASWGALW EGWEALQSKL DGFLAAKDLM AQGIKLE*
```

-continued

Tn5-transposase mutant G251A.

(SEQ ID NO: 24)

```
  1  MITSALHRAA DWAKSVFSSA ALGDPRRTAR LVNVAAQLAK YSGKSITISS EGSKAAQEGA
 61  YRFIRNPNVS AEAIRKAGAM QTVKLAQEFP ELLAIEDTTS LSYRHQVAEE LGKLGSIQDK
121  SRGWWVHSVL LLEATTFRTV GLLHQEWWMR PDDPADADEK ESGKWLAAAA TSRLRMGSMM
181  SNVIAVCDRE ADIHAYLQDK LAHNERFVVR SKHSRKDVES GLYLYDHLKN QPELGGYQIS
241  IPQKGVVDKR AKRKNRPARK ASLSLRSGRI TLKQGNITLN AVLAEEINPP KGETPLKWLL
301  LTSEPVESLA QALRVIDIYT HRWRIEEFHK AWKTGAGAER QRMEEPDNLE RMVSILSFVA
361  VRLLQLRESF TPPQALRAQG LLKEAEHVES QSAETVLTPD ECQLLGYLDK GKRKRKEKAG
421  SLQWAYMAIA RLGGFMDSKR TGIASWGALW EGWEALQSKL DGFLAAKDLM AQGIKLE*
```

"Hyperactive" Tn5-transposase (E54K M56A L372P).

(SEQ ID NO: 1)

```
  1  MITSALHRAA DWAKSVFSSA ALGDPRRTAR LVNVAAQLAK YSGKSITISS EGSKAAQEGA
 61  YRFIRNPNVS AEAIRKAGAM QTVKLAQEFP ELLAIEDTTS LSYRHQVAEE LGKLGSIQDK
121  SRGWWVHSVL LLEATTFRTV GLLHQEWWMR PDDPADADEK ESGKWLAAAA TSRLRMGSMM
181  SNVIAVCDRE ADIHAYLQDK LAHNERFVVR SKHPRKDVES GLYLYDHLKN QPELGGYQIS
241  IPQKGVVDKR GKRKNRPARK ASLSLRSGRI TLKQGNITLN AVLAEEINPP KGETPLKWLL
301  LTSEPVESLA QALRVIDIYT HRWRIEEFHK AWKTGAGAER QRMEEPDNLE RMVSILSFVA
361  VRLLQLRESF TPPQALRAQG LLKEAEHVES QSAETVLTPD ECQLLGYLDK GKRKRKEKAG
421  SLQWAYMAIA RLGGFMDSKR TGIASWGALW EGWEALQSKL DGFLAAKDLM AQGIKLE*
```

Wild-type TnAa-transposase (no mutations).

(SEQ ID NO: 2)

```
  1  MNNAQWAKST FGQADLGDPR RTTRLVKLAE TLANDPGKPF VSITQSPADM EGAYRFIRNE
 61  HVNADAIAKA GYLVTAAQAA KHNLLLALED TTAITYSHRS VRDELGHVNQ GNNYRGILAH
121  SVLLFAPEQQ ELVGLIEQSR WTRDISTRGK KHVRTQTPYE EKESFKWQSA SVNLSARLGT
181  KMADVISVCD READIYEYLQ YKLSKQHRFV VRSMQSRHIE QSEQKLYDYA AGLESAGQKQ
241  IHIAQKGGRK ARTATVDIVF APVTLQVPAN KRGESLSLYY VGCEERADDK NALNWHLLTT
301  EPVQSKADAL NIIRYYEHRW LVEEYHKAWK TDGTDIENAR LQSKDNIERL VTISAFIAVR
361  IVQLKFAREQ PDEISCEQVL SPKAWKLLWI KRVSRTLPDT VPSMKWAYTE LAKLGGWKDT
421  KQTGKASVKV LWQGWFKLQT ILEGYDLAKS LEADLLE*
```

Double mutant TnAa-transposase (P47K M50A).

(SEQ ID NO: 3)

```
  1  MNNAQWAKST FGQADLGDPR RTTRLVKLAE TLANDPGKPF VSITQSKADA EGAYRFIRNE
 61  HVNADAIAKA GYLVTAAQAA KHNLLLALED TTAITYSHRS VRDELGHVNQ GNNYRGILAH
121  SVLLFAPEQQ ELVGLIEQSR WTRDISTRGK KHVRTQTPYE EKESFKWQSA SVNLSARLGT
181  KMADVISVCD READIYEYLQ YKLSKQHRFV VRSMQSRHIE QSEQKLYDYA AGLESAGQKQ
241  IHIAQKGGRK ARTATVDIVF APVTLQVPAN KRGESLSLYY VGCEERADDK NALNWHLLTT
301  EPVQSKADAL NIIRYYEHRW LVEEYHKAWK TDGTDIENAR LQSKDNIERL VTISAFIAVR
361  IVQLKFAREQ PDEISCEQVL SPKAWKLLWI KRVSRTLPDT VPSMKWAYTE LAKLGGWKDT
421  KQTGKASVKV LWQGWFKLQT ILEGYDLAKS LEADLLE*
```

Single mutant TnAa-transposase (M50A).

(SEQ ID NO: 4)

```
  1  MNNAQWAKST FGQADLGDPR RTTRLVKLAE TLANDPGKPF VSITQSPADA EGAYRFIRNE
 61  HVNADAIAKA GYLVTAAQAA KHNLLLALED TTAITYSHRS VRDELGHVNQ GNNYRGILAH
121  SVLLFAPEQQ ELVGLIEQSR WTRDISTRGK KHVRTQTPYE EKESFKWQSA SVNLSARLGT
181  KMADVISVCD READIYEYLQ YKLSKQHRFV VRSMQSRHIE QSEQKLYDYA AGLESAGQKQ
```

-continued

241 IHIAQKGGRK ARTATVDIVF APVTLQVPAN KRGESLSLYY VGCEERADDK NALNWHLLTT

301 EPVQSKADAL NIIRYYEHRW LVEEYHKAWK TDGTDIENAR LQSKDNIERL VTISAFIAVR

361 IVQLKFAREQ PDEISCEQVL SPKAWKLLWI KRVSRTLPDT VPSMKWAYTE LAKLGGWKDT

421 KQTGKASVKV LWQGWFKLQT ILEGYDLAKS LEADLLE*

Single mutant TnAa-transposase (P47K).

(SEQ ID NO: 5)

1 MNNAQWAKST FGQADLGDPR RTTRLVKLAE TLANDPGKPF VSITQSKADM EGAYRFIRNE

61 HVNADAIAKA GYLVTAAQAA KHNLLLALED TTAITYSHRS VRDELGHVNQ GNNYRGILAH

121 SVLLFAPEQQ ELVGLIEQSR WTRDISTRGK KHVRTQTPYE EKESFKWQSA SVNLSARLGT

181 KMADVISVCD READIYEYLQ YKLSKQHRFV VRSMQSRHIE QSEQKLYDYA AGLESAGQKQ

241 IHIAQKGGRK ARTATVDIVF APVTLQVPAN KRGESLSLYY VGCEERADDK NALNWHLLTT

301 EPVQSKADAL NIIRYYEHRW LVEEYHKAWK TDGTDIENAR LQSKDNIERL VTISAFIAVR

361 IVQLKFAREQ PDEISCEQVL SPKAWKLLWI KRVSRTLPDT VPSMKWAYTE LAKLGGWKDT

421 KQTGKASVKV LWQGWFKLQT ILEGYDLAKS LEADLLE*

Minimal test vector carrying “hyperactive” Tn5-transposase
(E54K M56A L372P).

(SEQ ID NO: 6)

1 AGATCTCCAT CGAATGGCCA GATGATTAAT TCCTAATTTT TGTTGACACT CTATCATTGA

61 TAGAGTTATT TTACCACTCC CTATCAGTGA TAGAGAAAAG TGAAATGAAT AGTTCGACAA

121 AAATCTAGAA ATAATTTTGT TTAACTTTAT GATGGAGCA TACCATGGCC CACCACCACC

181 ACCACCACCA TATGATCACC TCTGCCCTGC ATCGCGCGGC TGATTGGGCG AAATCCGTCT

241 TCTCATCAGC GGCACTGGGC GACCCGCGGC GTACCGCGCG TCTGGTTAAT GTGGCGGCTC

301 AGCTGGCTAA ATACAGCGGG AAAAGTATTA CGATCAGTAG CGAAGGGTCA AAAGCGGCAC

361 AAGAAGGAGC ATATCGTTTT ATCCGCAATC CGAATGTCTC CGCCGAGGCC ATCCGCAAAG

421 CGGGCGCCAT GCAAACAGTG AAATTGGCAC AGGAATTCCC GGAACTGTTG GCCATTGAGG

481 ATACCACATC GCTTAGCTAT CGTCACCAAG TCGCAGAAGA ACTGGGAAAA TTAGGCTCTA

541 TTCAGGATAA ATCTCGTGGT TGGTGGGTGC ACTCTGTTTT ATTACTGGAA GCGACCACCT

601 TCCGTACCGT GGGGCTGCTG CATCAGGAAT GGTGGATGCG GCCAGATGAC CCAGCGGACG

661 CCGACGAAAA AGAATCTGGT AAATGGTTGG CGGCTGCGGC GACCTCGCGC CTCCGTATGG

721 GTTCCATGAT GAGCAACGTC ATTGCAGTGT GCGATCGCGA AGCTGATATT CATGCGTACC

781 TTCAGGATAA ACTGGCGCAC AACGAGCGCT TCGTCGTGCG CAGCAAACAT CCCCGTAAGG

841 ACGTCGAATC AGGTCTGTAT TTGTATGACC ATCTGAAAAA TCAGCCGGAA CTGGGAGGAT

901 ATCAAATTTC GATCCCGCAG AAGGGAGTCG TGGATAAACG CGGCAAACGT AAAAATCGTC

961 CAGCTCGCAA AGCCAGCTTG AGTTTGCGCA GCGGTCGTAT TACCCTCAAA CAGGGGAACA

1021 TTACCCTGAA CGCTGTACTC GCGGAGGAGA TCAATCCCCC CAAGGGCGAA ACACCGTTAA

1081 AATGGTTACT GTTAACATCT GAACCCGTTG AGAGTCTGGC TCAAGCACTG CGCGTGATCG

1141 ATATTTACAC CCATCGCTGG CGCATTGAAG AATTCCATAA AGCATGGAAG ACCGGCGCGG

1201 GCGCGGAACG CCAACGTATG GAAGAACCGG ATAACCTCGA ACGGATGGTC AGCATCCTGA

1261 GCTTTGTTGC GGTACGTCTG CTTCAGCTGC GTGAAAGCTT TACGCCACCG CAGGCGCTGC

1321 GCGCGCAGGG CCTCCTGAAA GAAGCGGAGC ATGTTGAGTC ACAGAGCGCA GAAACCGTTC

1381 TGACTCCCGA CGAATGTCAA CTCCTGGGCT ATCTGGACAA GGGGAAACGT AAACGTAAAG

1441 AGAAAGCAGG CAGCCTCCAG TGGGCATATA TGGCGATCGC ACGGTTAGGA GGCTTCATGG

1501 ACAGCAAACG TACGGGTATT GCGAGCTGGG GTGCGCTGTG GGAAGGCTGG GAAGCTTTGC

-continued

1561 AGAGTAAACT TGATGGTTTC TTAGCCGCGA AGGATCTGAT GGCACAGGGG ATTAAACTCG

1621 AGTAACGGAC GAACGCAAAC AAACGTGGAT CCTTCAGCTG TCTCTTATAC ACATCTGAAC

1681 TAGTTGTAGG CCTAAATTCG AACTGATCCT TCAACTCAGC AAAAGTTCGA TTTATTCAAC

1741 AAAGCCACGT TGTGTCTCAA AATCTCTGAT GTTACATTGC ACAAGATAAA AATATATCAT

1801 CATGAACAAT AAAACTGTCT GCTTACATAA ACAGTAATAC AAGGGGTGTT ATGAGCCATA

1861 TTCAACGGGA AACGTCTTGC TCTAGGCCGC GATTAAATTC CAACATGGAT GCTGATTTAT

1921 ATGGGTATAA ATGGGCTCGC GATAATGTCG GGCAATCAGG TGCGACAATC TATCGATTGT

1981 ATGGGAAGCC CGATGCGCCA GAGTTGTTTC TGAAACATGG CAAAGGTAGC GTTGCCAATG

2041 ATGTTACAGA TGAGATGGTC AGACTAAACT GGCTGACGGA ATTTATGCCT CTTCCGACCA

2101 TCAAGCATTT TATCCGTACT CCTGATGATG CATGGTTACT CACCACTGCG ATCCCCGGGA

2161 AAACAGCATT CCAGGTATTA GAAGAATATC CTGATTCAGG TGAAAATATT GTTGATGCGC

2221 TGGCAGTGTT CCTGCGCCGG TTGCATTCGA TTCCTGTTTG TAATTGTCCT TTTAACAGCG

2281 ATCGCGTATT TCGTCTCGCT CAGGCGCAAT CACGAATGAA TAACGGTTTG GTTGATGCGA

2341 GTGATTTTGA TGACGAGCGT AATGGCTGGC CTGTTGAACA AGTCTGGAAA GAAATGCATA

2401 AGCTTTTGCC ATTCTCACCG GATTCAGTCG TCACTCATGG TGATTTCTCA CTTGATAACC

2461 TTATTTTTGA CGAGGGGAAA TTAATAGGTT GTATTGATGT TGGACGAGTC GGAATCGCAG

2521 ACCGATACCA GGATCTTGCC ATCCTATGGA ACTGCCTCGG TGAGTTTTCT CCTTCATTAC

2581 AGAAACGGCT TTTTCAAAAA TATGGTATTG ATAATCCTGA TATGAATAAA TTGCAGTTTC

2641 ATTTGATGCT CGATGAGTTT TTCTAACACG ATATCGTCAA TTGCTAGATG TGTATAAGAG

2701 ACAGGCTGGA CAACGAGAGT AGTTACGTCC TAGG

Minimal test vector carrying single mutant TnAa-transposase (P47K).

(SEQ ID NO: 7)

1 AGATCTCCAT CGAATGGCCA GATGATTAAT TCCTAATTTT TGTTGACACT CTATCATTGA

61 TAGAGTTATT TTACCACTCC CTATCAGTGA TAGAGAAAAG TGAAATGAAT AGTTCGACAA

121 AAATCTAGAA ATAATTTTGT TTAACTTTAT GATGGAGCTA TACCATGGCC CACCACCACC

181 ACCACCACCA TATGAATAAT GCACAGTGGG CGAAATCGAC GTTTGGTCAG GCCGACCTCG

241 GGGACCCCCG TCGTACAACG CGTTTAGTCA AGCTTGCCGA AACACTTGCC AACGATCCGG

301 GGAAACCCTT TGTCTCGATT ACCCAGAGCA AAGCCGATAT GGAAGGTGCC TATCGTTTTA

361 TTCGCAATGA GCATGTGAAT GCTGATGCCA TTGCTAAAGC CGGCTACCTG GTGACCGCAG

421 CACAAGCTGC GAAGCATAAT CTGCTTCTGG CACTTGAAGA TACCACGGCC ATCACCTATT

481 CCCACCGCTC TGTGCGCGAT GAACTCGGCC ATGTTAACCA GGGTAATAAT TACCGTGGCA

541 TTCTTGCACA TTCCGTGCTG TTGTTTGCCC CGGAACAGCA AGAGCTGGTC GGACTGATTG

601 AACAGAGTCG CTGGACCCGT GATATTTCAA CCCGTGGCAA AAAGCATGTC CGTACACAAA

661 CTCCGTATGA AGAAAAAGAA AGCTTCAAAT GGCAGTCTGC TTCAGTTAAT CTGTCGGCAC

721 GTCTGGGCAC CAAAATGGCG GACGTCATCT CGGTTTGCGA TCGTGAGGCG GATATCTACG

781 AGTACCTGCA GTACAAACTG TCAAAACAGC ATCGTTTTGT AGTACGTAGT ATGCAGTCCC

841 GTCATATCGA GCAGTCCGAA CAGAAGTTGT ACGATTACGC CGCGGGTTTG GAATCGGCAG

901 GGCAGAAACA AATTCACATT GCGCAGAAAG GGGGCCGCAA GGCGCGTACC GCAACAGTCG

961 ACATTGTGTT TGCCCCGGTG ACTTTACAGG TGCCGGCGAA TAAACGTGGT GAATCCCTCT

1021 CGCTGTACTA CGTGGGCTGC GAAGAACGCG CTGATGATAA AAATGCTTTG AATTGGCACC

1081 TGCTGACCAC GGAACCCGTC CAATCAAAAG CGGACGCACT GAACATTATT CGCTACTATG

-continued

```
1141    AACACCGGTG GCTGGTCGAA GAATACCACA AAGCCTGGAA AACCGACGGT ACTGACATTG
1201    AGAACGCTCG CCTCCAAAGC AAAGACAACA TCGAGCGCTT GGTAACGATC TCGGCATTCA
1261    TCGCTGTTCG TATCGTCCAG CTGAAATTTG CCCGGGAACA ACCGGATGAA ATCAGTTGTG
1321    AACAAGTTCT TTCTCCGAAG GCATGGAAAT TACTGTGGAT TAAACGTGTG AGCCGCACGT
1381    TGCCGGATAC AGTGCCGTCT ATGAAATGGG CCTATACTGA ATTGGCTAAA CTGGGAGGGT
1441    GGAAAGATAC CAAACAGACC GGTAAAGCGA GTGTTAAGGT CCTCTGGCAG GGTTGGTTCA
1501    AACTGCAAAC AATCTTGGAA GGCTACGATC TTGCCAAATC CTTGGAAGCG GACTTGCTCG
1561    AGTAACGGAC GAACGCAAAC AAACGTGGAT CCTTCAGCTG TCTCTTATAC ACATCTGAAC
1621    TAGTTGTAGG CCTAAATTCG AACTGATCCT TCAACTCAGC AAAAGTTCGA TTTATTCAAC
1681    AAAGCCACGT TGTGTCTCAA AATCTCTGAT GTTACATTGC ACAAGATAAA AATATATCAT
1741    CATGAACAAT AAAACTGTCT GCTTACATAA ACAGTAATAC AAGGGGTGTT ATGAGCCATA
1801    TTCAACGGGA AACGTCTTGC TCTAGGCCGC GATTAAATTC CAACATGGAT GCTGATTTAT
1861    ATGGGTATAA ATGGGCTCGC GATAATGTCG GGCAATCAGG TGCGACAATC TATCGATTGT
1921    ATGGGAAGCC CGATGCGCCA GAGTTGTTTC TGAAACATGG CAAAGGTAGC GTTGCCAATG
1981    ATGTTACAGA TGAGATGGTC AGACTAAACT GGCTGACGGA ATTTATGCCT CTTCCGACCA
2041    TCAAGCATTT TATCCGTACT CCTGATGATG CATGGTTACT CACCACTGCG ATCCCCGGGA
2101    AAACAGCATT CCAGGTATTA GAAGAATATC CTGATTCAGG TGAAAATATT GTTGATGCGC
2161    TGGCAGTGTT CCTGCGCCGG TTGCATTCGA TTCCTGTTTG TAATTGTCCT TTTAACAGCG
2221    ATCGCGTATT TCGTCTCGCT CAGGCGCAAT CACGAATGAA TAACGGTTTG GTTGATGCGA
2281    GTGATTTTGA TGACGAGCGT AATGGCTGGC CTGTTGAACA AGTCTGGAAA GAAATGCATA
2341    AGCTTTTGCC ATTCTCACCG GATTCAGTCG TCACTCATGG TGATTTCTCA CTTGATAACC
2401    TTATTTTTGA CGAGGGGAAA TTAATAGGTT GTATTGATGT TGGACGAGTC GGAATCGCAG
2461    ACCGATACCA GGATCTTGCC ATCCTATGGA ACTGCCTCGG TGAGTTTTCT CCTTCATTAC
2521    AGAAACGGCT TTTTCAAAAA TATGGTATTG ATAATCCTGA TATGAATAAA TTGCAGTTTC
2581    ATTTGATGCT CGATGAGTTT TTCTAACACG ATATCGTCAA TTGCTAGATG TGTATAAGAG
2641    ACAGGCTGGA CAACGAGAGT AGTTACGTCC TAGG
```

Wild Type Tn5-transposase.

(SEQ ID NO: 17)

```
  1    MITSALHRAA DWAKSVFSSA ALGDPRRTAR LVNVAAQLAK YSGKSITISS EGSEAMQEGA
 61    YRFIRNPNVS AEAIRKAGAM QTVKLAQEFP ELLAIEDTTS LSYRHQVAEE LGKLGSIQDK
121    SRGWWVHSVL LLEATTFRTV GLLHQEWWMR PDDPADADEK ESGKWLAAAA TSRLRMGSMM
181    SNVIAVCDRE ADIHAYLQDK LAHNERFVVR SKHPRKDVES GLYLYDHLKN QPELGGYQIS
241    IPQKGVVDKR GKRKNRPARK ASLSLRSGRI TLKQGNITLN AVLAEEINPP KGETPLKWLL
301    LTSEPVESLA QALRVIDIYT HRWRIEEFHK AWKTGAGAER QRMEEPDNLE RMVSILSFVA
361    VRLLQLRESF TLPQALRAQG LLKEAEHVES QSAETVLTPD ECQLLGYLDK GKRKRKEKAG
421    SLQWAYMAIA RLGGFMDSKR TGIASWGALW EGWEALQSKL DGFLAAKDLM AQGIKI
```

An existing method to identify a mutant transposase having altered insertion bias compared to a wild type transposase may comprise the steps of: (1) Generating a plurality of mutant transposases; (2) Inserting a first mutant transposase of the plurality of mutant transposases into a host organism cell; (3) Inducing at least 10 transpositions mediated by the first mutant transposase; (4) Identifying an insertion bias of the first mutant transposase; and (5) Repeating steps (2) through (4) with a second and subsequent mutant transposase until a mutant transposase having a different insertional bias from the first mutant transposase is identified. The mutation(s) that the first, second, and subsequent mutant transposases comprise are subsequently characterized by sequencing each of the mutant transposases. Performing steps (1) through (4) is not problematic and could be achieved in a variety of ways; step 1 is a standard gene mutagenesis methodology and steps 2-4 are standard transposon-based insertion mutagenesis (gene knock out)

methodology. Mutagenesis techniques are well established. Mutagenesis can be random or can be directed to specific positions in the transposase gene. Mutagenesis can include the creation of, for example, point mutations, deletions and/or insertions. The transposase is typically incorporated into a transposon, and this is usually placed within a vector (for example a plasmid or virus). The vector may or may not have a replication origin that will work in the target host (for example, a strain of *E. coli*). The transposon-carrying vector is then used to transform the host (for example, by transfection or by using electro- or chemically-competent cells). Once in the host, the transposase is typically expressed from either the natural or cloned artificial expression signals. The transposase proteins then associate with the transposon end-sequences and initiate transposition. The test-transposon would typically carry a selectable marker (such as an antibiotic resistance gene). In cases where the vector donor DNA cannot replicate, only clones in which the transposon and its marker have inserted by transposition into a replication proficient target (a different replication-competent plasmid or the chromosome) will be viable under selection conditions (such as the presence of the appropriate antibiotic). These surviving clones are then investigated with regard to the transposon insertion bias. This could be done by identifying the insertion site by hybridization capture, Anchored Multiplex PCR (2014, Zheng et al. Nature Medicine, 20, p 1479-1484) or inverse PCR, followed by sequencing. If enough insertion sites are characterized then an insertion-site consensus sequence could be derived and the insertion bias (and possible variations from the original wild-type) could be established.

The practical limitation lies in step (5). The very rare clones are the clones in which the insertion bias will have been changed as desired (among the many that are unaffected or inactive). In order to find these very rare clones, a significantly greater number of clones must be screened, for example, as described in steps 1-4 above. Current methods of achieving screening large numbers of clones for not only a difference in insertion bias, but a desired change in insertion bias (i.e. step 5) are labor intensive and low throughput in nature, and, therefore, unlikely to result in the identification of many useful clones, even with the expenditure of significant time and many resources.

The methods of the disclosure provide a solution to the long-felt and unmet need for a means to screen large numbers of clones to identify rare mutations in a transposase. Specifically, the disclosure provides a method to screen large numbers of mutant transposases in parallel, such that sufficient numbers of clones, and sufficient numbers of insertion events are screened, to identify those mutant transposases (and the specific mutations that they carry) that display different transposase activity and different insertion site bias, compared to the wild type. Furthermore, the methods of the disclosure may be used to identify those mutant transposases (and the specific mutations that they carry) that display not only different transposase activity and/or different insertion site bias, compared to the wild type, but a desired transposase activity (e.g. hyperactivity) and a desired insertion site bias (e.g. reduced insertion site bias), compared to wild type.

An insertion bias consensus for a wild type transposase can be derived by identifying and sequencing a sufficient number of transposon insertion sites. By sequencing enough insertion sites from transposition driven by a mutant transposon, the insertion bias for that mutant can be identified and compared to the wild type version of the transposon. Derivation of an insertion site consensus and identification of any given mutant transposase's insertion bias compared to the wild type version of that transposase may be simultaneously or sequentially. If these procedures are performed simultaneously and in the same screening experiment, cross-contamination between samples must be prevented. If these procedures are performed simultaneously and in the same screening experiment, then it is also important that, at every insertion site, both the entire transposase and the insertion site are sequenced to identify which wild type or mutant transposase drove insertion at which site. This parallel screening method may be performed with a mixture of thousands (or even millions) of different mutant transposons, provided the sequencing power to characterize each of insertion sites (could be billions) and each of the mutant transposase inserted at each one (could be billions). Unfortunately such power is lacking; the requirement of sequencing the whole transposase gene (about 1.5 kb) at every insertion site limits this approach.

To solve this problem, the sequencing burden imposed by the size of the transposase could be reduced. To this end, a library of mutant transposases could be generated such that each mutant transposase gene is tagged with a short (15-25 bp) unique-identifier (UID) sequence, or barcode. If the tagged-mutant library was sequenced prior to use in the transposition experiment, such that the UID barcode associated with each mutant was known, then only the barcode would have to be sequenced to identify the mutant transposase. If the barcode is positioned such that it appeared adjacent to the insertion site after transposition, then a single short sequencing read could cover both the barcode and the insertion site. Current NGS methodologies could, therefore, deliver information on hundreds of millions of insertions and the identity and mutations carried by the mutant transposase that drove each one of them.

By using a UID barcode, the transposase itself would not even have to be carried to the insertion site, only the barcode would need to be inserted. The transposase can be expressed from a gene located outside of the region bracketed by the transposon end-sequences. The transposase protein forms an ES-transposase complex and causes the intervening region to be excised and inserted elsewhere. If the intervening region carries the UID barcode, it would be transposed to the new site.

The UID-containing insertion sites need to be identified and sequenced. The first step would be identifying and isolating the clones in which transposition has occurred. In principle, the method is the same as described in steps 2-4 of the "existing" above. A selectable marker can be located between the end-sequences, within loop region, such that the selectable marker will also be transposed to the new insertion site, along with the UID barcode. This DNA-construct comprising a UID barcode and a selectable marker that is bracketed with an end-sequence at each end is referred to herein as a mobilisable and selectable barcode region. It requires the expression of a separate transposase gene for functionality (FIG. 7).

The basic methodology of transposase mutant barcode transposition and screening is outlined in FIG. 8. Initially a library of mutant transposases, each linked to a mobilisable and selectable UID is generated and sequenced. The host bacterium is transformed with the library, and each mutant transposase is transiently expressed, the dimeric complex is formed and the mobilisable, selectable UID is excised to insert into the chromosome. The bacteria therefore become antibiotic resistant and can be selected. Each insertion site and barcode is then sequenced by NGS. Many insertion sites are sequenced for each barcode (in other words, for each mutant), so it is possible to determine a consensus sequence for the insertion site and to relate that to a particular mutant transposase.

In the example shown in FIG. 8 (panel 6), only one end of the insertion site is sequenced. Methods to achieve this are shown in FIGS. 9(A) and 9(C); these involve excising one end of the insertion site, and then isolating the required region by either inversion PCR or hybrid capture. For the transposase of Tn5 this would be sufficient to generate a consensus, as it is known that the insertion creates a 9 bp repeat. TnAa-Tpn, however, appears to create the staggered cuts with a variety of spaces between them. In this case, both ends of the insertion have to be sequenced, so that the correct alignment can be made.

A method to achieve this is shown in FIG. 9(B). In this instance, the whole insertion site is excised and circularized, then inversion-PCR is applied to amplify both insertion ends on one amplicon, which is then sequenced.

Transposition Mechanism and Tagmentation

Figure 1:
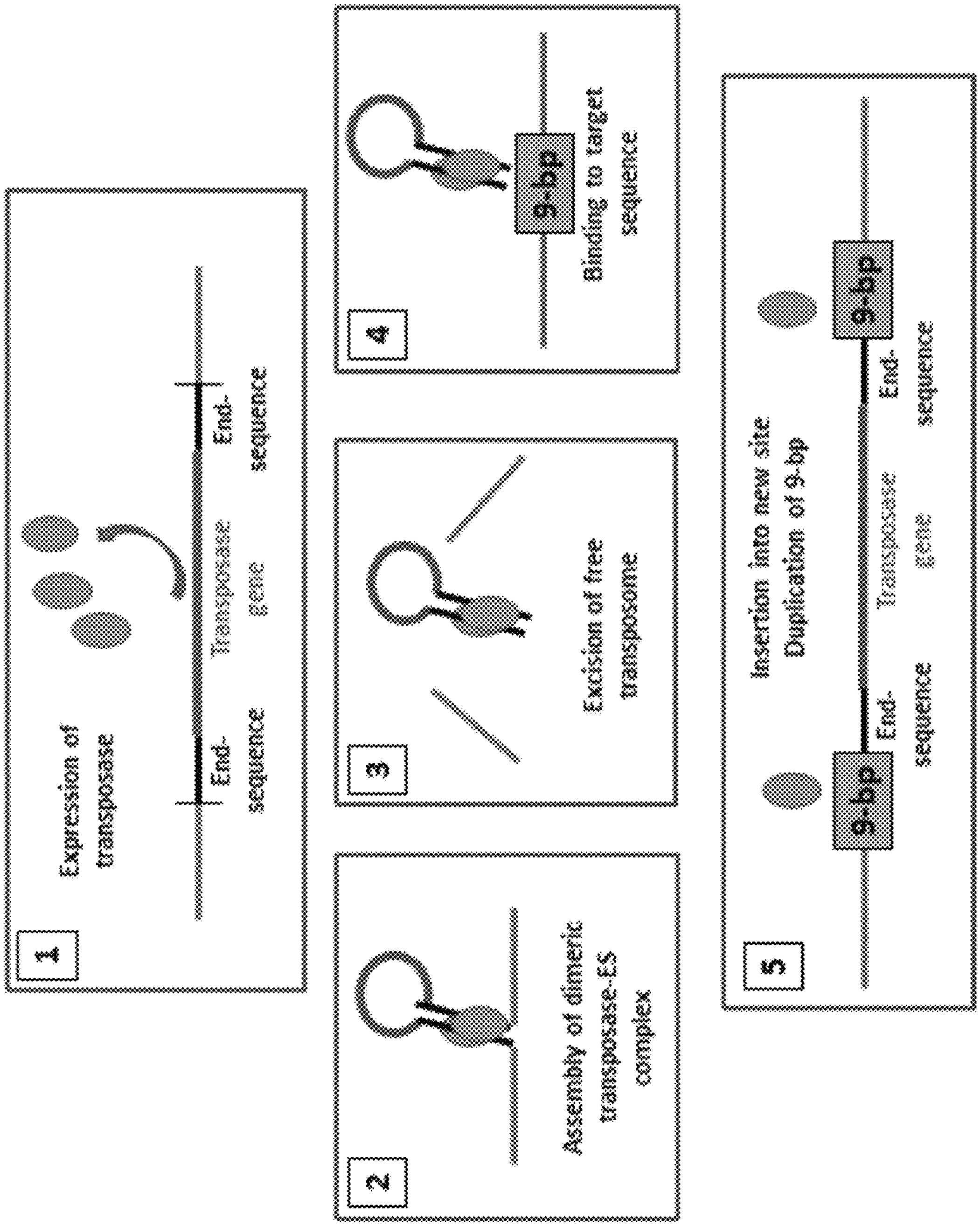
FIG. 1 is a series of schematic diagrams depicting a cut and paste mechanism of transposition of the Tn5 transposase. (1) The transposon is originally located in the donor DNA (blue); it comprises the transposase gene (green) surrounded by the two inverted repeat end-sequences (black). Expression of the transposase initiates transposition. (2) A transposase molecule (orange oval) binds to each end of the transposon at the end-sequences, and these dimerize to form a complex in which the transposon forms a looped structure. (3) The complex is excised from the donor DNA to form a free transposome, which carries the whole transposon loop. (4) The transposome binds to the target DNA (red), covering a 9-bp that will ultimately be duplicated. (5) The target is cut on opposite strands with a 9-bp overhang, and the end sequences join with the target site ends to insert the transposon at the new position; the overhangs are filled to create a 9-bp repeated target region on either side of the insertion.

Since the advent of modern molecular genetics, insertion sequences (IS) and transposons (Tn, a complex form of IS) have been used extensively as a research tool, primarily to create gene knock-outs. In recent times these knock-out systems have become sophisticated (e.g. Wetmore et al. (2015). mBio 6: e00306-e00315) and their uses have become more varied (e.g. Reznikoff (2006). Biochem. Soc. Trans. 34: 320-323). Transposons and their components, such as transposases (Tpn) and transposon DNA end-sequences (ES) have even been used in the rapidly advancing field of next-generation sequencing (NGS), and the use of transposase to make NGS libraries is now a well-established technique. The process typically uses a transposase of the type that operates by a "cut-and-paste mechanism" (FIG. 1), such as Tn5-transposase (Tn5-Tpn), as described and reviewed by Reznikoff (2008) (Ann. Rev. Genet. 42: 269-286; the contents of which are incorporate by reference herein in their entirety).

Transposition by "cut and paste" involves the transposase proteins binding to the end-sequences that bracket the transposon or IS, and then forming a dimeric complex, with the intervening IS DNA looped out. This complex is then excised from the donor site, to form a free transposome (Tsome), which carries the loop of IS DNA. The transposome then invades a DNA target site, which is cut, and the IS loop is inserted. In the process a short region of repeated target DNA can be created at the insertion site, if the cut was with overhanging ends; in the case of Tn5, 9-bp overhangs are made, and 9-bp repeats of the insertion site bracket the transposon.

This mechanism can be adapted to make NGS libraries as follows: Initially, the purified transposase is loaded with DNA "arms", which are essentially truncated versions of the transposon end-sequences. The final active complex is a dimeric transposome, comprising two transposases and two DNA end-sequences, the DNA end-sequences (i.e. DNA "arms" each with a metal ion co-factor (e.g. $Mg^{2+}$) in each of the two active sites.

Figure 2:
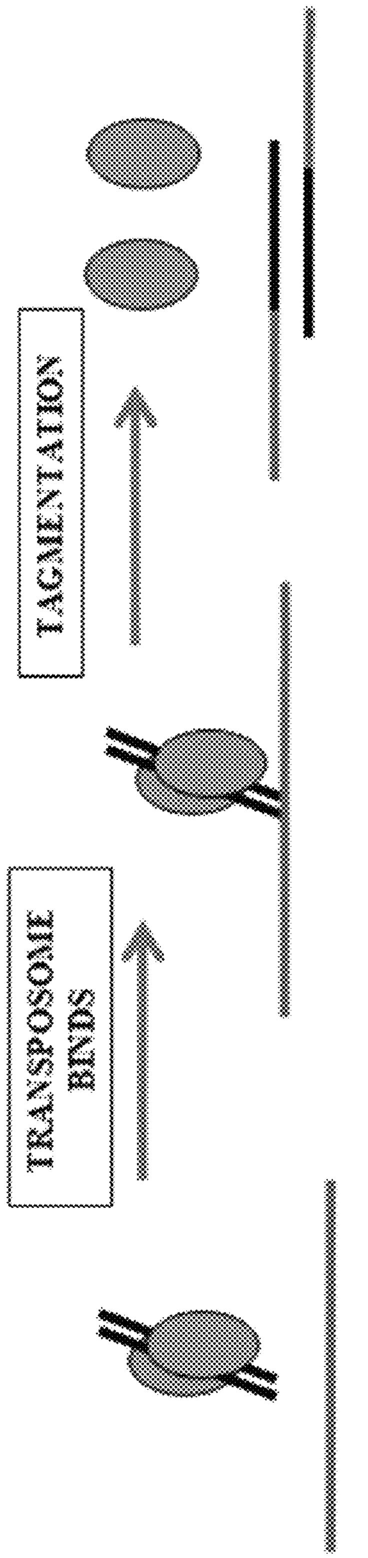
FIG. 2 is a schematic diagram depicting a process of tagmentation. The transposome inserts the two DNA "arms" into the DNA target, shearing it while tagging it at the same time.

When the transposome is put in contact with target DNA, the two interact as for a normal transposition event. In this case, however, the arms are not joined by a loop, so the effect is to cut the target DNA; this cut will be bracketed by the arms, each of which have been fused to one of the edges of the cut site (FIG. 2). The target DNA is thus fragmented and tagged (hence the term "tagmented") at the sheared-ends, subsequently this DNA is made into an NGS library.

Figure 3A:
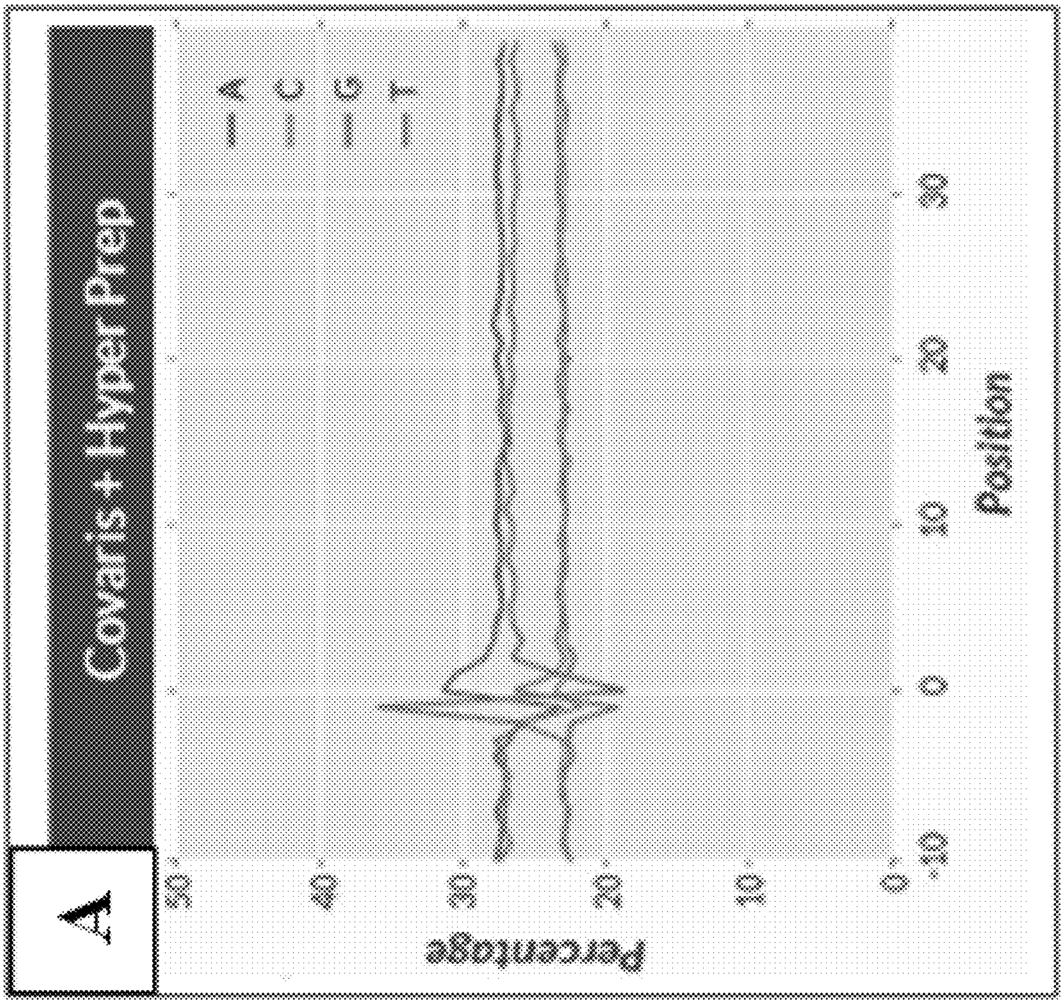
FIG. 3A-B is a pair of graphs demonstrating a sequence bias of Next Generation Sequencing (NGS) library ends, depending upon the method of creation. The percentage of each base (A, G, C or T) is plotted against the position of that base relative to the end position of the library fragment. "0" signifies the position at which shearing, or insertion, occurred. (A) Library made by mechanical shearing and end-repair (B) Library made by Tn5 tagmentation.
Figure 3B:
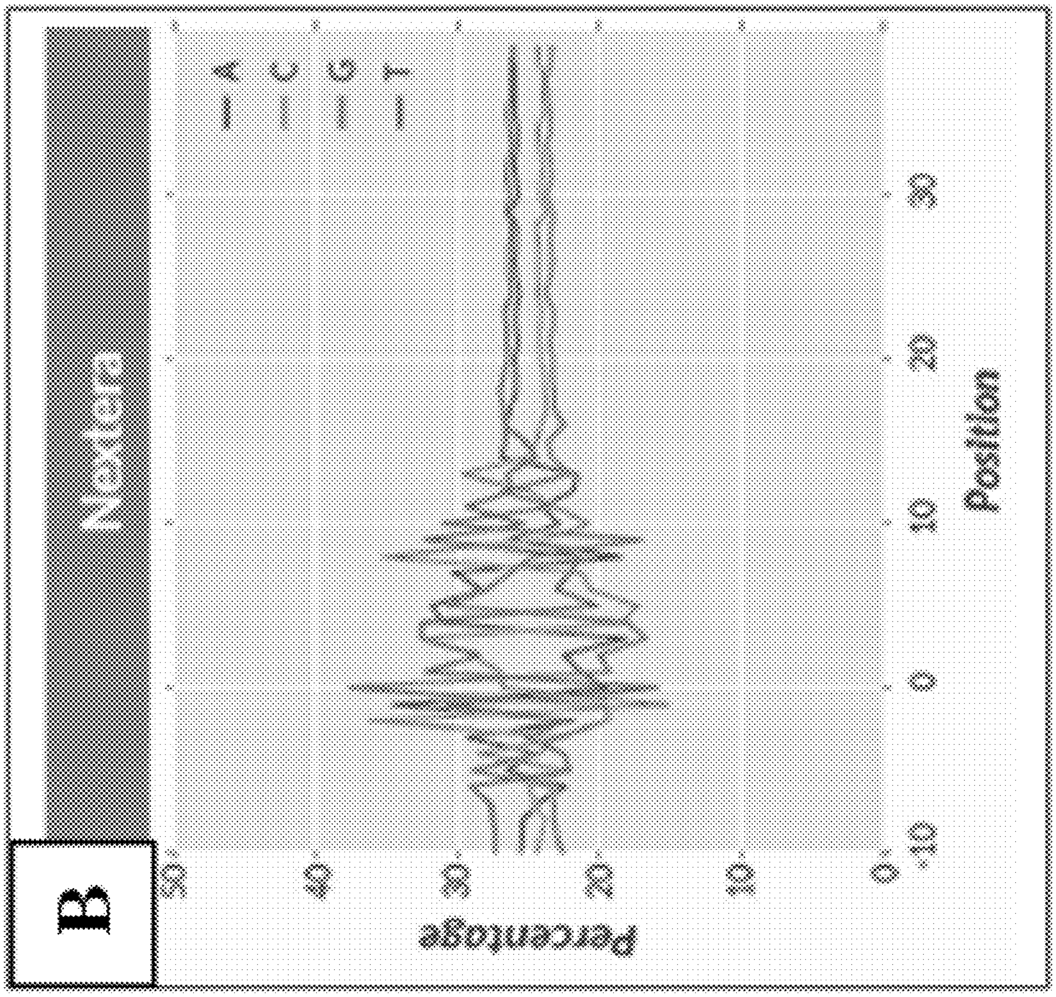

The method described above can be used instead of, and is simpler than, more traditional library making methods, which involve mechanical shearing of the DNA, followed by repair and addition of tags to the fragment ends. The main disadvantage of tagmentation is that the shearing by transposomes is biased to occur preferentially at certain sequences (FIG. 3). This bias results in an uneven spread of sequencing data when the transposase library making system is used. In contrast, the mechanical shearing methods have little bias, and shearing occurs randomly across the target.

Even the parent transposon, operating in its natural manner, displays bias in the sequence of the targets into which it inserts. The natural transposon transposition and the artificial transposome tagmentation show similar bias, as they utilize the same transposase protein and DNA end-sequences. The preference is, at least at some level, dependent upon closely local primary sequence at the target (possibly within the transposase binding footprint).

Figure 4A:
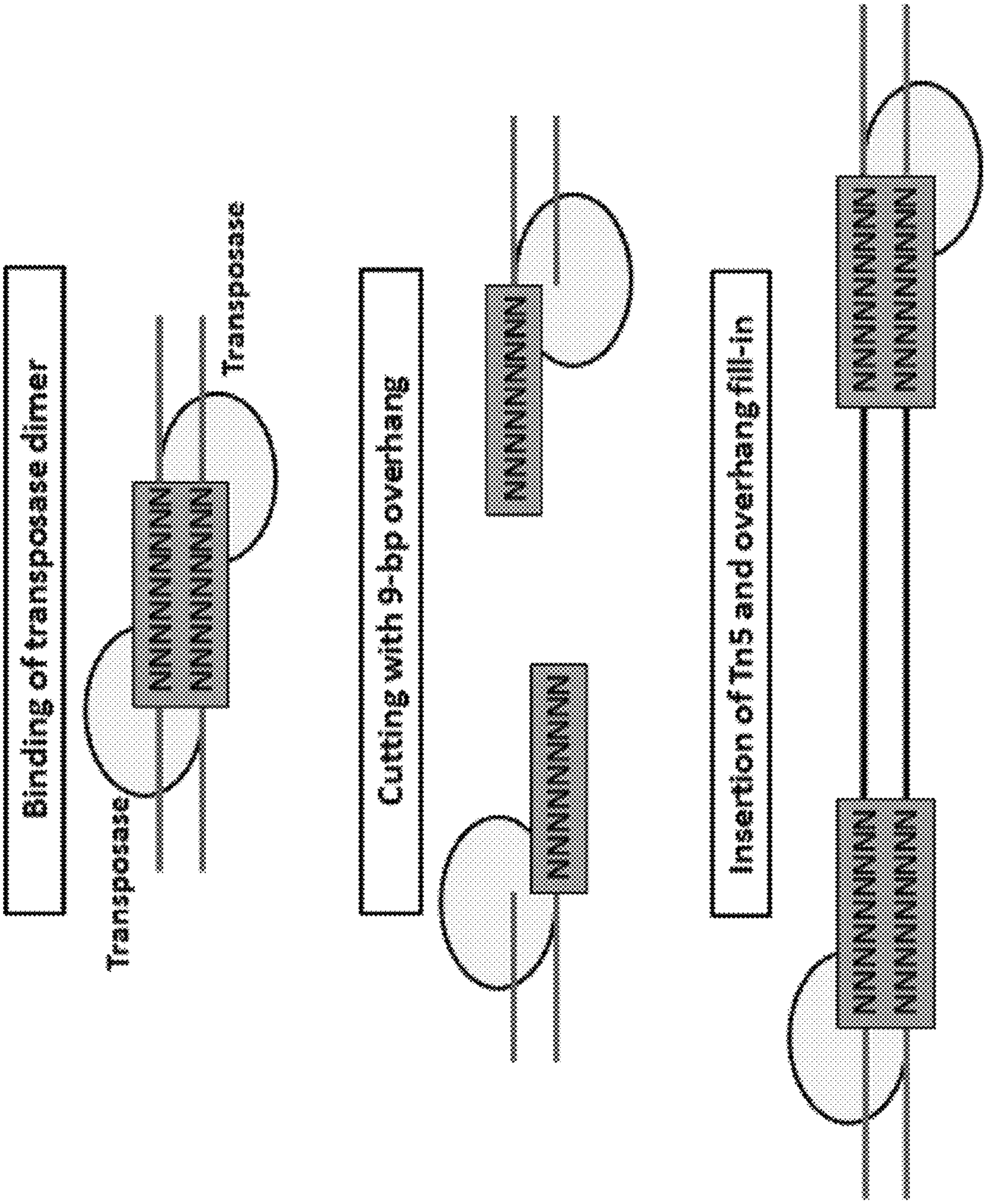
FIG. 4A-B is a pair of schematic diagrams depicting Tn5 insertion and the consensus sequence of Tn5 insertion sites. (A) The two transposase molecules of the dimer each invade at different positions (positions +1 and +9) on opposite strands of the target. Offset-cutting and fill-in ultimately creates a repeat of the target (in yellow) at either end of the transposon once it has inserted. (B) As a consequence, the consensus sequence of the Tn5 insertion sites is palindromic (from two overlapping inverted transposase preferences), with the repeat region at the center. The consensus insertion site for Tn5 is shown.
Figure 4B:
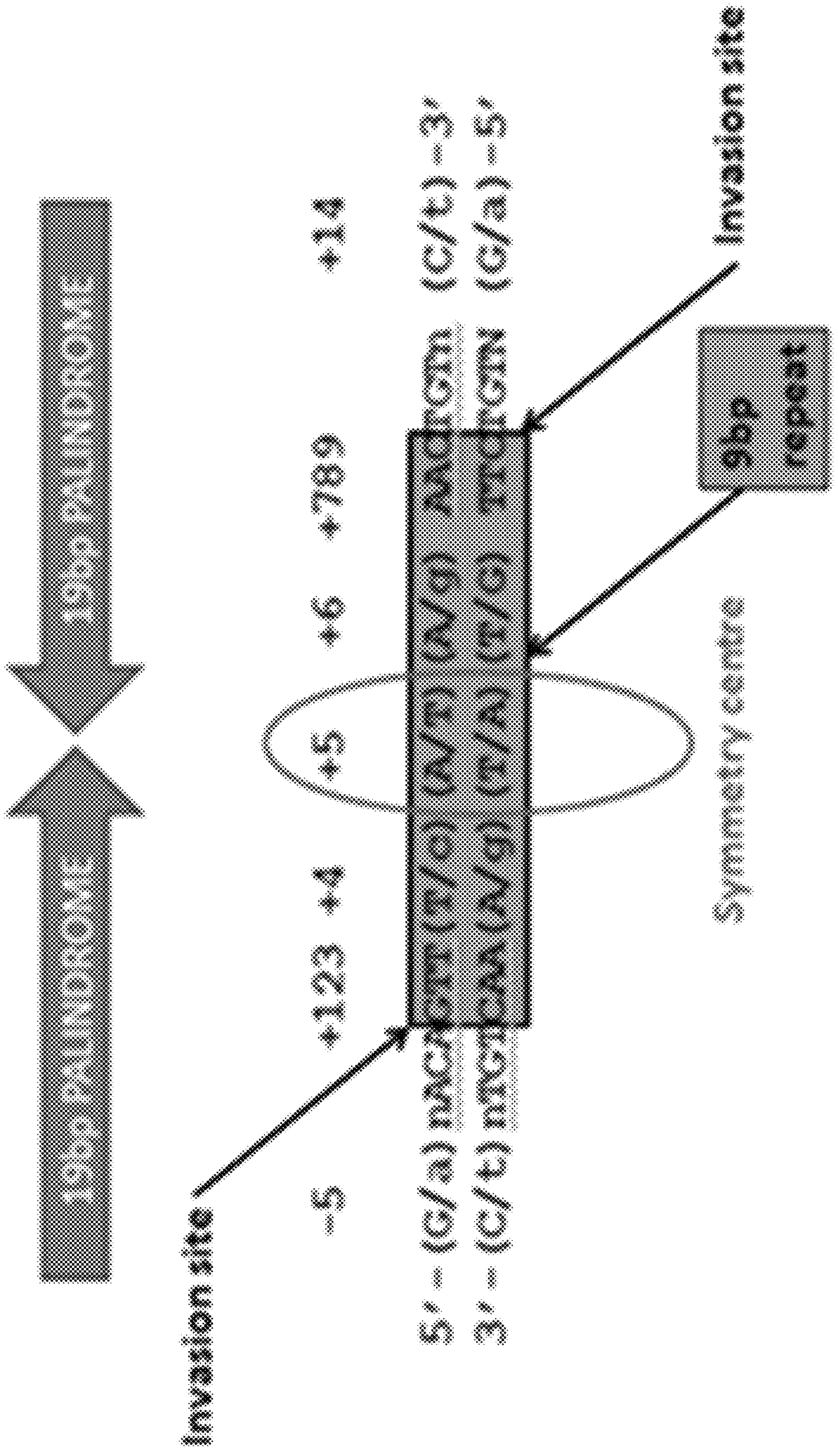

Because the transposome is a dimeric structure, a consensus sequence of the insertion site is usually palindromic to some degree. Because the cut-site and insertion position of each DNA arm is offset within the insertion site, the heart of the palindrome contains a sequence that is repeated at each of the cut ends (FIGS. 4A and B).

Mutant Tn5 Transposases

A summary of known mutations and functional positions of the Tn5 transposase can be found at: uniprot.org/uniprot/Q46731.

Of these known mutations and functional positions of the Tn5 transposase, perhaps the most important, in the sense that they are most often utilized when Tn5-transposase is used as a molecular tool, include, but are not limited to E54K, M56A and L372P. In combination, E54K, M56A and L372P can result in a "hyperactive"-Tn5-transposases, (see, for example, U.S. Pat. No. 7,083,980; the contents of which are herein incorporated by reference in their entirety). Each of the mutations are fundamentally different in the advantages that they confer to the transposase as a molecular tool, however, E54K, M56A and L372P operate on the same principle. E54K, M56A and L372P counter self-regulation and relieve intrinsic inhibition of the transposase activity. Inhibition of transposase activity is normally a crucial requirement for transposon fitness in its natural setting in order to prevent lethal levels of transposition. But inhibition of transposase activity is disadvantageous if the transposase is to be used as a molecular tool.

E54K was used in the original "standard" as well as in subsequent hyperactive mutants. E54K improves recognition of the transposon end-sequences by the transposase.

M56A does not affect the activity of the transposase sub-unit, but rather, the loss of the methionine residue prevents the production of an N-terminal-truncated version of the transposase from an internal translation start site during expression. In a natural expression system, N-terminal-truncated version of the transposase the binds to full length versions of the transposase, to form inactive heterodimers.

L372P facilitates more efficient dimerization and end-sequence binding by reducing the interaction of the C- and N-termini (an interaction that suppresses dimerization and end-sequence binding).

The disclosure uses a "hyperactive" version of the Tn5-transposase (the "Tn5-Tpn[Hyper]") that contains E54K, M56A and L372P.

Transposon Aa

The disclosure provides other transposases, including, but not limited to, a transposase related to the Tn5-transposase, designated herein "TnAa-transposase, or TnAa-Tpn". TnAa-Tpn is derived from *Alishewanella aestuarii* and may be used, for example, for making a NGS library. The TnAa-Tpn transposase has 42% identity to wild type Tn5-transposase at the amino acid level.

The disclosure provides mutant TnAa-transposases that carry either a single mutation or a double mutation. The single mutation or a double mutation of the mutant TnAa-transposases of the disclosure may correspond, functionally, to the E54K and M56A hyperactive mutations of the Tn5-transposase (numbering of the E54K and M56A hyperactive mutations of the Tn5-transposase according to SEQ ID NO: 1). These mutations are, respectively, the TnAa-transposase P47K and M50A mutations (numbering of the P47K and M50A TnAa-transposase mutations according to any one of SEQ ID NOs: 2-5). A mutation that functionally corresponds to the L372P mutation of the Tn5-transposase cannot be created in the TnAa-transposase, as the TnAa-transposase does not contain a corresponding domain to the one where this mutation is found in the Tn5-transposase.

The single mutant TnAa-transposase comprising P47K ("TnAa-Tpn[P47K]") has been used for making and NGS library, but it displays some distinct characteristics compared to those of the Tn5-transposase. Most noticeably, for both the mutant and the wild-type TnAa-transposase, the insertion site bias is not only distinct, but it is difficult to determine a clear consensus.

When a consensus sequence was derived for TnAa-transposase driven insertion, the consensus sequence was sharply defined for the first few bases (from −8 to +2, FIG. 5), but the sequence loses definition thereafter. Furthermore, there is no apparent palindrome in the consensus sequence.

The poor definition and the lack of a clear palindrome in the consensus sequence may be because the TnAa-transposase has a less ridged target binding requirement than that of Tn5-transposase. Whereas Tn5-transposase appears to invariantly attack the target with a 9-base staggered cleavage to create a 9-base repeat upon insertion, data indicate the TnAa-transposase may not be limited to a 9-base offset in its cleavage.

In FIG. 6, the four natural insertion sites of TnAa in the fully sequenced genome of *Alishewanella jeotgali* are shown (accession numbers AHTH01000009, AHTH01000020, AHTH01000026 and AHTH01000041). Of the four natural insertion sites, only one insertion site creates a perfect Tn5-like 9-base direct repeat. The other three insertion sites are either of a different length or imperfect. Such variation, if repeated on a large scale, would result in a consensus sequence that is imprecise beyond the insertion point (at which the consensus-analysis is anchored).

Barcode-Assisted Transposase Screening (BATS).

A novel high-throughput parallel method of Barcode-Assisted Transposase Screening (BATS) may be performed as described in herein, and in some embodiments, as described in Examples 8 and 12. The hyperactive Tn5 (SEQ ID NO: 1) may be used as the reference transposase. Several constructs with mutations in addition to those in hyperactive Tn5 may be generated. Amplicons comprising a mutant transposase region and a barcoded mobilisable region may be constructed, circularized and used to transform *E. coli*. Active transposases may catalyze the "jumping" of the mobilisable region into the *E. coli* genome resulting in Kanamycin resistant colonies. Genomic DNA may be isolated and, in some exemplary embodiments, an Illumina sequencing-ready library may be prepared of genomic DNA containing the UID (barcode) and the genomic insertion site (jump-site). Prior to transforming *E. coli*, the library may be sequenced using PacBio or other long-read sequencing technology to establish linkage between barcodes and their associated transposase sequence. The barcodes present in the library prior to transforming *E. coli* may also sequenced separately using, for example, by Illumina sequencing.

Effective Mapping of Genotypes to Barcodes

The overall information flow in one demonstration of analysis of a BATS experiment works in three steps:

1. Process Genotype-Barcode data, G, from a long-read PacBio sequencing run, to simultaneously extract the barcodes and the genotypes from within a construct containing known sequences. This process was termed genotype segmentation. We used regular expressions in python to recognise the known sequences, and thus isolating the variable genotypes and barcodes. The process was an iterative optimisation, in which the number of overlapping barcodes between G and J (from jump-site segmentation, see below) was optimised by varying the allowed numbers of mismatches, insertions or deletions in the regular expressions for genotype segmentation.

2. Process Jump-site data, J, from a short-reads Illumina sequencing run, to simultaneously extract the barcodes and the jumps-sites (insertion sites), from within a construct containing known sequences. This was also an iterative segmentation process. In this case, we used the overlap with a third dataset, B, which consisted only of barcodes segmented from within a construct of known sequences. The dataset B was generated by sequencing excised barcodes from the library prior to transforming *E. coli*. The *E. coli* DNA inserts obtained from R2 varied in length from one base pair to 60 base pairs. For motif analysis, only DNA inserts of at least 20 base pairs could be used, while for the coverage sub-sampling by locus approach (CSSL), shorter DNA inserts could be used, an in addition, the full length R1 could also be used in the latter method (later discussed).

3. Processing of genotype data. A caveat is that long-read sequencing, such as on PacBio, is highly error-prone. We used a specialised polishing step to get rid of the abundance of insertions and deletions characteristic of long-read sequencing. For this, we used pairwise alignment of the transposase sequences with the expected Tn5 sequence, using the program clustal. Subsequently. All insertions were deleted, which are typically polynucleotide repeats, while all deletions were filled in as 'N'. The length of barcodes were controlled to be 20 base pairs.

4. Intersecting Genotype-Barcode and Jump datasets via barcodes. A caveat exists in that sequencing error in barcodes could render a barcode unrecognisable in one or more datasets. Even though an edit distance or Leuvenstein distance approach slightly improved the overlap of barcodes, the exact overlap of barcodes was sufficient for mapping between datasets G and J, whereas distance-based methods were computationally non-feasible given the large number of reads. The barcode-genotype association was captured in a barcode-genotype counts matrix, BG. The genotypes were defined as joint codon genotypes, a general term used to represent a genotype which may have any number of mutations compared to the background genotype, even though only a single mutation was targeted in the dataset described. Rows in BG represent barcodes, while columns represent genotypes. For defining a motif of a genotype, each non-zero entry in a columns in BG (representing a genotype) were used to extract the relevant barcode (row identifier). For each barcode, all reads in the jump data J carrying those barcodes were harvested, an aligned DNA sequence pile-up created (20 base-pairs), and a motif generated. For the coverage sub-sampling approach, the data in an aligned bam file generated from the DNA inserts of the segmented R2 jump-data with barcoded read identifiers was traverse instead. Barcodes were then followed in the matrix BG to obtain the genotypes.

5. A caveat exists in that a single barcode might map to multiple genotypes, due to low complexity in the original barcode diversity. The matrix BG was conveniently used to extract only barcodes mapping to a single genotype (pure barcodes). The same intersecting step (step 4) could then easily be done on pure barcodes only.

Analysis of Inter-Motif Distances

Methods of Barcode-Assisted Transposase Screening (BATS) of the disclosure simultaneously produce rich information regarding both the mutant genotype and its preferred insertion motif. However, several aspects limit the traditional motif-based methodology applied to the analysis of cutting bias. For each of these limitations, innovations in analytics have been developed as part of these methods, and are described herein.

A Low Number of Jumps Per Genotype Requires Statistical Interpretation of Inter-Motif Distances In studies involving the evolution and selection of mutant enzymes that cut DNA or RNA, the emphasis is typically on the analysis of the combined sequence motif at the 5'-end of DNA cut sites. Analysis of such sites as motifs in the form of positional weight matrices or positional frequency matrices uses this 5'-bias as a proxy for genomic coverage bias. These matrices can in turn be visualized as bias plots in a manner similar to that described by Kia et al. (Kia et al. 2017. BMC Biotechnology. 17:6). The first limitation is that, due to the massively parallel nature of BATS experiments, a high mutant library diversity might limit the number of DNA insertion sites (jump sites) obtained per mutant. The result is that the typical analysis of insertion sites as 5'bias motifs becomes too difficult for the human eye to distinguish as a result of too few jumps into the genome, i.e. too few sampling events. A different approach is to use motif entropy, which incorporates the number of reads. However, a different approach is proposed here for BATS experiments, which is to use a network distance approach between motifs, with an appropriate statistical interpretation, as described below.

The distances between motifs of two transposases in our study were calculated from the positional-frequency matrices of the sequence reads of jumps of transposase mutants into the genome. First, the absolute difference in fractions of reads with a "C" at position 1 between a reference and test transposase is calculated (FIG. 17). This calculation is repeated for positions 2-20 and the absolute differences across all 20 positions in the read are summed. Similar calculations are performed for nucleotides "T", "A" and "G". The absolute differences for all four nucleotides at all 20 position are summed and divided by 20 to give the average difference per position. This difference is called the distance or inter-motif distance. Herein, the terms distance score and inter-motif distance may be used interchangeably.

Inter-motif distances cannot be interpreted directly, since they are dependent on the number of sequences in each of the two motifs in the comparison. We developed a bootstrapping method, coupled with interpolation of simulated datasets to provide a smoothed lookup for a p-value, given a calculated distance, and the numbers of reads in each of the two motifs (described below). The bootstrapping results are shown in FIG. 18, which demonstrates the effect that the number of sequences in both motifs have on distance.

This cumulative distribution function used to look up p-values was obtained from the probability density function, which was generated empirically by random background sampling. For the experiment, the background genome was sampled randomly as k-mers (20 base-pairs in this application), each time compiling a two pileups, with a and b sequences, and the process repeated many times, saving the distances each time, along with a and b. Subsequently, the distances were binned into bins d, converting the data into a table with value a, b and d and c, where d is the distance bin and c the number of times that a distance in bin d has been observed. Thereafter, the counts were converted to probabilities p, and subsequently, to cumulative probabilities. For example, distance score values larger than 0.95 may be interpreted as significant.

The major caveat in the approach was to convert the simulated data into a densely sampled dataset, with a convenient lookup functionality, which can also take any given distance measurement. Due to the large dynamic range of distances obtained, sampling was increasingly dense towards lower sequence counts a and b. Sampling sufficiently dense to allow approximate p-value lookup was computationally intractable, however. We instead interpolated over the distance-probability domain at a given a an b, using the interpolate package in the python scipy library to generate more data points in between true sampling values. This provided us with the required sampling density required to accurately obtain the relevant p-values. Next, interpolation was again used to fit the simulated data with a, b and d as inputs, allowing easy access to p-values p, which is fast enough to allow all-against-all comparison statistics involving thousands of motifs.

Another way of illustrating jump site bias is by plotting sequence logos. In order to determine jump site nucleotide sequence bias for each transposase variant sequence logos were generated using the website "WebLogo3" (http://weblogo.threeplusone.com/; Crooks et al. (2004) Genome Research, 14:1188-1190; Schneider et al. (1990), Nucleic Acids Research. 18:6097-6100). Multiple 60 base-pair sequences containing the respective jump sites for each variant were aligned for this purpose. The sequence logos are show in FIG. 20. The overall height of the nucleotide letter containing stack indicates the sequence conservation at that position, while the height of nucleotide letters within the stack indicates the relative frequency of the respective nucleotides at that position. This analysis highlights the importance of certain nucleotide positions and—compositions important for transposase variant-DNA interaction. However the examination of sufficient jump sequences are required in order separate significant nucleotide positions from those contributing to background noise. This is clearly illustrated by the low overall background signal observed in the motif generated from 86 sequences for variant E146C as opposed to absence of this background signal in all the other variants constructed from more (in excess of 177) sequences (see Table F).

Coverage Sub-Sampling by Loci as an Alternative to Inter-Motif Distance Analysis of Data from BATS Experiments Another limitation is that 5'-motifs might not sufficiently capture the essence of coverage bias, as in the scenario of library preparation in the form of tagmentation of purified DNA. An important goal in library preparation protocols is to obtain both even and complete coverage of the genome or transcriptome targeted, and 5'-bias could be seen as merely partly correlated with genomic coverage, or even merely a cosmetic feature. Also, the representation of a motif as a single positional weight matrix, or as a single positional frequency matrix, essentially captures an averaged binding strength-related profile, and does not fully make use of joint likelihoods of neighbouring bases at potentially variable distance(s). Using more complex models such as Markov models or neural networks would essentially require more reads, scaling strongly with the order of the model, making them less useful for detecting differences in limited data. It would be ideal to be able to interpret results directly in terms of coverage over the genome. The fact that coverage over the genome is not sufficient in a highly multiplexed experiment like BATS where thousands of mutants can potentially be screened in parallel, effectively excludes the direct targeting of coverage from low sequence read numbers, resulting in the use of the proxy of motif analysis. However, this disclosure shows that the comparative genomic coverage is indeed accessible by using the genomic loci of jumps from a BATS experiment.

Coverage Sub-Sampling by Loci (CSSL) works by first mapping the sequenced genomic DNA insert of the transposase jump site to the appropriate reference genome, and relate the genomic locus to the expected coverage of a reference dataset R that has a sufficient coverage to serve as a reference coverage distribution. The sample datasets of interest, S, are effectively sampled from the distribution R by using the same genomic coordinates. Effectively, the genomic locus makes the rational link for mapping data from reference genotype R to the sample genotype S of interest. The reference genotype R could for instance be the wild-type form of the Tn5 transposase applied in tagmentation in a normal library preparation experiment, or a library preparation using tagmentation with an enzyme available in the market, whereas the sample genotype S might refer to the mutant genotypes originating from site-directed mutagenesis or random mutagenesis in a BATS or related experiment. For each of the sample genotypes, a sample distribution S is sampled from the reference distribution R via the genomic loci, and subsequently the two distributions R and S are compared using statistical tests such as 1) the Mann-Whitney Test for differences in means, 2) the Kolmogorov-Smirnoff Test for different distribution shapes, 3) other parametric or non-parametric tests, 4) visual inspection of shape differences, 5) percentile-based metrics such as the percentage of loci sampled at less than 25% of the mean coverage in the parent distribution, or any other method to detect differences in shape. In this manner, mutants may be selected which can access those loci better than the reference R or background B transposases can access.

An additional flexibility in the method is that samples, S, may be compared to one another. For instance, mutant sample S1 could be compared to wild-type or background genotype B from which S1 was originally mutated, for which the distribution is also obtained by CSSL using reference R.

As an example, CSSL analysis was performed on data from the same BATS experiment as in example 12 and the results are indicated in FIGS. 21 and 22. In this experiment, reference genotype B is transposase hyperactive Tn5 resulting in the reference data set B. The sample data sets, S, are derived from Tn5 mutants that each have a mutation in addition to those in hyperactive Tn5. Statistical tests are done on the comparison of S with B and the resulting p-values for both the Mann-Whitney and Kolmogorov-Smirnoff tests are indicated in Table F. The data in FIG. 21 shows the data for two mutants, W125G and G251A, and the reference hyperactive Tn5. The mobilisable element associated with two transposase mutants inserted into loci in the genome that tend to show lower coverage with the reference data set B, generated with hyperactive Tn5. Improved coverage in regions with low coverage of the reference transposase R, or background transposase B, would be beneficial, for example in variant calling, as described below. The data in FIGS. 21 and 22 were smoothed solely for visualization purposes by calculating and plotting the mean of 3 three data points.

In a similar way, the results of CSSL analysis of data for mutations E146A, E146C, E146N and E146S are depicted in FIG. 22. It is evident from FIG. 22 that particular mutations at position E146 in Tn5 result in preferential insertions into the genome at loci in the genome that are well covered by the reference transposase. As such, these mutations at position E146 have an increase in bias. This further illustrates the utility of this method in determining differences in bias between mutants and how this relates to transposase mutants' preference for insertion into low vs high coverage regions of the genome.

Low-coverage regions are typically the cause of false variant calls such as SNPs and indels, due to a lack of evidence for the variant caller. Conversely, incorrect-alignment of reads with multiple positions with equal mapping quality due to repeats in the genome could also result in false variant calls due to the introduction of alignment-borne errors, correlating with regions of excessive coverage in such regions. In such a scenario, coverage sub-sampling lends itself to the selection of mutants with a lack of coverage in the high-coverage region. The sub-sampling might for instance also be limited to the most relevant regions, such as the regions of interest, including biologically encoding regions, lists of target loci for variant calling, or any other locus-specific criterion.

Hence, even with the lower read numbers obtained during massively parallel BATS experiments with high numbers of genotypes, genomic coverage could be accessed without requirement for motif analysis. In another form of CSSL, the distributions R, S and B could be converted to a chosen descriptive feature, such a GC content, higher dimensional k-mer frequency, or known DNA modification pattern as a function of the locus. It is common practice to compare library preparation technologies in terms of their GC-bias on genomic level. CSSL provides an effective method to select for GC-unbiased enzymes during BATS experiments.

The data from the above BATS experiment was analysed with the aim of establishing whether Tn5 transposase mutants display an altered GC-bias. The jump sites (insertion site) for a reference transposase (Hyperactive Tn5) and mutants were mapped to the reference genome and the GC content of a 100 bp window was calculated. FIGS. 23 and 24 are plots of the probabilities of insertion of a given transposase as a function of the GC-content of the target DNA. FIG. 23 shows the jump site data for two mutants and the reference Hyperactive Tn5. The two mutants, P214S (SEQ ID NO: 23) and G251A (SEQ ID NO: 24), have a significantly increased preference for lower GC-content than the reference transposase (see Table G for p-values). That the Tn5 mutant G251A has an increased insertion preference for low GC-loci could potentially be the mechanism by which the same mutant has an increased probability for insertion at loci that are low-coverage loci as indicated in FIG. 21.

FIG. 24 shows the jump-site data from three Tn5 mutants. These three mutants, E146N, E146A and E145S, have higher probability of insertion into high-GC loci compared to that of the reference transposase. Mann-Whitney and Kolmogorov tests for differences in the mean and curve-shape, respectively, were performed and the p-values are indicated in Table G.

Definitions

As used throughout the disclosure, the singular forms "a," "and," and "the" include plural referents unless the context clearly dictates otherwise. Thus, for example, reference to "a method" includes a plurality of such methods and reference to "a transposase" includes reference to one or more transposases and equivalents thereof known to those skilled in the art, and so forth.

The disclosure provides isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the disclosure or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments, variants, mutants (mutations) of the disclosed DNA sequences and proteins encoded by these DNA sequences. As used throughout the disclosure, the term "fragment" refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the disclosure.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

"Binding" refers to a specific, non-covalent interaction between macromolecules (e.g., between a protein and a nucleic acid, or between two proteins). Such specific binding is usually based on specific interactions between specific structural motifs that usually but not always, reflect those that occur in a natural biological setting.

"Sequence-specific binding" refers to a sequence specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. The term "sequence-specific binding" is not limited to strong, narrow sequence preferences but also includes the weak preferences displayed by molecules that can bind at a large variety of polynucleotide targets but with a preference for some over others. Such binding might also be termed "semi-random sequence-binding" or "biased sequence-binding".

The term "preferentially bind" refers to a hierarchical order of binding of a transposase or transposome (active or inactive) to a sequence within a target DNA (e.g. genomic DNA). A transposase or transposome (active or inactive) of the disclosure will preferentially bind to a certain site, and so these preferred sequences are more readily occupied than alternative sequences. As these preferred sequences become occupied the transposase or transposome (active or inactive) has more freedom to bind to an alternative, and less preferred sequence. At a saturating concentration, the transposase or transposome (active or inactive) will bind all available sequences; however, the preferred sites will tend to be occupied first. Thus, at low concentrations of the transposase or transposome (active or inactive) of the disclosure, the sequences first occupied are "preferentially bound".

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this disclosure.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

A "binding site" or "binding sequence" is a target nucleic acid sequence that defines a portion of a nucleic acid to which a transposase, DNA adaptor, and/or transposome will bind, provided sufficient conditions for binding exist.

A "consensus sequence" is a target nucleic acid sequence that defines a portion of a nucleic acid to which a transposase, DNA adaptor, and/or transposome will bind, provided sufficient conditions for binding exist, that is present in more than one variation of a binding sequence or binding site. Although a transposase, DNA adaptor, and/or transposome of the disclosure may prefer to bind to a first sequence, should all sites comprising that sequence be occupied the transposase, DNA adaptor, and/or transposome of the disclosure may bind to a second sequence, the first and second sequence comprising a consensus sequence. For example, upon alignment of the first and the second sequences, although one or more bases may vary, the remaining bases that are invariant may comprise the consensus sequence.

The terms "target" and "input" DNA may be used interchangeably throughout the disclosure.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Nucleic acids of the disclosure may be single-stranded or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence that are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "perfect complementarity" refers to a first and a second sequence that hybridize to one another without a gap or a mismatch of bases along the length of the nucleic acid duplex. For example, a first and a second sequence may hybridize to one another with perfect complementarity according to Watson-Crick base-pairing rules.

As used throughout the disclosure, the term "imperfect complementarity" refers to a first and a second sequence that hybridize to one another without one or more gaps or one or more mismatches of one or more bases along the length of the nucleic acid duplex. For example, a first and a second sequence may hybridize to one another with 70%, 75%, 80%, 85%, 90%, 95%, 99%, or any percentage in between of bases hybridized to one another along the length of the nucleic acid duplex.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some embodiments, fusion polypeptides and/or nucleic acids encoding such fusion polypeptides include conservative substitutions have been introduced by modification of polynucleotides encoding polypeptides of the disclosure. Amino acids can be classified according to physical properties and contribution to secondary and tertiary protein structure. A conservative substitution is a substitution of one amino acid for another amino acid that has similar properties. Exemplary conservative substitutions are set out in Table A.

Table A

Conservative Substitutions I

| Side chain characteristics | | Amino Acid |
|---|---|---|
| Aliphatic | Non-polar | G A P I L V F |
| | Polar-uncharged | C S T M N Q |
| | Polar-charged | D E K R |
| Aromatic | | H F W Y |
| Other | | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

Table B

Conservative Substitutions II

| Side Chain Characteristic | | Amino Acid |
|---|---|---|
| Non-polar (hydrophobic) | Aliphatic: | A L I V P |
| | Aromatic: | F W Y |
| | Sulfur-containing: | M |
| | Borderline: | G Y |
| Uncharged-polar | Hydroxyl: | S T Y |
| | Amides: | N Q |
| | Sulfhydryl: | C |
| | Borderline: | G Y |
| Positively Charged (Basic): | | K R H |
| Negatively Charged (Acidic): | | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

All percentages and ratios are calculated by weight unless otherwise indicated.

All percentages and ratios are calculated based on the total composition unless otherwise indicated.

Every maximum numerical limitation given throughout this disclosure includes every lower numerical limitation, as if such lower numerical limitations were expressly written herein. Every minimum numerical limitation given throughout this disclosure will include every higher numerical limitation, as if such higher numerical limitations were expressly written herein. Every numerical range given throughout this disclosure will include every narrower numerical range that falls within such broader numerical range, as if such narrower numerical ranges were all expressly written herein.

The values disclosed herein are not to be understood as being strictly limited to the exact numerical values recited. Instead, unless otherwise specified, each such value is intended to mean both the recited value and a functionally equivalent range surrounding that value. For example, a value disclosed as "20 μm" is intended to mean "about 20 μm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosure have been illustrated and described, various other changes and modifications can be made without departing from the spirit and scope of the disclosure. The scope of the appended claims includes all such changes and modifications that are within the scope of this disclosure.

EXAMPLES

In order that the invention disclosed herein may be more efficiently understood, examples are provided below. It should be understood that these examples are for illustrative purposes only and are not to be construed as limiting the invention in any manner. Throughout these examples, standard recombinant DNA, or other molecular biology techniques were carried out according to methods described by either: (1) Green and Sambrook, Molecular Cloning: A Laboratory Manual, 4th ed., Cold Spring Harbor Press (2012). (2) The suppliers of commercial kits and reagents. (3) Web-based protocol collections, such as Protocol-On-Line (protocol-online.org/), except if otherwise noted. Throughout these examples, protein expression, purification, assay and visualization and other standard protein production techniques, were carried out according to methods recommended by the suppliers of commercial kits and reagents, except where otherwise noted.

Example 1: Design and Construction of Transposition-Test-Amplicons

The basic components required in the final construct to be used in the ultimate parallel barcode transposition and screening experiment(s) are shown in parts 1 and 2 of FIG. 8. However, in order to test and develop the basic methodology, the initial DNA constructs do not need to carry either the mutant transposase or barcodes. Instead, preliminary experiments were conducted with wild-type or a limited number of hyperactive transposases, each on an individual basis, so UIDs are unnecessary. These simple initial versions of the recombinant DNA constructs are referred to as "minimal test vectors". For further simplification, the constructs do not need to be cloned and purified; the preliminary tests were conducted using DNA test material that is created and maintained by PCR only.

The initial different minimal test vectors were therefore created and maintained as linear amplicons. Five different minimal test vectors were constructed, each with a different transposase. One of the constructs carried a hyperactive version of Tn5-transposase (mutations E54K M56A L372P, SEQ ID NO: 1). The other four constructs carried different versions of the TnAa-transposase. The first was the wild-type transposase (SEQ ID NO: 2); the second carried two mutations (P47K and M50A, SEQ ID NO: 3). The remaining two transposases each carried only a single mutation (M50A, Sequence ID 4 or P47K, SEQ ID NO: 5). The overall structures of the five constructs are shown in FIG. 10.

The annotated sequences of the entire minimal test vector with the hyperactive Tn5-transposase (SEQ ID NO: 6) is displayed in FIG. 25. The Tn5-Tpn [hyper] gene spans positions 168-1622 with at start codon from positions 165-167 and a stop codon from positions 1623-1625. The E54K mutation spans positions 351-353. The M56A mutation spans positions 357-359. The L372P mutation spans positions 1305-1307. A Tet-35 site spans positions 53-58. A Tet-10 site spans positions 66-71. A BglII restriction site spans positions 1-6. An XbaI restriction site spans positions 124-129. An NcoI restriction site spans positions 163-168. A BamHI restriction site spans positions 1647-1652. The barcode cloning site spanning positions 1679-1702 encompasses three restriction sites, SpeI (1679-1684), StuI (1688-1693), and AsuII (1697-1702). An LHS ES site spans 1658-1676. A ribosome binding site (RBS site spans positions 154-158. A kanamycin resistance gene spans positions 1854-2653 with a start codon at positions 1851-1853 and a stop codon at positions 2654-2656. An RBS spans positions 1841-1843. An MfeI restriction site spans 2678-2683. An AvrII restriction site spans positions 2729-2734. An RHS ES site spans positions 2686-2704. Additionally, primer sequences displayed in FIG. 25 are listed in Table D.

The annotated sequences of the entire minimal test vector with the P47K-mutant TnAa-transposase (SEQ ID NO: 7) is displayed in FIG. 26. The TnAa-Tpn [P47K] gene spans positions 168-1562 with at start codon from positions 165-

167 and a stop codon from positions 1563-1565. The P47K mutation spans positions 330-332. A Tet-35 site spans positions 53-58. A Tet-10 site spans positions 66-71. A BglII restriction site spans positions 1-6. An XbaI restriction site spans positions 124-129. An NcoI restriction site spans positions 163-168. An MluI restriction site spans positions 258-263. A BamHI restriction site spans positions 1587-1592. The barcode cloning site spanning positions 1679-1702 encompasses three restriction sites, SpeI (1619-1624), StuI (1628-1633), and AsuII (1637-1642). An LHS ES site spans 1598-1616. A ribosome binding site (RBS site spans positions 154-158. A kanamycin resistance gene spans positions 1794-2603 with a start codon at positions 1791-1793 and a stop codon at positions 2604-2606. An RBS spans positions 1781-1783. An MfeI restriction site spans 2618-2623. An AvrII restriction site spans positions 2636-2641. An RHS ES site spans positions 2626-2644. Additionally, primer sequences displayed in FIG. 26 are listed in Table D.

The component parts of the minimal test vectors were created by standard techniques, and full-length vectors were assembled by PCR. Stocks of the vectors were created by PCR using the primer pairs TPCR-2-F and TPCR-1-R (see Table D below as well as SEQ ID NO: 6 and 7, above). The sequences were checked by Sanger sequencing.

TABLE D

| Name | Oligonucleotide sequence | SEQ ID NO: |
|---|---|---|
| TPCR-2-F | 5'-AGATCTCCATCGAATGGCCAGA-3' | 8 |
| TPCR-1-R | 5'-CCTAGGACGTAACTACTCTCGTTGTCC-3' | 9 |
| TPCR-3-F | 5'-CTCGAGTAACGGACGAACGCA-3' | 10 |
| TPCR-2REEco-F | 5'-ATACCTACATGAATTCAGATC TCCATCGAATGGCCAGA-3' | 11 |
| TPCR-1REEco-R | 5'-AGGCCGTTATGAATTCCCTAGGACGT AACTACTCTCGTTGTCCAGC-3' | 12 |
| Kan-AF | 5'-TGATGCGCTGGCAGTGTTC-3' | 13 |
| IPCR-R | 5'-CTTGTGCAATGTAACATCAGAG-3' | 14 |
| IPCR-F | 5'-ATGGTATTGATAATCCTGATATG-3' | 15 |

In the initial construction effort, the minimal test vector that carried the TnAa-transposase with two mutations (P47K and M50A) also carried a single base deletion mutation. The correct vector was made later, but results from early tests (below) do not, therefore, include this construct Example 2: Initial Transformation and Transposition Tests with Linear Amplicons Five different minimal test vector amplicons were made by PCR. Amplification was with Kapa Biosystems HiFi polymerase, using the primer pair TPCR-2-F and TPCR-1-R (see Table D as well as SEQ ID NO: 6 and 7, above) and the following cycling profile: 4° C., hold/95° C., 2 min/(98° C., 30 sec/58° C., 30 sec/72° C., 2 min) X20/4° C., hold.

The PCR product was purified using a QIAgen PCR purification kit, quantified by spectrometry and stored at −20° C.

To prepare the minimal test vector amplicons for electroporation into *E. coli* DH10B, the sample was further purified using a Zymo DNA clean kit (#5). In each case a 1 μg sample was loaded and this was eventually eluted in 30 μl of ultra-pure water. Sample integrity was confirmed by separating 5 μl (approximately 170 ng) on an agarose gel, as shown in FIG. 11.

20 μl of electro-competent *E. coli* DH10B cells was added to the DNA (either 33 ng of the minimal tests vectors or 1 ng of a control pET29 plasmid), in a 1 mm-gap electroporation cuvette and pulsed at 20 Kv, 200 ohms, 25 g. Time constants varied from 5.5-5.7. After 500 μl of SOC was added, the cells were incubated at 37° C. for 50 min. Undiluted samples (100 μl) were then plated on Luria agar containing Kanamycin at 30 μg/ml. Petri dishes were incubated overnight at 37° C., after which plates were scored for colony numbers.

Only in the case of the pET29 plasmid control were any colonies observed.

Example 3: Initial Transformation and Transposition Tests with Circularized Amplicons The failure of the minimal test vectors to effectively deliver the mobilisable, selectable region to the chromosome of the *E. coli*, as described above, may be due to the fact that the amplicon is damaged upon entry to the cells. Such damage may well occur at the ends of the amplicon by exonuclease attack. Alternatively, or in addition, linear DNA may not transform *E. coli* as efficiently as circular DNA. To address these possibilities, and to more closely mimic traditional transformation involving plasmid DNA, the effect of circularizing the minimal test amplicons was tested by ligation prior to transformation.

The Tn5-transposase [Hyper] and TnAa-transposase [M50A] carrying minimal test vectors were again made by PCR. Amplification was performed using the primer pair TPCR-2-F and TPCR-1-R as before (Table D as well as SEQ ID Nos: 6 and 7) but this time with Kapa Biosystems 2G Robust Readymix and the following cycling profile: 4° C., hold/95° C., 2 min/(98° C., 30 sec/58° C., 30 sec/72° C., 2 min) X15/4° C., hold.

In addition, a shorter version of the minimal test vector, one that lacked a transposase component and comprised the mobilisable kanamycin region only (1117 bp fragment, nucleotides 1617-2734 in SEQ ID NO: 6 above) was created. This was also done by PCR amplification using 2G Robust Readymix and a full length template as above, except that the TPCR-2-F primer was replaced with the TPCR-3-F (Table D, SEQ ID NO: 6 above).

In all cases the amplicons were separated on a TBE agarose gel and purified using a QIAgen gel purification kit, and then quantified by spectrometry. 2G Robust can leave 3'-A-overhangs, so the overhanging ends were converted to blunt ends using Kapa Biosystems HiFi polymerase (0.5 U HiFi, 0.3 mM dNTPs, in 25 μl at 72° C. for 5 mins). The blunt-ended PCR product was purified using a QIAgen PCR purification kit. The integrity was checked on a TBE agarose gel (shown in FIG. 12A) and the samples quantified by densitometry. Sample concentrations were between 40-100 ng/μl.

In order to be able to circularize the amplicons by ligation, the 5'-ends need to be phosphorylated (the PCR primers were not phosphorylated). This was done using Kapa Biosystems polynucleotide kinase, using 10 μl (400-1000 ng) of amplicon DNA in a 20 μl reaction. Following this, 10 μl (200-500 ng) of the phosphorylated amplicon was self-ligated in a 20 μl reaction using Kapa Biosystems ligase in standard (not fast) ligase buffer. Ligation was at 16° C. overnight. Equivalent amounts (5 μl, 200-500 ng) of the same amplicons, but without the phosphorylation treatment were likewise ligated. A 5 μl sample (50-125 ng DNA) of the ligation was separated on an agarose gel (shown in FIG. 12B), which confirmed that some of the amplicons had circularized and some had joined to form multimeric complexes. The remaining ligation mix was further purified using a Zymo DNA clean kit (#5) and eluted in 12 μl ultrapure water, in preparation for transformation of *E. coli* DH10B.

Transformation was essentially as previously described (Example 3), except that 3 μl of the purified ligation mix was used (final concentration unknown due to possible losses during purification) and the transformed cells were incubated at 37° C. for 3 hr before 150 μl aliquots were plated, in order to maximize the period during which transposition of the mobilisable region could occur.

In the case of both the TnAa-transposase [M50A] carrying minimal test vector, and the shortened mobilisable kanamycin region-only vector, only a few colonies were seen (average 5/plate). These probably represent illegitimate recombination-driven insertion events. In contrast, transformation with the Tn5-transposase [Hyper] carrying minimal test vector resulted in colonies that were too numerous to count, indicating that transposition had occurred. It should be noted that the high number of colonies may, in part, be due to cell division that could have occurred during the extended, 3 hr, incubation prior to plating.

The failure of the TnAa-transposase [M50A] carrying minimal test vector to generate discernable numbers of transposition events is not unexpected, as the M50A-type mutation is known to act at the level of expression of active dimers in the bacteria, and expression may not be limiting in this case. Instead, it may be that the activity enhancing mutation P47K is required.

In order to test if TnAa-transposase driven transposition could be increased to detectable levels if the P47K mutant version was used, the experiment was repeated with a minimal test vector that carried that version of the transposase. In this experiment three minimal test vectors were compared; they carried the hyperactive transposase from Tn5, the wild-type transposase from TnAa, and the P47K mutant transposase from TnAa.

The experiment was essentially as before, with the following specific details: New working stocks of minimal test vector template DNA were made. The amplification was with Kapa Biosystems HiFi as before, the amplified DNA was separated on a 0.75% TBE agarose gel and the appropriate amplicon isolated using a QIAgen gel purification kit. The DNA was quantified by spectroscopy and stored at −20° C. in 10 mM Tris-Cl (pH 8.0).

Experimental samples were amplified with Kapa Biosystems HiFi polymerase using the working stocks as a template (100-200 ng) in a 25 μl reaction as before. Samples were purified using a QIAgen PCR purification kit and quantified as before. In this case blunt-ending was not required so each DNA sample was immediately phosphorylated, at a final concentration of 50 ng/μl. 10 μl (500 ng) of this was then self-ligated in a 20 μl final volume, and then purified, as before.

Transformation was as previously described above, except that transformed cells were incubated at 37° C. for 1 hr before plating. The reduced expression time is to minimize the possibility of colony numbers increasing due to cell division prior to plating. Both 100 μl of undiluted and 50 μl of 1:10 diluted samples were plated.

In the case of the wild-type TnAa-transposase carrying minimal test vector, only a few colonies were seen (average 47/plate with undiluted sample). In contrast, transformation with both the hyperactive Tn5-transposase and the P47K mutant TnAa transposase carrying minimal test vectors gave average counts from 1:10 diluted samples of 112 and 63 colonies/plate respectively. From this we calculate that in these two cases, $1.2 \times 10^4$ and $0.6 \times 10^4$ transposition events were captured in the total transformation mix.

Example 4: Methods to Improve Sample Preparation, Transformation and Transposition The insertion site screening experiment described here ideally requires that large numbers of transposition events be captured. Furthermore, each of these should be driven by a single mutant transposase that acts only in conjunction with a specific UID-tagged mobilisable region. As far as possible, cross-talk between unrelated transposases and UID-barcoded regions should be avoided. Such cross reactivity might occur if two different constructs transformed the same bacterial host at the same time. This can be considered a remote possibility, unless the two different constructs had become conjoined prior to transformation, for example by forming heterogeneous multimers during the PCR or ligation steps.

Any change in methodology that improves the numbers and efficiency of transformation of the bacteria or subsequent transposition would be a useful improvement. Likewise any improvements that reduce the chances of cross reactions will be beneficial.

Improvements made to the process are described below:

In order to reduce the chances of PCR-derived flawed constructs being included a gel purification step has been implemented immediately after initial amplification of the linear vectors, this enables selective DNA retrieval of the correct size for subsequent steps.

In order to improve the ligation efficiency at the circularization, step both of the amplification primers have been modified to include the same restriction site (for example, a restriction site that generates overhanging ends). Following amplification and gel purification, the PCR product is digested with the restriction enzyme and then purified. Thereafter, circularization is more efficient because the overhanging compatible ends promote ligation. An example of such a primer pair are the primers TPCR-2REEco-F and TPCR-1REEco-R (modified versions of TPCR-2-F and TPCR-1-R, shown in Table 1).

In order to eliminate remaining linear molecules after ligation a step has been implemented wherein the sample is digested with Exonuclease III and Exonuclease VII.

In order to reduce the chances of ligation-derived multimeric constructs being included, a gel purification step has been implemented immediately after ligation. Consequently, only circular monomeric molecules are isolated and the purified and/or enriched circular monomeric molecules used for the subsequent transformation.

One or more of these additional steps may be used in any combination to optimize a method of the disclosure.

Example 5: Initial Testing of Insertion Site Isolation and Preliminary Sequence In order to conduct a preliminary test of insertion site isolation, a limited number of clones in which transposition of the mobilisable region had occurred were pooled and the insertion sites were amplified and, in a few cases, cloned and sequenced. Two pools were tested; in one case the pool contained 5 individual clones, in the second case there were 80 clones. In both cases transposition was driven by the TnAa-Tpn [P47K], and the clones were generated as described in Examples 3 and 4.

To create the small pool, 5 colonies were tooth-picked into a single Luria broth culture (kanamycin 30 ug/ml), cultured overnight, pelleted in a centrifuge and then used for genomic DNA isolation. For the larger pool, colonies were harvested directly from the agar surface of a petri dish that carried 80 colonies. These were scraped into 1 ml of Luria broth that had been added to the petri dish, and a homogenous mixture of cells was made. The cells were pelleted by centrifugation and the DNA was isolated. In both cases genomic DNA was isolated from the *E. coli* cells using a Sigma GenElute bacterial genomic kit.

The insertion sites were then isolated, by an inversion PCR methodology that enables the sequencing of both ends of the insertion site, essentially as outlined in FIG. 9(B).

In detail: 1 μg of the genomic DNA was digested with a mixture of the 5 restriction enzymes BamHI, EcoRI, NcoI, NdeI, XhoI in the mutually compatible New England Biolabs CutSmart buffer. Digests were in an 80 μl final volume with 20 U of each enzyme and were incubated at 37° C. overnight. None of these restriction enzymes cut within the mobilisable region sequence, and will therefore only digest within the genomic DNA surrounding the insertion site. The digested DNA was purified using a Zymo DNA clean kit (#5), and then the overhanging ends were filled and blunted using Kapa Biosystems HiFi polymerase (0.5 U HiFi, 0.3 mM dNTPs, in 25 μl at 72° C. for 5 mins). The DNA was purified with a Zymo kit as before and then quantified by spectrometry. The concentrations were 10.3 ng/μl and 15.3 ng/μl for the 5- and 80-colony-pool respectively.

Following this, different volumes (0.1-5 μl) of the DNA were self-ligated in a 10 μl reaction using Kapa Biosystems ligase in standard ligase buffer. Ligation was at 16° C. overnight. The inversion PCR was then conducted using a Kapa Biosystems Long Range PCR kit, with all 10 μl of the ligation mix placed directly into a final 125 μl reaction volume (0.625 U Long Range enzyme, 1.75 mM $MgCl_2$, 0.3 mM each dNTP, 0.3 μM each primer). The primers used were Kan-AF and IPCR-R (Table D and SEQ ID NOs 6 and 7). The amplification cycle was as follows:

4° C., hold/94° C., 3 min/(94° C., 15 sec/57° C., 20 sec/72° C., 3 min) X30/4° C., hold.

After inversion PCR 10 μl of the product was visualized on an agarose gel (FIG. 13). There it can be seen that multiple product bands are obtained and more types are made with higher starting colony numbers. A low amount of DNA in the initial ligation results in clean bands and little "smearing" on the gel. It is likely that higher initial DNA levels with lower cycle numbers would give similar results.

The products for the inversion PCRs were purified using a Zymo DNA clean kit (#5) and then cloned using a Promega pGEM-T Easy vector and cloning kit. The inversion PCR products used for this were from the amplifications that utilized 0.5 μl and 0.1 μl of digested target DNA in the ligation mix, for the 5- and 80-colony-pool respectively (FIG. 13, lanes 3 and 8).

Individual colonies were picked from the petri dishes and these were subjected to colony PCR using Kapa Biosystems 2G polymerase, and the same primers that were used for the original inversion PCR (Kan-AF and IPCR-R, Table D, SEQ ID NOs: 6 and 7). The amplification products were separated and visualized on an agarose gel, allowing us to distinguish several different sized products. Plasmid DNA was isolated from these clones and the DNA was subjected to Sanger sequencing, using the primers IPCR-F and IPCR-R (Table D, SEQ ID NOs: 6 and 7). From this, the nature of nine (three and six from the 5- and 80-colony-pools respectively) complete insertion sites were established. The insertion sites are shown in FIG. 14.

Figure 5:
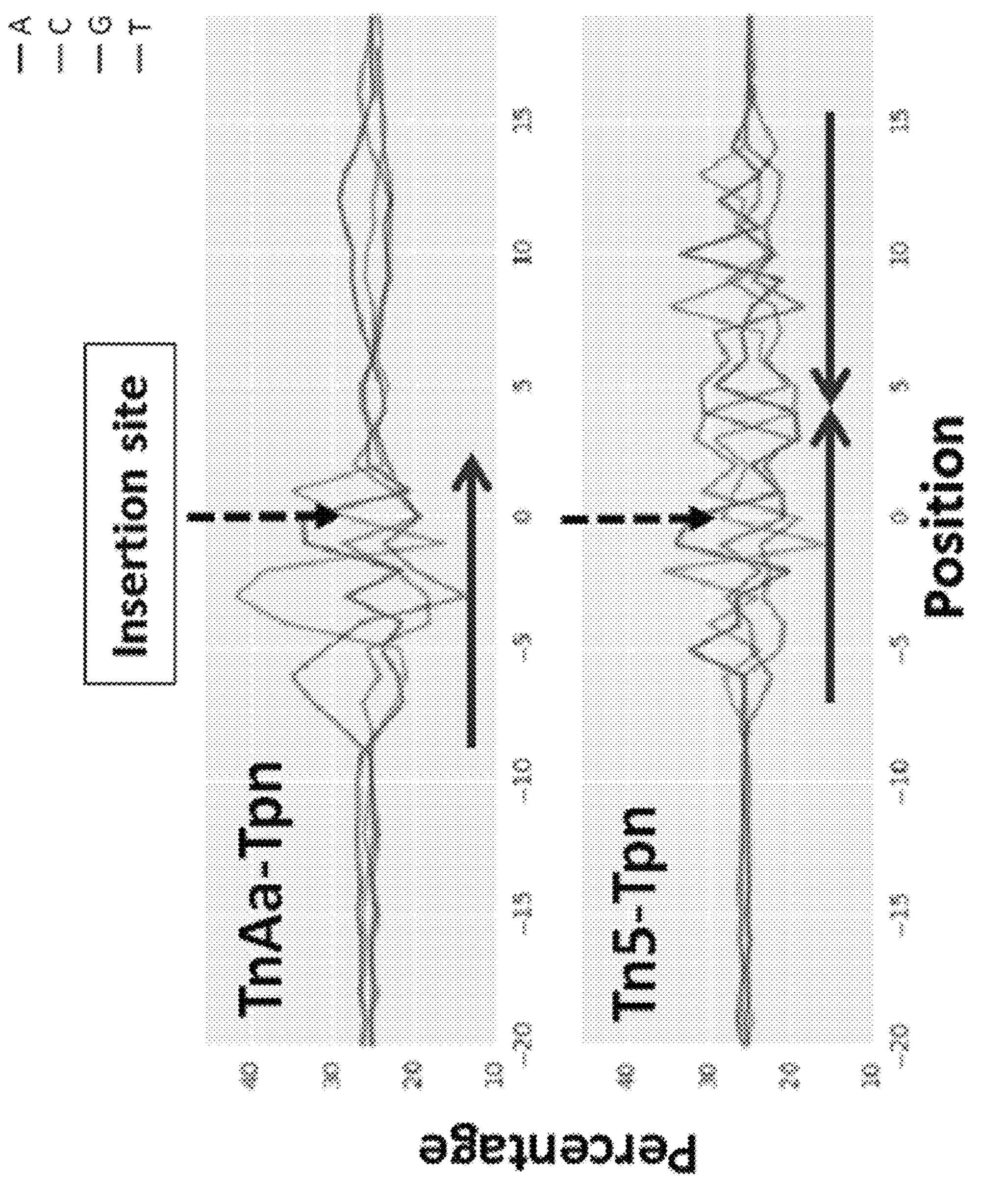
FIG. 5 is a graph providing a comparison of TnAa-Tpn and T5-Tpn insertion site consensus sequences. The consensus sequences of the insertion sites of TnAa-Tpn[P47K]

Of the nine, only four insertion events created a 9-base repeat. Three were 10-base repeats and there were also one each of an 8- and an 11-base repeat. To generate a consensus insertion site, the differences were accounted for by anchoring the alignment at both the right and left-hand cut-sites, and compensating by inserting spaces in the center. The database derived sequences and their reverse compliments were used to generate the consensus, this was to counteract any apparent bias due to strand choice. This should not be necessary when larger numbers of insert sites are analyzed. The results show the insertion sites to be highly biased, especially at positions −2, −3 and −4 from the border of the repeat region (left side of the palindrome). In this experiment the bias at those positions were 100% for CCC, compared to the roughly 40% C in each position for a tagmentation reaction, as shown in FIG. 5. The more pronounced bias may be due to the fact that the transposase is acting in its natural environment, where it has evolved to strictly limit activity, and not in artificial environment comprising buffer, temperature, and cofactors designed to promote promiscuous transposition. Furthermore, the low concentration (a single transposome/cell) and, possibly, the short period for which the transposome might exist before destruction, are also likely to promote extreme bias.

Example 6: Construction of Verified Starter Material

The early proof-of-concept experiments described above have utilized minimal test vectors that were assembled and maintained by PCR. As such, it is likely that within the working stocks and test samples there will be sub-populations that have acquired errors (mutations) during PCR. For the screening experiment it is preferable that, as far as possible, only mutations deliberately targeted to the transposase should be included. In order to achieve this, it is necessary to clone the starter material and confirm that it is free from unintended mutations.

The experimental protocol regarding cloning and vector production for the screening experiment is outlined in FIG. 15; the vector is still assembled in a PCR, in this case, however, it is assembled from starter material that has been cloned and sequenced. The starter material itself comprises two separate parts; the transposase expression signals (including the tet-promoter and ribosomal binding site) are maintained separately from the remaining vector. This is to ensure that the vectors are stable and there are no transposase-driven rearrangements or instability. The two different vector components have a small degree of sequence overlap; this allows them to be assembled and amplified by PCR. The PCR involves moderate amounts of starter template, high fidelity polymerase and few amplification cycles, in order to reduce the possibility of unwanted mutations appearing.

Figures 15A, 15B, 15C, 15D, 15E, 15F:
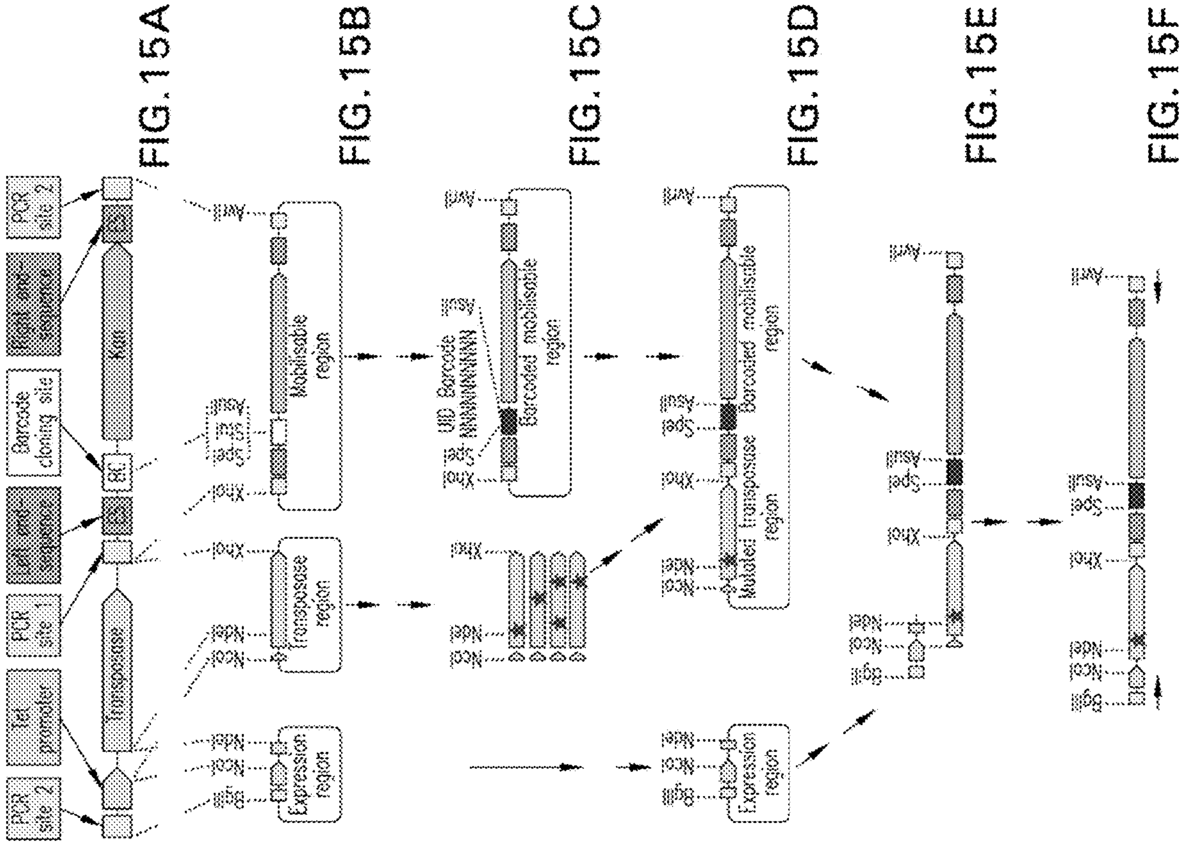

To create verified starter material, the working stocks of the different initial test vectors (FIG. 15A) were used to isolate and clone the regions required to make the constructs shown in FIG. 15B. One plasmid carries the BglII-NdeI promoter fragment (from position 1-194 in SEQ ID NOs: 6 and 7). Two plasmids carry the NcoI-XhoI transposase fragments; both Tn5-Tpn[Hyper] and TnAa-Tpn[P47K] were cloned (from position 163-1622 in SEQ ID NO: 6, and 163-1562 in SEQ ID NO: 7, respectively). One plasmid carries the XhoI-AvrII mobilisable fragment (from position 1617-2734 in SEQ ID NO: 6).

The cloned regions were sequenced and shown to be correct.

Example 7: Construction of Input Vectors and Production of Experimental Vectors

Ultimately two input vectors may be required (FIG. 15D onward); the first, which carries the promoter region, was made as described above (Experiment 6).

The creation of the second type of input vectors, which carry the mutated transposases (both Tn5-Tpn[Hyper] and TnAa-Tpn[P47K] are included) and the complete mobilisable selectable region (including the UID barcodes) is outlined in FIG. 15(B-D).

In the first step, the UID barcode, which comprises 20 bp of random sequence, is inserted into the previously sequence verified plasmid that carries the mobilisable region (in FIG. 15, between the SpeI and AsuII sites). A "barcoded, mobilisable, selectable library" of between 10'-$10^8$ clones is therefore created; each clone carries the mobilisable region labelled with a different barcode (FIG. 15C).

In the next step, the transposases (previously sequence verified, above) are subjected to mutagenesis and cloning (FIG. 15D). Mutagenesis is either by error prone PCR, directed mutagenesis, combinations thereof and/or other methods. Mutagenesis can include the creation of point mutations, and/or deletions, and/or insertions and/or recombination between different transposases. Random mutagenesis methodologies are particularly suited to the identification of important positions and the discovery of new mutations within the transposase. Site directed mutagenesis methodologies are suited to detailed investigations of particular positions. An example of a method to screen particular positions is shown in FIG. 16.

After mutagenesis, the mutation rate and/or type can be determined by sequencing a subset of the DNA fragments. The mutagenized transposases are then cloned (in FIG. 15, as an NcoI-XhoI fragment) into the appropriate site of the barcoded, mobilisable, selectable library. Cloning is strictly controlled to create limited-sized pools of different clones, of known numbers. Pools of $10^3$-$10^8$ are created. These pools of clones are cultured and then stored as primary stocks.

Working stocks of the cells are then made, and after further culture, plasmid DNA is isolated from the cultures.

In the case of the plasmids that represent pools of mutants that will later be used for screening, a sequencing library is made such that the UID barcode and associated mutant transposase can be characterized. One method to achieve this is to isolate the relevant DNA fragments (in FIG. 15, on an NdeI-AsuII restriction fragment) and then attach SMRTbell sequencing adaptors and then sequence using the Pacbio system. Other sequencing methods would serve as well.

In the final steps, the transformation vector is created. First, to create the complete linear vector, the two component parts have to be isolated as shown in FIG. 15E. Briefly, the plasmid DNA is cut with restriction enzymes to free the expression region fragment and the transposase-mobilisable region fragment (in FIG. 15, as BglII-NdeI and Nco-AvrII fragments, respectively) which are then isolated by gel purification. The particular pool size chosen for the latter will determine the number of mutants that are ultimately included in the screening.

Thereafter, the two regions are joined and amplified by assembly PCR, as shown in FIG. 15F. For this, PCR is conducted using both fragments as the mixed template, and primers for the outer ends only (for example the primer pair TPCR-2REEco-F and TPCR-1REEco-R, Table D).

After the linear vector has been made, the circular vector used to deliver the mutant transposase and mobilisable region into the host is prepared, as described in Examples 3 and 4.

Example 8: Creating and Screening Mutant Transposases

In order to demonstrate that the method in its entirety is fit for the intended use, a limited number of previously identified important positions within the test transposon are each subjected to site-directed saturation mutagenesis, as described in FIG. 16. The mutated transposase samples are then pooled, in such a manner that a representative and known number of clones are included in the final library. Otherwise, the procedure is essentially as described in Experiments 7, 3, 4 and 5, but on a limited scale, tuned to the limited number of mutants and samples, and using sufficient NGS power, on the pooled insertion sites, in the final step to identify and count the sites and the associated barcodes. To achieve this, after the clones in which transposition has occurred are isolated, the chromosomal DNA is purified and the insertion sites isolated and amplified, using one of the methods previously described. The insertion site fragments are then prepared for sequencing by the addition of Illumina adaptors, and then sequenced.

After sequencing, the reads are sorted by UID barcode, and the insertion sites are aligned to the *E. coli* reference sequence. From this, all the different insertion sites for each barcode can be counted and then aligned with each other, anchored at the insertion site. If both ends of the insertion were sequenced, the repeat length can be determined and either appropriate spacing can be applied, or the insertion sites can be binned according to length and analyzed separately. Once aligned, the fraction of each of the four bases at each position (relative to the insertion site) is determined, and the bias is determined, a consensus can be derived and the mutant genotype is then linked to the bias profile. Where possible, identical mutations (but with different barcodes) are identified, and these are checked to determine if similar bias profiles are found. Different mutations at the same position are similarly analyzed.

In addition to examining bias, the correlation of activity of the transposases with the insertion site numbers (which reflects transposition likelihood) is examined. Null and low activity mutants are easily identified, as these are represented by barcodes that were present in the original library but are not represented in the insertion site collection. Where no activity change has occurred, the number of insertions is similar to those obtained with the non-mutated parental transposases. However, those barcodes that are over-represented in the insertion site collection represent transposase mutants that display higher activity, at least under the conditions of this experiment. Again, the mutations responsible for this are identified by cross referencing the barcodes to the library of mutants.

Example 9: Identification of Novel Mutants

The identification of novel mutants and important positions require that the mutant library to be screened is generated by random or semi-random mutagenesis, and that a large number of mutants are screened. Otherwise, the procedure is essentially as described in Examples 7, 3, 4, 5 and 8, but on a much larger scale, and using deep NGS in the final step to identify insertion sites and associated barcodes.

A typical screening experiment therefore involves utilizing a library of $1\times10^5$ or more mutant transposases, and aiming for $1\times10^7$ or more transposition events. This should yield, on average, more than 100 transpositions/mutant examined, as a fraction of the original pool of mutants will be inactive.

After sequencing, the reads are sorted by UID barcode, and the insertion sites are aligned to the *E. coli* reference sequence and results are analyzed as described in Example 8. Due to the large numbers involved, insertion sites are pre-screened for information content, in order to identify probable bias-type variants, before more detailed analysis is conducted.

Example 10: Recombination and Saturation Mutagenesis

From the analysis described in Example 9, the positions and type of useful novel mutations are obtained. A further experiment is then conducted in which these newly identified positions are subjected to site-directed saturation mutagenesis and screening, essentially as described in Example 8. In this way every possible mutation at each position of interest is examined. These mutants are tested individually and also when specifically or randomly recombined.

Example 11: Library Generation

A selection of mutant transposases are cloned, expressed and purified. These mutant transposases are then used to create an NGS library by tagmentation. The insertion bias of such a library is then assessed Example 12: Barcode-Assisted Transposase Screening (BATS)

An experiment using the novel massively parallel method of Barcode-Assisted Transposase Screening (BATS) described above was performed, essentially as described in Example 8. The hyperactive Tn5 (SEQ ID NO: 1) was used as the reference transposase. Several constructs were made with mutations in addition to those in hyperactive Tn5. Amplicons comprising a mutant transposase region and a barcoded mobilisable region was constructed, circularized and used to transform *E. coli*. Active transposases catalysed the "jumping" of the mobilisable region into the *E. coli* genome resulting in Kanamycin resistant colonies. Genomic DNA was isolated and Illumina sequencing-ready libraries were prepared of genomic DNA containing the UID (barcode) and the genomic insertion site (jump-site). The library prior to transforming *E. coli* was sequenced using PacBio to establish linkage between barcodes and their associated transposase sequence. The barcodes in the library prior to transforming *E. coli* was also sequenced separately using, for example, Illumina sequencing.

Example 13: Effective Mapping of Genotypes to Barcodes

The overall information flow in one demonstration of analysis of a BATS experiment works in three steps:

1. Process Genotype-Barcode data, G, from a long-read PacBio sequencing run, to simultaneously extract the barcodes and the genotypes from within a construct containing known sequences. This process was termed genotype segmentation. We used regular expressions in python to recognise the known sequences, and thus isolating the variable genotypes and barcodes. The process was an iterative optimisation, in which the number of overlapping barcodes between G and J (from jump-site segmentation, see below) was optimised by varying the allowed numbers of mismatches, insertions or deletions in the regular expressions for genotype segmentation.

2. Process Jump-site data, J, from a short-reads Illumina sequencing run, to simultaneously extract the barcodes and the jumps-sites (insertion sites), from within a construct containing known sequences. This was also an iterative segmentation process. In this case, we used the overlap with a third dataset, B, which consisted only of barcodes segmented from within a construct of known sequences. The dataset B was generated by sequencing excised barcodes from the library prior to transformation of *E. coli*. The *E. coli* DNA inserts obtained from R2 varied in length from one base pair to 60 base pairs. For motif analysis, only DNA inserts of at least 20 base pairs could be used, while for the coverage sub-sampling by locus approach (CSSL), shorter DNA inserts could be used, an in addition, the full length R1 could also be used in the latter method (later discussed).

3. Processing of genotype data. A caveat is that long-read sequencing, such as on PacBio, is highly error-prone. We used a specialised polishing step to get rid of the abundance of insertions and deletions characteristic of long-read sequencing. For this, we used pairwise alignment of the transposase sequences with the expected Tn5 sequence, using the program clustal. Subsequently. All insertions were deleted, which are typically polynucleotide repeats, while all deletions were filled in as 'N'. The length of barcodes was controlled to be 20 base pairs.

4. Intersecting Genotype-Barcode and Jump datasets via barcodes. A caveat exists in that sequencing error in barcodes could render a barcode unrecognisable in one or more datasets. Even though an edit distance or Leuvenstein distance approach slightly improved the overlap of barcodes, the exact overlap of barcodes was sufficient for mapping between datasets G and J, whereas distance-based methods were computationally non-feasible given the large number of reads. The barcode-genotype association was captured in a barcode-genotype counts matrix, BG. The genotypes were defined as joint codon genotypes, a general term used to represent a genotype which may have any number of mutations compared to the background genotype, even though only a single mutation was targeted in the dataset described. Rows in BG represent barcodes, while columns represent genotypes. For defining a motif of a genotype, each non-zero entry in a column in BG (representing a genotype) were used to extract the relevant barcode (row identifier). For each barcode, all reads in the jump data J carrying those barcodes were harvested, an aligned DNA sequence pile-up created (20 base-pairs), and a motif generated. For the coverage sub-sampling approach, the data in an aligned bam file generated from the DNA inserts of the segmented R2 jump-data with barcoded read identifiers was traverse instead. Barcodes were then followed in the matrix BG to obtain the genotypes.

5. A caveat exists in that a single barcode might map to multiple genotypes, due to low complexity in the original barcode diversity. The matrix BG was conveniently used to extract only barcodes mapping to a single genotype (pure barcodes). The same intersecting step (step 4) could then easily be done on pure barcodes only.

Example 14: Analysis of Inter-Motif Distances

The novel massively parallel method of Barcode-Assisted Transposase Screening (BATS) simultaneously produces rich information regarding both the mutant genotype and its preferred insertion motif. However, several aspects limit the traditional motif-based methodology applied to the analysis of cutting bias. For each of these limitations, innovations in analytics had to be developed, which are described below.

A Low Number of Jumps Per Genotype Requires Statistical Interpretation of Inter-Motif Distances In studies involving the evolution and selection of mutant enzymes that cut DNA or RNA, the emphasis is typically on the analysis of the combined sequence motif at the 5'-end of DNA cut sites. Analysis of such sites as motifs in the form of positional weight matrices or positional frequency matrices uses this 5'-bias as a proxy for genomic coverage bias. These matrices can in turn be visualized as bias plots in a manner similar to that described by Kia et al. (Kia et al. 2017. BMC Biotechnology. 17:6). The first limitation is that, due to the massively parallel nature of BATS experiments, a high mutant library diversity might limit the number of DNA insertion sites (jump sites) obtained per mutant. The result is that the typical analysis of insertion sites as 5'bias motifs becomes too difficult for the human eye to distinguish as a result of too few jumps into the genome, ie too few sampling events. A different approach is to use motif entropy, which incorporates the number of reads. However, a different approach is proposed here for BATS experiments, which is to use a network distance approach between motifs, with an appropriate statistical interpretation, as described below.

The distances between motifs of two transposases in our study were calculated from the positional-frequency matrices of the sequence reads of jumps of transposase mutants into the genome. First, the absolute difference in fractions of reads with a "C" at position 1 between a reference and test transposase is calculated (FIG. 17). This calculation is repeated for positions 2-20 and the absolute differences across all 20 positions in the read are summed. Similar calculations are performed for nucleotides "T", "A" and "G". The absolute differences for all four nucleotides at all 20 position are summed and divided by 20 to give the average difference per position. This difference is called the distance or inter-motif distance.

Inter-motif distances cannot be interpreted directly, since they are dependent on the number of sequences in each of the two motifs in the comparison. We developed a bootstrapping method, coupled with interpolation of simulated datasets to provide a smoothed lookup for a p-value, given a calculated distance, and the numbers of reads in each of the two motifs (described below). The bootstrapping results, herein defined as an inter-motif distance probability plot, are shown in FIG. 18, which demonstrates the effect that the number of sequences in both motifs have on distance.

This cumulative distribution function used to look up p-values was obtained from the probability density function, which was generated empirically by random background sampling. For the experiment, the background genome was sampled randomly as k-mers (20 base-pairs in this application), each time compiling a two pileups, with a and b sequences, and the process repeated many times, saving the distances each time, along with a and b. Subsequently, the distances were binned into bins d, converting the data into a table with value a, b and d and c, where d is the distance bin and c the number of times that a distance in bin d has been observed. Thereafter, the counts were converted to probabilities p, and subsequently, to cumulative probabilities. For example, distance score values larger than 0.95 may be interpreted as significant.

The major caveat in the approach was to convert the simulated data into a densely sampled dataset, with a convenient lookup functionality, which can also take any given distance measurement. Due to the large dynamic range of distances obtained, sampling was increasingly dense towards lower sequence counts a and b. Sampling sufficiently dense to allow approximate p-value lookup was computationally intractable, however. We instead interpolated over the distance-probability domain at a given a an b, using the interpolate package in the python scipy library to generate more data points in between true sampling values. This provided us with the required sampling density required to accurately obtain the relevant p-values. Next, interpolation was again used to fit the simulated data with a, b and d as inputs, allowing easy access to p-values p, which is fast enough to allow all-against-all comparison statistics involving thousands of motifs.

The start-site bias for the BATS experiment described in example 12 was calculated in terms of position frequency matrices and bias plots were generated as exemplified in FIG. 19. The distances between motifs were calculated and the results are shown in Table E.

These data show that mutations at positions E146, W125 and G251 result in insertion site motifs that are significantly different from that of the reference transposase hyperactive Tn5.

TABLE E

Distance to reference of insertion site for selected mutants. A pair of motifs with a distance corresponding to a p-value larger than 0.95 can be considered as significantly distinguishable, considering the number of sequences used to calculate the motifs.

| Transposase mutant | Distance | p-value | Number of sequences* |
|---|---|---|---|
| E146S | 0.126 | 1.000 | 316 |
| E146N | 0.120 | 1.000 | 178 |
| E146A | 0.114 | 1.000 | 533 |
| E146C | 0.200 | 1.000 | 304 |
| G251A | 0.074 | 0.992 | 352 |
| W125G | 0.102 | 0.987 | 858 |

*The number of sequences used for reference: 3490 reads.

Another way of illustrating jump site bias is by plotting sequence logos. In order to determine jump site nucleotide sequence bias for each transposase variant sequence logos were generated using the website "WebLogo3" (http://weblogo.threeplusone.com/; Crooks et al. (2004) Genome Research, 14:1188-1190; Schneider et al. (1990), Nucleic Acids Research. 18:6097-6100). Multiple 60 base-pair sequences containing the respective jump sites for each variant were aligned for this purpose. The sequence logos are show in FIG. 20. The overall height of the nucleotide letter containing stack indicates the sequence conservation at that position, while the height of nucleotide letters within the stack indicates the relative frequency of the respective nucleotides at that position. This analysis highlights the importance of certain nucleotide positions and—compositions important for transposase variant-DNA interaction. However the examination of sufficient jump sequences are required in order separate significant nucleotide positions from those contributing to background noise. This is clearly illustrated by the low overall background signal observed in the motif generated from 86 sequences for variant E146C as opposed to absence of this background signal in all the other variants constructed from more (in excess of 177) sequences (see Table F).

Example 15: Coverage Sub-Sampling by Loci as an Alternative to Inter-Motif Distance Analysis of Data from BATS Experiments Another limitation is that 5'-motifs might not sufficiently capture the essence of coverage bias, as in the scenario of library preparation in the form of tagmentation of purified DNA. An important goal in library preparation protocols is to obtain both even and complete coverage of the genome or transcriptome targeted, and 5'-bias could be seen as merely partly correlated with genomic coverage, or even merely a cosmetic feature. Also, the representation of a motif as a single positional weight matrix, or as a single positional frequency matrix, essentially captures an averaged binding strength-related profile, and does not fully make use of joint likelihoods of neighbouring bases at potentially variable distance(s). Using more complex models such as Markov models or neural networks would essentially require more reads, scaling strongly with the order of the model, making them less useful for detecting differences in limited data. It would be ideal to be able to interpret results directly in terms of coverage over the genome. The fact that coverage over the genome is not sufficient in a highly multiplexed experiment like BATS where thousands of mutants can potentially be screened in parallel, effectively excludes the direct targeting of coverage from low sequence read numbers, resulting in the use of the proxy of motif analysis. However, in this method disclosure, we show that the comparative genomic coverage is indeed accessible by using the genomic loci of jumps from a BATS experiment.

Coverage Sub-Sampling by Loci (CSSL) works by first mapping the sequenced genomic DNA insert of the transposase jump site to the appropriate reference genome, and relate the genomic locus to the expected coverage of a reference dataset R that has a sufficient coverage to serve as a reference coverage distribution. We effectively sample the sample datasets of interest, S, from the distribution R by using the same genomic coordinates. Effectively, the genomic locus makes the rational link for mapping data from reference genotype R to the sample genotype S of interest. The reference genotype R could for instance be the wild-type form of the Tn5 transposase applied in tagmentation in a normal library preparation experiment, or a library preparation using tagmentation with an enzyme available in the market, whereas the sample genotype S might refer to the mutant genotypes originating from site-directed mutagenesis or random mutagenesis in a BATS or related experiment. For each of the sample genotypes, a sample distribution S is sampled from the reference distribution R via the genomic loci, and subsequently the two distributions R and S are compared using statistical tests such as 1) the Mann-Whitney Test for differences in means, 2) the Kolmogorov-Smirnoff Test for different distribution shapes, 3) other parametric or non-parametric tests, 4) visual inspection of shape differences, 5) percentile-based metrics such as the percentage of loci sampled at less than 25% of the mean coverage in the parent distribution, or any other method to detect differences in shape. In this manner, mutants may be selected which can access those loci better than the reference R or background B transposases can access.

An additional flexibility in the method is that samples, 5, may be compared to one another. For instance, mutant sample S1 could be compared to wild-type or background genotype B from which S1 was originally mutated, for which the distribution is also obtained by CSSL using reference R.

As an example, CSSL analysis was performed on data from the same BATS experiment as in example 12 and the results are indicated in FIGS. 21 and 22. In this experiment, reference genotype B is the hyperactive Tn5 transposase resulting in the reference data set B. The sample data sets, S, are derived from Tn5 mutants that each have a mutation in addition to those in hyperactive Tn5. Statistical tests are done on the comparison of S with B and the resulting p-values for both the Mann-Whitney and Kolmogorov-Smirnoff tests are indicated in Table F. The data in FIG. 21 shows the data for two mutants, W125G and G251A, and the reference hyperactive Tn5. The mobilisable element associated with two transposase mutants inserted into the genome at loci that tend to show lower coverage with the reference data set B, generated with hyperactive Tn5. Improved coverage in regions with low coverage of the reference transposase R, or background transposase B, would be beneficial, for example in variant calling, as described below. The data in FIGS. 21 and 22 were smoothed solely for visualization purposes by calculating and plotting the mean of 3 three data points.

In a similar way, the results of CSSL analysis of data for mutations E146A, E146C, E146N and E146S are depicted in FIG. 22. It is evident from FIG. 22 that particular mutations at position E146 in Tn5 result in preferential insertions into the genome at loci in the genome that are well covered by the reference transposase. As such, these mutations at position E146 have an increase in bias. This further illustrates the utility of this method in determining differences in bias between mutants and how this relates to transposase mutants preference for insertion into low vs high coverage regions of the genome.

TABLE F

Statistical analysis of reference data distribution for selected mutants. For the Kolmogorov-Smirnoff and Mann-Whitney analyses p-values of <0.15 and <0.05 are respectively considered significant.

| Transposase mutant | p-value (Kolmogorov-Smirnoff) | p-value (Mann-Whitney) | Number of sequences* |
|---|---|---|---|
| E146S (SEQ ID NO: 22) | $6.20 \times 10^{-6}$ | $1.088 \times 10^{-8}$ | 252 |
| E146N (SEQ ID NO: 21) | $1.67 \times 10^{-5}$ | $1.71 \times 10^{-8}$ | 86 |
| E146A (SEQ ID NO: 19) | $5.95 \times 10^{-4}$ | $2.23 \times 10^{-6}$ | 365 |
| E146C (SEQ ID NO: 20) | $2.20 \times 10^{-2}$ | $5.58 \times 10^{-4}$ | 177 |
| G251A (SEQ ID NO: 24) | $2.58 \times 10^{-3}$ | $1.440 \times 10^{-4}$ | 235 |
| W125G (SEQ ID NO: 18) | $9.07 \times 10^{-3}$ | $3.35 \times 10^{-3}$ | 674 |

*The number of sequences used for reference: 2005 reads.

Low-coverage regions are typically the cause of false variant calls such as SNPs and indels, due to a lack of evidence for the variant caller. Conversely, incorrect-alignment of reads with multiple positions with equal mapping quality due to repeats in the genome could also result in false variant calls due to the introduction of alignment-borne errors, correlating with regions of excessive coverage in such regions. In such a scenario, coverage sub-sampling lends itself to the selection of mutants with a lack of coverage in the high-coverage region. The sub-sampling might for instance also be limited to the most relevant regions, such as the regions of interest, including biologically encoding regions, lists of target loci for variant calling, or any other locus-specific criterion.

Hence, even with the lower read numbers obtained during massively parallel BATS experiments with high numbers of genotypes, genomic coverage could be accessed without requirement for motif analysis. In another form of CSSL, the distributions R, S and B could be converted to a chosen descriptive feature, such a GC content, higher dimensional k-mer frequency, or known DNA modification pattern as a function of the locus. It is common practice to compare library preparation technologies in terms of their GC-bias on genomic level. CSSL provides an effective method to select for GC-unbiased enzymes during BATS experiments.

The data from the above BATS experiment was analysed with the aim of establishing whether Tn5 transposase mutants display an altered GC-bias. The jump sites (insertion sites) for a reference transposase (Hyperactive Tn5) and mutants were mapped to the reference genome and the GC content of a 100 bp window was calculated. FIGS. 23 and 24 are plots of the probabilities of insertion of a given transposase as a function of the GC-content of the target DNA. FIG. 23 shows the jump site data for two mutants and the reference Hyperactive Tn5. The two mutants, P214S (SEQ ID NO: 23) and G251A (SEQ ID NO: 24), have a significantly increased preference for lower GC-content than the reference transposase (see Table G for p-values). That the Tn5 mutant G251A has an increased insertion preference for low GC-loci could potentially be the mechanism by which the same mutant has an increased probability for insertion at loci that are low-coverage loci as indicated in FIG. 21.

FIG. 24 shows the jump-site data from three Tn5 mutants. These three mutants, E146N, E146A and E145S, have higher probability of insertion into high-GC loci compared to that of the reference transposase. Mann-Whitney and Kolmogorov tests for differences in the mean and curve-shape, respectively, were performed and the p-values are indicated in Table G.

TABLE G

Statistical analysis of reference data distribution for selected mutants. For the Kolmogorov-Smirnoff and Mann-Whitney analyses p-values of <0.15 and <0.05 are respectively considered significant.

| Transposase mutant | p-value (Kolmogorov-Smirnoff) | p-value (Mann-Whitney) | Number of sequences* |
|---|---|---|---|
| E146S | 0.0 | 0.0 | 177 |
| E146N | 0.0 | 0.0 | 365 |
| E146A | $1.4 \times 10^{-5}$ | 0.0 | 252 |
| G251A | $1.03 \times 10^{-2}$ | $5.1 \times 10^{-5}$ | 673 |
| P214S | $2.71 \times 10^{-2}$ | $4.25 \times 10^{-3}$ | 420 |

*The number of sequences used for reference: 2005 reads.

What is claimed is:

1. A method of screening a plurality of transposases, wherein the method comprises the following steps:

(a) contacting a first transposase with a first nucleic acid sample under conditions sufficient to induce transposition of a first oligonucleotide, wherein the first oligonucleotide comprises a first end sequence, thereby generating a first transposed nucleic acid sample having a first plurality of insertion sites of the first end sequence;

(b) contacting a second transposase with a second nucleic acid sample under conditions sufficient to induce transposition of a second oligonucleotide, wherein the second oligonucleotide comprises a second end sequence, thereby generating a second transposed nucleic acid sample having a second plurality of insertion sites of the second end sequence, and wherein the sequence of the second transposase and the sequence of the first transposase differ by at least one amino acid;

(c) sequencing at least a portion of the first plurality of insertion sites of the first transposed nucleic acid sample, thereby generating a first set of sequencing reads, wherein each of the first set of sequencing reads comprises one of the insertion sites of the first end sequence;

(d) sequencing at least a portion of the second plurality of insertion sites of the second transposed nucleic acid sample, thereby generating a second set of sequencing reads, wherein each of the second set of sequencing reads comprises one of the insertion sites of the second end sequence;

(e) determining an inter-motif distance between a motif of the first transposase and a motif of the second transposase by: (i) calculating the frequency of each possible nucleotide base at each nucleotide position for the first set of sequencing reads, thereby generating a first set of frequency values, (ii) calculating the frequency of each possible nucleotide base at each nucleotide position for the second set of sequencing reads, thereby generating a second set of frequency values, (iii) calculating an absolute difference between the first set of frequency values and the second set of frequency values for each possible nucleotide base at each nucleotide position, thereby generating a set of absolute difference values, and (iv) averaging each of the absolute difference values, thereby determining the inter-motif distance; and (f) based on step (e), determining a probability that the second transposase is significantly different from the first transposase.

2. The method of claim 1, wherein the step (f) of determining a probability comprises the following steps:

(i) generating an inter-motif distance probability plot defined by simulated random sequence reads; and (ii) determining the probability value that the second transposase is significantly different from the first transposase based on the inter-motif distances determined in the step (e) and the inter-motif distance probability plot.

* * * * *